US008617873B2

(12) United States Patent
Solomon

(10) Patent No.: US 8,617,873 B2
(45) Date of Patent: *Dec. 31, 2013

(54) INTELLIGENT MEDICAL DEVICE SYSTEM FOR PERSONALIZED MEDICINE APPLICATIONS

(76) Inventor: Neal Solomon, Oakland, CA (US)

( * ) Notice: Subject to any disclaimer, the term of this patent is extended or adjusted under 35 U.S.C. 154(b) by 897 days.

This patent is subject to a terminal disclaimer.

(21) Appl. No.: 12/462,781

(22) Filed: Aug. 7, 2009

(65) Prior Publication Data

US 2010/0069888 A1 Mar. 18, 2010

Related U.S. Application Data

(60) Provisional application No. 61/188,456, filed on Aug. 8, 2008.

(51) Int. Cl.
*A61M 37/00* (2006.01)

(52) U.S. Cl.
USPC ............ 435/287.1; 435/287.2; 422/68.1; 706/46; 604/890.1; 702/19; 702/20

(58) Field of Classification Search
USPC .............. 435/287.2, 287.1; 706/46; 422/68.1; 702/19, 20; 604/890.1
See application file for complete search history.

(56) References Cited

U.S. PATENT DOCUMENTS

| 2003/0140317 A1* | 7/2003 | Brewer et al. ............ 716/1 |
| 2004/0147906 A1* | 7/2004 | Voyiazis et al. .......... 604/891.1 |
| 2005/0043894 A1* | 2/2005 | Fernandez ............... 702/19 |

* cited by examiner

*Primary Examiner* — William H Beisner
*Assistant Examiner* — Danielle Henkel

(57) ABSTRACT

The system presents applications of personalized medicine with intelligent medical devices (iMDs) and customizes therapies to complex problems involving neurological, cardiovascular, cancer, immunological and endocrinological diseases.

21 Claims, 50 Drawing Sheets

FIG. 43

[Diagram showing module with sections A1, D1, T1, T2 labeled 4300, with 4305, 4310, 4315, 4320 and arrows connecting to cellular structures labeled 4325, 4330, 4335, 4345, 4350, 4340]

FIG. 44

IMD diagnostic probes are dispatched to infected cells to collect samples — 4400

↓

Probes return to diagnostic module for evaluation of infectious agent — 4410

↓

Data is sent to analytical module for modeling of virus composition — 4420

↓

Modeling data is transmitted to therapeutic module which applies protein or peptides to inhibit virus infectious aspect — 4430

↓

Proteins are inserted in antibodies for delivery to virus — 4440

↓

Virus is rendered inert — 4450

FIG. 45

```
IMD diagnostic module probes
are dispatched to infected        — 4500
cells to collect samples
            ↓
Samples are evaluated in
diagnostic module and data
sent to analytical module for     — 4510
viral modeling
            ↓
Modeling data is transmitted
to therapeutic module, which
inserts gene to disable           — 4520
infectious viral gene
            ↓
Modified genes are inserted in
antibodies for delivery to virus  — 4530
            ↓
Virus is rendered inert           — 4540
```

FIG. 46

```
IMD diagnostic module probes
collect infected cell samples     — 4600
            ↓
Samples are evaluated in
diagnostic module and data
sent to analytical module for     — 4610
viral modeling
            ↓
Modeling data is transmitted
to therapeutic module, which
activates a protein to stimulate  — 4620
HIS antibody cascade
            ↓
Therapeutic module releases
mild antigens to stimulate        — 4630
antibody cascade
            ↓
Virus is attacked by HIS
acceleration                      — 4640
```

FIG. 57

Cancer genes, by cancer type

| Cancer type | Gene Family |
|---|---|
| Noster Gene | P 53 |
| Colorectal | Adenomatous polyposis coli (APC)<br>MSH2, MSH6 (Chromosome 2)<br>MSH1 (Chromodome 3) |
| Skin | BRAF (mutated in 70% of malignant melanomas) |
| Pancreatic | 96 genes (cf. list) |
| Liver | (Hepatocellular carcinoma - (HCC))<br><br>- Iqgap1 & Iqgap2 ⟶ 80% of liver cancer<br>   ↓       ↓        ↓<br>turn on & loss  (more aggressive cancer)<br><br>Alpha-fetoprotein (AFP) ⟶ biomarker<br><br>∗ DLC1-3 tumor suppressor genes / (chromosome 8) ⟶ regulator of family of enzymes (small Rho GTPases) that act as molecular switches |
| Leukemia | dozens - (Cf. list) |
| Prostrate | 11 genes - (Cf. list) |
| Breast | chromosome 17q    chromosome 13<br>BRCA1 & BRCA2 - tumor suppressor genes<br>SATB1 ⟶ regulator gene ⟶ when gene is active, cancer is aggressive<br>P 53<br>ATM<br>P65 |

FIG. 58

| Carrier Options | Container entity | Coating for navigation | Coating for cell penetration | Coating for immune resistence |
|---|---|---|---|---|
| Single Model | | | | |
| Virus<br>adinovirus<br>retrovirus<br>lentivirus<br>other | - Genes<br>- Antibodies<br>- RNA<br>- Proteins<br>- Nanodevices | - Targeting proteins<br>- Antibodies | - Cell surface proteins | - Immune proteins<br>- Antibodies |
| Antibody<br>Multiple types | - Genes<br>- RNA<br>- Proteins<br>- Nanodevices | - Targeting proteins | - Cell surface proteins | - Immune proteins<br>- Antibodies |
| Patient Cells<br>Multiple types | - Genes<br>- Antibodies<br>- RNA<br>- Proteins<br>- Nanodevices | ——— | ——— | ——— |
| Stem Cells | - Genes<br>- Antibodies<br>- RNA<br>- Proteins<br>- Nanodevices | - Targeting proteins | ——— | - Immune proteins<br>- Antibodies |
| Combination | | | | |
| Stem Cells | - Stem cells contain virus, antibodies genes, nanodevices &/or proteins | - Targeting proteins | ——— | ——— |
| Virus | - Virus contain antibodies, genes, nanodevices &/or operations | - Targeting proteins | - Cell surface proteins | |
| Antibodies | - Antibodies contain nanodevices, genes & proteins | - Targeting proteins | - Cell surface proteins | |
| Nanorobots | - Nanodevices contain proteins, antibodies &/or genes released on demand | - Targeting proteins | - Cell surface proteins | - Version A: coated with proteins &/or antibodies for immune resistance<br><br>- Version B: not coated with antibodies to provoke immune response when targeted to tumor |

INTELLIGENT MEDICAL DEVICE SYSTEM FOR PERSONALIZED MEDICINE APPLICATIONS

CROSS-REFERENCES TO RELATED APPLICATIONS

The present application claims the benefit of priority under 35 U.S.C. §119 from U.S. Provisional Patent Application Ser. No. 61/188,456, filed on Aug. 8, 2008, the disclosure of which is hereby incorporated by reference in their entirety for all purposes.

FIELD OF THE INVENTION

The invention involves a medical device system, including lab on a chip (LOC) components for application of customized medical therapies. The invention applies to diagnostic and therapeutic aspects of medical intervention affecting neurological, cardiovascular, cancer, immunological and endocrinological disorders.

BACKGROUND

As scientists discover the mechanics of genetic processes, our understanding of the sources of diseases increases. The benefits of understanding genetic dynamics and proteomics regulatory processes assists in development of a new generation of medical devices able to diagnose, regulate, manage and cure complex diseases. The potential exists to develop personalized drug therapies to target specific genetic pathologies.

Regarding diagnostic systems, MEMS is an umbrella for a class of new medical devices able to identify genetic mutations and proteomic dysfunctions. While largely external in vitro devices, DNA microarrays, RNA microarrays and protein microarrays provide feedback to identify an individual's genetic information. Protein microarrays use antibodies to assess protein functional responses. In addition, whole cell assays test cells with analytes to assess specific responses to chemical inputs. Multi-phenotype cellular arrays are used for bio-sensing of specific inputs in order to study cell functions.

Though DNA, RNA, protein and whole cell arrays have developed separately, a new generation of lab on chip (LOC) and micro-total analysis systems (μTAS) technologies have emerged as well that integrate several functions in a single device. These multi-purpose arrays provide clinical diagnostic data to practitioners.

In addition to these external devices, the evolution of radiological diagnostic tools has provided a revolution to analytical practitioners. In particular, the use of CT, PET and MRI technologies provides detailed data on specific disease progression. In addition to these external radiological diagnostic technologies, the internal sensing "pill" camera records and transmits digital images to substitute for the surgical intervention of exploratory surgery. Finally, the use of implanted sensors assists in the regulation of simple deterministic expert systems.

The convergence of nanotechnology with biology has produced "bionano" devices. In the main, the use of nanotechnology is limited to particles that are targeted to specific tissue in order to identify pathology and, when combined with directed radiation, provide a therapeutic alternative. The advent of self-assembled peptide nano-biomaterials provides interesting opportunities for diagnostics and therapeutics. The use of nano-scale devices, in which collective behaviors are controlled for therapeutic as well as diagnostic modes, provides an advancement of the bionano field.

Regarding therapeutic medical devices and systems, the field has evolved from the development of the hearing aid and the cardiac pace maker. For instance, the implantable brain pacemaker has been developed to regulate epileptic energy pulses and blood glucose monitoring is regulated with an insulin pump. Moreover, implantable pain management devices are used to control chronic pain. Microfluidic devices to target drug delivery, primarily using a deterministic expert system control model, have also been developed. All of these devices are simple single-function mechanisms targeted to a specific disease or disorder.

An emerging scientific field is providing a new set of technologies from bio-inspired computing. Complexity science deals with self-organizing systems that learn in indeterministic environments. The inspiration from the autonomic nervous system and the human immune system provide computing systems that emulate these complex biological processes. Autonomic computing self-diagnoses, self-heals and self-regulates distributed networks. The human immune system provides inspiration for immunocomputing models that emulate protein regulatory network behaviors in order to solve complex optimization problems. Swarm intelligence metaheuristics provides solutions to optimization problems as well. For instance, the ant colony optimization (ACO) metaheuristic provides a model to solve network computing problems. These models share the ability to develop solutions to problems in self-organizing systems, including plasticity behaviors, in indeterministic environments. In effect, these complex computing and control systems learn. So far, these complex computing models have not been applied to medical devices.

The ability to use genetic and proteomic information to solve complex pathologies provides a new generation of opportunities to build medical devices that are customized to each individual's specific disease(s). Our understanding of cancer, for instance, as the combination of multiple genetic mutations, suggests that each disease type is classed into a typology that can be solved with specific targeted therapies. Given this new knowledge, it is logical to build medical devices that are personalized to specific diseases of each individual. In particular, the use of medical devices focused on solving problems involving pathologies associated with cardiovascular, neurological, immunological and endocrinological systems, and with cancer, is a next step.

Each of the prior medical devices has limitations. For the most part, none of the implantable medical devices are "intelligent". Rather, they are simple deterministic systems. They are also single function devices focused on a specific narrow medical problem. Because they are merely deterministic expert systems, they do not combine diagnostic and therapeutic functionality. In the diagnostic mode, they do not provide sophisticated modeling functions. Further, prior MDs are not networked since they typically involve a single device performing a single function. Finally, these devices are not useful in personalized medicine, which require complex analysis and targeting of individual therapies to unique problem sets.

What is needed? We need active intelligent medical devices that are able to work with other medical devices to solve multiple medical problems. We need complex medical devices that are capable of integrating diagnostics and therapeutics in order to maximize efficiency, to promote early detection and treatment and to modify functionality with feedback mechanisms to solve complex biological optimization problems in biological regulatory networks. The present system develops an intelligent multifunctional medical device system.

Problems that the System Solves

The present system solves a range of problems. How can we develop an intelligent medical device (iMD) that coordinates diagnosis and therapy? How can the iMD coordinate sensors and integrated circuits? How is the processing of chemical and biological fluids administered by using the iMD? How is the implantable iMD coordinated with external computation and modeling? How does the device collect samples and data in real time? How does one integrate multi-functionality into an efficient iMD design? How is the implantable device installed with minimal invasiveness? How are nano-components integrated into the iMD? How does the iMD use sensors and probes for maximum effect? How does the iMD efficiently analyze biological data? How are solutions to complex problems developed and refined in the iMD? How is drug delivery optimized in the iMD? How can we construct customized drugs for therapies to individual patient pathologies? How can an iMD self-organize and adapt to indeterministic environmental conditions? How can multiple iMDs be coordinated, particularly for multiple applications? Solving these problems presents opportunities to develop a new generation of highly effective medical devices.

SUMMARY OF THE INVENTION

The iMD system is used to solve complex optimization problems involving several classes of disease pertaining to specific human physiological subsystems. These customized solutions to pathologies involve the neurological system, the cardiovascular system, the immune system and the endocrine system as well as cancer pathologies. These systems are complex regulatory networks that require a balance of attributes. When a combination of genetic anomalies is present, the regulatory networks of these physiological systems present as pathologies.

The iMD system diagnoses complex pathologies and develops and applies solution options in real time to each of these subsystems or to all of them simultaneously. The system uses a combination of diagnostic and therapeutic modules in multiple iMDs in a network to identify and apply remedies to pathologies.

The iMD system uses a variety of therapeutic modalities, including gene, RNAi and protein therapies, to solve complex medical problems.

Novelties iMDs are smart adaptive systems that are modular, flexible, integrated and customized. They are used to apply specific customized therapeutic modalities to specific human subsystem pathologies. The system provides integrated diagnostic and therapeutics on-demand in an autonomous implantable system for solving complex diseases by combining a range of custom solutions. The iMDs are used to construct personalized solutions in real time to pathologies involving neurology, the vasculature, cancer, immunology and endocrinology.

By applying gene therapy, RNAi therapy and protein replacement therapy the system presents integrated solutions to complex problems. The system also operates to solve multiple problems simultaneously.

Advantages of the Invention

There are a number of advantages of the present invention. Analyses of biomedical problems are performed by the iMDs for rapid, efficient, precise and on-demand response. The system automatically assesses biomarkers and responds to the underlying disease. The system develops customized solutions within resource and time constraints. The system generates personalized medicines targeted to specific pathologies, which allows the management of pathologies over time. The invention diagnoses and analyses multiple attributes simultaneously, which allows the system to manage multiple diseases. The present invention is also pro-active since iMDs anticipate pathology developmental phases and act to prevent disease degradation.

DESCRIPTION OF THE INVENTION

There are five critical regulatory subsystems for which the iMD network is useful. These include:
Neurological system
Cardiovascular system
Neoplasty pathologies
Immune system
Endocrine system
The following describes the use of iMDs in these subsystems.
(I) Neurological System
(1) System for iMD Network Applied to Cerebrovascular Diseases Cerebrovascular diseases include hemorrhagic stroke, ischemic stroke, concussion and migraine headaches. In most cases, the iMD is installed in the chest, with catheters running up the carotid artery (left or right0 for access to the cerebrovascular system. Drugs are then provided to respond to specific disorders.

In the case of hemorrhagic stroke, subarachnoid hemorrhage is typically caused by an aneurysm (bulging blood vessel). Aneurysms can be caused by hypertension or by genetic anomaly. In the case of aneurysms, iMDs are used to send probes (with inflatable balloons or with micro- and nano-devices) to fill up (that is, block, clamp or cut off part of) the aneurysm and prevent blood from entering. With subarachnoid or intracerebral hemorrhage, the iMD detects the stroke (by detecting a change in blood pressure and blood flow), identifies the location of the bleeding and administers blood coagulants to stop the bleeding. Because micro-hemorrhages are fairly common in some patients, the iMD establishes an adjustable threshold for activating the coagulant therapy. The iMD then evaluates the response to the therapy and modulates the drug accordingly. For hemorrhagic strokes, the iMD also administers pain medication.

In the case of ischemic stroke, the iMD is activated by detection of the blockage of an artery. In this case, the iMD administers tissue phasminogen activator (TPA) to the patient. Because less than five percent of patients receive TPA within the effective time (3-4 hours) range, the use of iMDs to administer the drug in high risk patients during stroke episode is a major advancement. Ischemic stroke patients are tracked for biomarkers that indicate risk levels for stroke. IMD's model the stroke patient's conditions for the disease progression and risk profile in order to anticipate the probabilities for stroke.

Because ischemic stroke is caused by atherosclerotic clot or a blood clot in a brain blood vessel, the delivery of TPA is made possible by using the iMD in either of three ways. First, the TPA is administered as a drug in the blood stream. Second, the TPA is administered by using micro- or nano-devices that move directly to the clot to administer the drug. Third, the iMD sends a catheter directly to the clot and administers the TPA. The second and third approaches require the development of a map to identify the direct location of the clot. This map is constructed by using advanced imaging technologies or by using the nanodevices, which move through the system and record the condition of the pathways.

In some cases, the iMDs are used to coordinate the implantation of a stent in the blood vessels of the brain, particularly in minor arteries that are difficult to reach by surgery. In other cases, the stents behave as satellites to the iMD system and contain intelligent components, including compartments that contain medications that are administered on demand and probes that routinely identify biomarkers that are precursors to activation of an event. This therapy is generally used in cases of repeated strokes to address the affected area.

IMDs are useful for analysis of neurovascular conditions that predict the probabilities of stroke. The iMDs collect biomarker samples and analyze the patient's blood chemistry and blood pressure to develop an evolving model of the patient's condition. The main aim of the model is to anticipate disease progression and administer drugs that prevent advanced disease states.

In the case of migraine headaches or concussion, the iMDs administer a nonsteroidal anti-inflammatory drug (NSAID) or triptans.

(2) System for iMD Network for Modulating Central Nervous System

IMDs are applied to pathologies associated with the CNS. In particular, iMDs are useful in modulating pain, epilepsy and spinal cord pathologies. In the case of pain, the iMDs administer and regulate pain medications, gradually removing the opiates as the patient condition improves.

In the case of epilepsy, an iMD is placed in the chest under the collar bone to regulate electrical functions of the patient by using wires that are connected to the vagus nerve (between the brain and the heart). In addition, other iMDs administer epilepsy drugs on demand as the device identifies biomarkers that indicate a seizure is imminent. The iMDs develop models of the seizure patterns; from these models, the iMDs anticipate the seizure activity and administer a drug when specific factors are present that foresee an episode.

Spinal cord injuries are addressed by iMDs. Once trauma occurs to the spinal cord, the iMD system is installed in the abdomen or chest. The iMD system applies three therapeutic regimens. First, the iMD is connected to the affected spinal cord region to apply anti-inflammatory drugs to limit swelling. The patient is also provided with pain medication. Second, as the swelling of the traumatized region diminishes, the iMD applies stem cells that immediately fortify the lost tissue. Third, the iMD attaches nanowires to the spinal cord bypassing the injury site and connecting the nerve tissues like a bridge. When the stem cells fortify the nerve cells in the region, the nanowires are removed.

(3) System for iMD Network for Modulating Psychiatric Disorders

IMDs are useful for modulating various psychiatric disorders. First, the iMDs are used to diagnose specific dysfunctions. The iMDs identify biomarkers and access databases to compare the biomarkers to specific psychiatric conditions. Specifically, the iMDs address medical conditions associated with depression, obsessive compulsive disorders, sleep disorders, schizophrenia, bipolar disorders and addiction. In some cases, these psychiatric conditions immobilize a patient and require a careful modulation of brain chemistry.

In the case of bipolar affective disorder (BAD), the iMD identifies BAD associated protein isoforms before initiating the clinical remedy. Discovery of this biomarker stimulates a cascade of functional responses in the iMD network to modulate the brain chemistry.

The iMD continuously monitors the brain chemistry of patients and identifies biomarkers that indicate onset of an abnormal condition. The iMD then applies medicine(s) to regulate the patient's blood chemistry. The iMD assesses the effects of the application of medicine(s) and adjusts the medicine. As a specific episode passes, the iMD modulates or removes the medicine(s).

One advantage of using the iMD system is that it analyzes multiple variables that indicate multiple maladies that are simultaneously addressed. As a consequence of addressing multiple problems, however, the iMD is required to assess the combination of drug interactions. The major problems associated with administering effective psychiatric remedies is in the identification of the combination of drugs needed, the interactions that require pruning and the timing of their use. The iMD system is used to successfully assess the patient's changing brain chemistry and to integrate diagnoses with therapeutic modalities. IMDs are placed in the chest, with tubes to administer the drugs placed in the chest and/or brain depending on the condition. This system is useful in the most difficult cases in which dosing and chemistry combination synchronization are challenges.

Because psychiatric disorders typically have a genetic component, it is possible to introduce gene therapy to improve the condition of psychiatric patients. IMDs are used to facilitate and modulate the gene therapy modalities.

One advantage of the iMD system in treating psychiatric disorders is the ability to overcome the blood brain barrier (BBB) in the delivery of chemicals because it uses several different therapeutic methods.

(4) System for iMD Network for Modulating Remedies for Neurodegenerative Diseases In addition to the neuro-degeneration associated with aging, Alzheimer's disease, Parkinson's disease and Huntington's disease are debilitating disorders that require complex remedies. Multiple sclerosis is also a debilitating neurodegenerative disease. There are genetic components of MS, Alzheimer's, Parkinson's and Huntington's. Huntington's is a polyglutamine disease. The iMD is used to identify biomarkers that recognize the absence or presence of particular proteins. In some cases, the common malady in these neurodegenerative disorders is the death of brain cells. While direct application of drugs by iMDs to treat symptoms is useful, they typically do not address the causes of these problems.

IMDs are useful in providing protein therapy to replace specific dysfunctional proteins in specific regions of the brain. The iMDs employ a derivative of gene therapy to target specific neurological tissues by using probes.

While iMDs will not cure the diseases when cell death has occurred, it is able to control the decline by modulating the brain chemistry to reduce the rate of cell death.

Regarding the problem of the death of brain cells that cause neurodegenerative diseases, the iMDs use probes to identify and map the affected region. The iMDs then request the insertion of stem cells to these regions by utilizing connected catheters. Using probes to detect the progress of biomarkers, the iMDs monitor the assimilation of the stem cells and adjust the remedy. This process continues until the patient's symptoms, such as tremors or memory loss, are improving.

(II) Cardiovascular System

Cardiovascular disease is the number one cause of mortality in the Western world. While cardiovascular pathologies involve the heart muscle itself, atherosclerotic diseases include coronary heart disease (arteries of the heart itself), peripheral arterial disease (PAD) and wound healing diseases.

(5) System for iMD Network for Modulating Cardiovascular Disorders

Several cardiovascular pathologies affect overall patient health. These include arteriosclerosis and hypertension. The iMD system is useful for applying chemicals to the vascular system for treating these disorders.

Regarding arteriosclerosis (hardening of the arteries), the most common form of which is atherosclerosis (inflammatory-artery disease involving build up of plaques), is caused by the accumulation of white blood cells and low density lipoproteins (LDL) in the arteries. The resulting accumulation of plaque affects the ability of arteries to promote the flow of blood. In later phases of the disease, calcium forms on the valves of the heart and clots break off from the inner arterial linings. Statins are routinely used to inhibit the enzyme HMG-CoA reductase, which affects the mevalonate pathway for cholesterol synthesis; statins stimulate LDL receptors for enhanced clearance of LDL from the bloodstream, with the effect of less arterial plaque accumulation.

IMDs are useful in administering drugs to control the debilitating lipoprotein accumulation and its atrophic and oxygen deprivation consequences. IMDs identify biomarkers, such as cardio reactive protein (CRP) and lipoprotein types and levels, to assess the patient's general condition. The iMDs then send out nano probes to map the patient's vasculature to identify the locations for plaque and the arterial calcification at these locations. The nanoprobes record the specific locations of the greatest buildup of plaque and return to the iMD. The iMD generates a model to map the vasculature. Specific proteins are used to identify vascular "zip codes" that differentiate locations in the vascular system; use of these proteins direct drugs and nanodevices to these specific locations.

There are several strategies for therapeutic angiogenesis to repair diseased blood vessels. IMDs are used to apply protein therapy to affected vascular regions. IMDs use probes and nanodevices to apply vascular endothelial growth factor (VEGF) and fibroblast growth factor 1 (FGF-1) to specific cell clusters to affect the growth of new blood vessels. Additional gene therapies are useful to repair the region around atrophied blood vessels.

IMDs are optimal to modulate the application of proteins in the vasculature. IMDs regulate nanodevices and probes to distribute a low level of protein kinase C-epsilon (PKC-E) to promote cardio-protection.

The iMDs are implanted in the chest near critical arteries, with catheters extending to the inferior mesenteric artery, the external carotid artery and the subclavian artery.

Nanoprobes are themselves used by the iMD to apply medicines directly to affected regions. Further, when plaque has built up to a degree that will create a clot, the nanoprobes behave like high density lipoproteins and remove the plaque.

(6) System for iMD Network for Hematological Filtration Process

There are a number of medical conditions which require a change in blood chemistry to maintain a patient's health. These conditions include poisoning, infection and a deficiency in white blood cells. In addition, genetic hematological disorders require intervention, including hemophilia and sickle cell anemia. Finally, there are pathologies that require blood transfusions, including severe anemia (deficiency of hemoglobin) and thrombocytopenia (too few red blood cell platelets). The iMD system processes hematological functions by filtering the blood.

IMDs are connected to specific arteries by catheters. After biomarkers are discovered that diagnose the pathology, the iMDs filter out the exogenous elements (poison or infection) from the blood by using multiple chambers to screen the elements. The screens filter the abnormalities while allowing the red blood cells, white blood cells and the antibodies through.

Sickle cell anemia and hemophilia are genetic diseases that require the insertion of proteins into the patient's blood cells. Regarding sickle cell anemia, the iMDs first perform protein replacement therapy to generate healthy red blood cells and then engages the filtration process to remove the sickle shaped cells as they are replaced with healthy cells. IMDs treat hemophilia by applying coagulants to treat the symptoms, but engage in a protein replacement therapy to generate healthy red blood cells.

Anemia and thrombocytopenia are also treated with filtration and protein replacement therapy. Because red blood cells survive on average 120 days, this process must be repeated every sixty days in order to preserve the continuity of the new blood cells.

(7) Method for Blood Cell Supplementation using iMD for Blood Loss Trauma

Blood loss is a leading cause of death from trauma. In many accidents or combat environments, the challenge is to replace lost blood to preserve the oxygenation of tissues. IMDs are used to supplement blood loss in critical situations. External iMDs hold multiple liters of blood, filtered by type (to prevent immune system overreaction), to supplement blood loss from bleeding. The internal iMD network connects the external fresh blood reservoir directly to arteries with catheters.

In an alternative embodiment, the iMD network behaves as an oxygen generator and filters the blood to add oxygen on demand. This process requires access to an external iMD that supplies the oxygen.

These applications of the iMD to supplement blood and oxygen are intended to be temporary remedies and are used in conjunction with critical care services.

In an additional application, iMDs are used to drain fluids from the lungs by installing tubes that evacuate fluids to external reservoirs.

(III) Cancer

Cancer has genetic components that manifest in uncontrolled cell growth (neoplasties). Cancer tumors are abnormal cells that generate from a combination of genetic mutations. The mutated genes create dysfunctional proteins that upset the protein regulatory networks of cells and stop regular cell cycle circuitry. While all tissues are susceptible to cancer, the iMDs are used to target neoplasties involving lung, brain, skin, liver, pancreas, colo-rectal, leukemia, lymphoma, breast and prostate, among the most common and deadly cancers. As researchers build libraries of data on the genes and proteins that cause cancers, it is increasingly possible to target specific gene complexes with combination therapies. IMDs are useful in implementing several of these strategies.

(8) System for iMD network for targeted non-invasive chemotherapy and radiation

IMDs are used to target chemicals and radiation directly to tumors. These two therapeutic modalities represent a major element in cancer treatment, but have high risks of harming healthy tissues and their consequences. The challenge is to develop methods to precisely target specific tumors with chemotherapy drugs or with radiation and to leave surrounding cells intact.

After first collecting biomarkers that detect the presence of cancer cells, the IMDs develop a model to identify the precise location of the tumors. The iMDs send a probe to the location to collect a sample from the tumor cells for analysis. The iMDs then analyze the cancer cells for genetic mutations. Information about mutations is useful to define the tolerance parameters for predicting the outcome of chemotherapy or radiation. The iMDs update the model of the tumors based on available information.

The iMDs send out nanodevices laden with specific drugs to the tumors. The nanodevices are coated in a TK-receptor protein that allows them to attach to the cancer cells. Once inside the cells, the chemotherapy drugs kill the tumor. Antibodies from the human immune system then identify and attack the remaining tumors as antigens.

In some cases, the nanodevices are specifically irradiated. The radioactive isotopes carried by the nanodevices are directed to the tumors and kill the tumor cells. Antibodies from the human immune system then attack the remaining tumors as antigens and remove the irradiated nanodevices. The clear advantage of the irradiated nanodevices is to precisely target cells without harming the surrounding tissue.

(9) System for iMD Network Applied to Cancer Metastases

If cancer cells remained in one place, then it would be possible to remove the tumors and cure the patient. However, most patients die after the cancer spreads to other tissue. if this process of metastases can be controlled, then this fundamental component of cancer would be restricted. One of the problems of metastases, however, is that cancers affecting specific tissues in the gastro-intestinal tract and the lungs require blood flow that tends to spread the cancer cells to other parts of the body. The challenge is to find ways to identify the metasticized cancer cells or to control their spread.

While the human immune system is critical in destroying cancer cells as antigens, the HIS is not effective in identifying all cells which spread. Yet, HIS antibodies are useful in tracking down metasticized cells if they are tagged by proteins or nanodevices generated by the iMDs. Once the metasticized cells are identified, various drug and radiation targeting approaches are used to attack them as well as normal HIS antibody cascade behaviors. The goal is to identify the wayward cancer cells as antigens.

In most cases, the spread of cancers occurs from one specific tissue type to another specific type of tissue. For instance, skin cancer tends to spread to lymph nodes and lung cancer tends to spread to nearby bones. Consequently, the iMDs are useful to predict these changes and to patrol these tissues searching for the metastatic cancer cells using probes. When the iMD probes identify the new cancer cells, the neoplasties are tagged for later application of drugs and radiation targeted therapies.

In another embodiment of the system, the iMD probes actually prevent the metasticization process by harvesting and filtering cells around the tumors. This is similar to establishing a blockade around a well-defined area.

(10) System for Blocking Angiogenesis in Tumors using iMDs

Tumor cells manufacture proteins, including vascular endothelial growth factor (VEGF) and fibroblast growth factor 1 (FGF-1), to generate blood vessels in order to gain access to blood vessels and oxygen. The iMD network is used to choke off the tumor angiogenesis network. This process works in a similar manner to constraining an aneurism, or abnormal blood vessel. The iMD sends out probes to the cancer tumor. The probes identify the new blood vessel bridges created by the tumor to sustain blood supply. The probes then perform one of two procedures.

First, the probes apply a carbon alloy micro-clip to the angiogenesis site to crimp and close it off from the outside of the vessel. The micro-clip is coated with protease inhibitors to starve the vessel of proteins to regenerate. Second, the probes insert into the vessel VEGF and FGF-1 blocker coated carbon alloy or platinum coils. The burrowed coils expand in the blood vessels and choke off the blood supply while also treating the endothelial cell wall of the vessels with protein inhibitors. The effect of either method is the constriction of the vessel and the cutting off of blood supply to the tumor.

The system works with sprouting angiogenesis and with intussusceptive (splitting) angiogenesis. Other growth factors, proteins and inhibitors are added to the devices in order to stop cell growth of tumor blood vessels.

(IV) Gene therapies

Cancer is caused by genetic mutations or single nucleotide polymorphisms (SNPs). Mutated genes generate dysfunctional proteins that manifest as pathology in the protein regulatory networks. In most cases, the mutated genes inhibit critical proteins that regulate the growth and death of cells.

Neoplasties are specific cancer cell clusters that result from a combination of genetic mutations. Each tumor type contains a different combination of mutations. Therefore, the discovery of the specific unique combination of gene mutations, and the nature of the mutations, reveals the precise source of the pathology. If the problems of cancer are to be solved, it is necessary to develop clinical ways to identify the precise genetic combinations that cause each unique cancer type as well as to identify therapeutic regimens that yield benefits at the cellular and genetic levels.

Interestingly, it is evident that specific master genes regulate the gene networks. An example of this is the p53 gene that regulates cancer by stimulating a gene to produce a protein p21, which interacts with a cell division stimulating protein (cdk2). When p21 is combined with cdk2, the cell does not divide. A mutated form of the p53 gene no longer binds DNA, which inhibits the production of p21, which in turn does not block the cell division process. Affected cells therefore divide without cell death and manifest as neoplasties. Therefore, targeting the master gene is critical to control the whole regulatory process.

Gene therapy is the therapeutic model of inserting genes into a patient's cells to replace the mutated genes. Even after the precise set of problematic genes are identified, which is performed by micro-array analyses and the comparison with cancer gene databases, there are several critical problems that need to be overcome in order to implement an effective gene therapy. These problems are overcome by using the iMD system.

First, there is the problem of precisely targeting the affected cells.

Second, there is the problem of penetrating the cells. How can we get beyond the cell's natural defenses that consist of proteins on the cell surface? This requires a way to engineer proteins to inhibit the tyrosine kinase receptors (TKRs) on the cell surface.

Third, there is the problem of finding the precise place to target the gene(s). Even if the gene therapy penetrates a cell, there is a need to identify the precise chromosome and gene locations.

Fourth, there is the problem of preventing an immune response to foreign material by the host. How can we trick the immune system not to attack inserted material?

Fifth, there is the problem that even if it works, the model is limited only to one cell cycle, which requires the procedure to be periodically repeated.

The same methods that are applied to gene therapy are also applied to protein therapy and to RNA interference that blocks genes. The immune system is a major actor in gene therapies, requiring strategies that involve its operation or suppression.

The application of iMD processes to gene, RNAi and protein replacement therapies represents an active example of personalized medicine. In each case, individualized medical procedures and drugs are identified and targeted to specific tissues to solve specific problems.

(11) Methods for Targeting Tumors for Gene Replacement using iMDs

Gene replacement is referred to as "magic bullet" therapy. The idea seems straightforward. Carry a new set of genes to cells to reconstitute the DNA to the state of healthy cells. However, the challenges are daunting. In general, gene therapies use viruses to carry oligonucleotide sequences to penetrate into the nuclei of cells where the sequences repair the mutated gene(s) and restore cellular functionality. An adenovirus is stripped of its infectious genetic material, while engineered genetic material is inserted into the virus. A native gene in the virus encodes a protein that allows the virus to insert into host cells and infect its DNA into the cell nucleus. The virus is then inserted into tissue, for example, tumor tissue, where it carries the engineered genes to the target cells.

Cellular regulatory processes and the immune system use mechanisms to reject this foreign substance model, which requires a more complex process for effective implementation. Novel gene therapy models use immune cell microRNA target sequences to turn off an immune response. Other models coat the virus with proteins or antibodies to prevent rejection by the cell surface TK receptors. In effect, these new gene targeting therapies emulate HIV by knocking out defense mechanisms to attack a cell, but remove the toxic viral components.

Viruses used for gene replacement include retroviruses, recombinant adeno associated virus (AAV) [adenoviruses] and lentiviruses. One of the most effective therapeutic approaches involve using a lentivirus simian immunodeficiency virus coated with matrix proteins from a vesicular stomatitis virus.

Because of the need to modify viruses for application as delivery vehicles for genes, RNA and/or proteins, it is necessary to "cook" the viral vectors to create a virus "tuned" to each specific targeted cell type. Specific lines of viruses are engineered with the combinations of genes and proteins and are matched to specific cell targets to improve therapeutic effectiveness.

Other models involve the combination of a virus with stem cells. In this approach, stem cells and retroviruses are combined. The engineered gene from the virus is targeted to the stem cell chromosome. The stem cell is then injected into specific tissues.

Stem cells are injected with genetically modified viruses and antibodies and with cargo carrying micro- and nanodevices for use as delivery vehicles to target specific cells. In some cases, the nanodevices carry proteins and are installed in antibodies. The antibodies are injected into viruses or stem cells, while the viruses are injected into the stem cells.

Antibodies are used to coat the viruses or the nanodevices to prevent immune response. In the ideal, a patient's own antibodies are used. The iMD system harvests antibodies and uses the captive antibodies to coat engineered viruses. This process is performed in different chambers of the diagnostic and therapeutic modules in the iMDs.

Nanodevices are also coated with antibodies and proteins. The proteins are used to gain access through the cell surface TK receptors, while the antibodies ward off immune response. Nanodevice collectives, which are contained in chambers of the iMDs, allow drugs and proteins to be carried to a specific cell. Radioactive isotopes are also carried by nanodevices to cells. Radioactive nanodevices target cells and tag them like a beacon. The engineered virus is then targeted to the nanodevice collective tag.

In general, for complex genetic networks such as cancer, the gene therapy must target a master gene that regulates other genes, like p53. Each chromosome has a "zip code" in the DNA sequence, with each gene having a postal address. Each address location is identified using specific target proteins.

Contingent of the specific tumor type, the iMD system is useful to coat engineered viruses, antibodies and nanodevices with proteins which increases the likelihood of the viruses, antibodies and nanodevices to penetrate the host cell, to find the gene location and to resist the immune system antibody patrols. The use of proteins and antibodies tricks cells to not recognize the modified viral application.

The iMD system harvests the patient's own cells and antibodies and stores the biologicals in compartments of the therapeutic module. The engineered viruses are coated with target and TK resistant proteins and with the patient's own antibodies. The engineered viruses are then installed into some of the patient's own cells and into stem cells for delivery by probes to the tumor cell site.

These combinatorial gene therapy modalities, which require interactive features that iMDs provide, are an effective approach to solving complex genetic pathologies.

(12) System for Epigenetic Applications to iMD to Cancer using RNAi Techniques

RNAi is an ancient antiviral mechanism. Each cell uses an enzyme (dicer) to break down double stranded RNA into smaller segments of about 20 nucleotide pairs in length and an enzyme complex (RNA induced silencing complex [RISC]) to use the shorter pieces to seek out and destroy single stranded RNA of the same configuration, including copies of RNA used by viruses to make viral proteins. RNA machinery also cleans up the genetic material in the nucleus by eliminated repetitive copies of nucleotide sequences.

As a method of silencing targeted genes, RNAi is used to introduce small interfering RNA (siRNA) into the genome using an engineered virus. Targeted inhibition of specific genes by engineered viral vectors removes a mutated genetic component that is actively causing creation of a protein that stimulates cancer growth. While gene therapy approaches target genes for "repair," RNAi approaches target oncogenes to block their performance.

IMDs use a similar process to target RNAi therapy to cells by employing engineered viral vectors. Rather than installing engineered genes, the RNAi process installs synthetic short double stranded RNAs (dsRNAs) or synthetic siRNA duplexes that block expression of genes. IMDs install the synthetic RNA complex into the engineered virus for installation into targeted cells.

The system employs a cocktail of combined therapeutic options that includes the preparation of the engineered virus, the addition of specific protein coatings and the inclusion of specific DNA and RNA components to target specific genes in different ways. The system is thus able to suppress some gene functions with RNAi techniques while simultaneously replacing specific dysfunctional genes. The results of the application of these combination therapies are the production of healthy proteins during the cell cycle, which manages the protein regulatory networks, with the effect of inhibiting abnormal cell growth.

(13) System for Protein Replacement of Combinations of Dysfunctional Proteins using iMDs Rather than manipulating the underlying genetic machinery in the cell, protein replacement targets specific dysfunctional proteins that are generated by mutated genes. While the gene therapeutic model stops the generation of a dysfunctional protein by repairing a specific set of genes, and RNAi blocks a gene's production of a protein, the protein replacement approach simply corrects the end product. By targeting specific proteins, the cancer tumor growth is blocked. In one example, the FMS like tyrosine kinase 3 (Flt3L) protein is combined with the herpes simplex virus type 1 thimidine kinase (HSV1-TK) protein and the antiviral gancyclovir (GCV) to kill glioblastoma multiforme (GSM) cancers. This approach has the advantage of overcoming both the blood brain barrier and the immune system antibody response.

The iMD is used to combine multiple targeted proteins which are contained in multiple compartments of the therapeutic module. The analytical modeling of the genetic mutation combination of a disease are computed by using external computation and comparison with libraries of genetic databases to identify the precise genes and proteins that require targeting for each specific pathology type. The proteins required to repair healthy regulatory network performance are then synthesized and installed in the iMD. The proteins are installed in the engineered viruses that are contained in another compartment of the iMD therapeutic module. The virus is then inserted into the target cells using navigation and targeting processes, including targeting and penetrating protein and antibody viral coatings. The iMD monitors the progress of the therapy and modifies the protein combination therapy.

(14) Method of Immunosurveillance using iMDs

One of the challenges of implementing gene therapies is overcoming the problem of antibodies that attack engineered components of cells. The humoral immune system antibodies constantly patrol cells for exogenous invasive materials and recruit antibody collectives to destroy infected cells when these materials are discovered. In theory, the immune system should identify cancer cells and destroy them. However, this foreign body identification process is dysfunctional in cases of metasticization and aging, which promulgates the effects of cancer. If tumor cells are a kind of "protected antigen," removal of the protection triggers a cascade of antibody behaviors to destroy malignant cells.

IMDs are used to identify tumors and coat them with proteins that identify them as invasive in order to trick the immune system antibodies to attack the tumors. In effect, the iMDs use probes to target tumors and mark them with antigens, which are then readily recognized and attacked by the antibodies.

Using another model, the iMDs use probes to implant a harmless but identifiable virus into tumor cells and invite the immune system antibodies to respond by swarming and killing the cells.

(V) Immune System

The human immune system (HIS) is a complex evolutionary mechanism that performs numerous critical functions, from fighting infectious diseases to controlling tumor growth. However, the immune system is also a carefully refined mechanism that frequently degrades specific components and thereby presents dysfunctions, including autoimmune disorders.

(15) System for Modeling HIS for Rapid and Moderate Viral Response using iMDs

The HIS is divided into the humoral immune system and the adaptive immune system. The humoral immune system fights infections in one of two ways: an inflammation response and an antibody collective response to infectious agents. Once a known infection is identified, the humoral antibodies tag the antigen and escalate an antibody cascade process until the antigen and its infected cells are destroyed. The adaptive immune system identifies and attacks previously unknown antigens by using B cells, T cells, NK cells and immunoglobulin antibody collectives in novel geometrical configurations to reverse engineer a solution to destroy the new antigens. The adaptive immune system then sends the solution to destroying this new antigen to the humoral immune system as a learned immunity so that when the same antigen is discovered, the humoral immune system antibody cascade process will know how to solve the problem rapidly if discovered again.

Infectious diseases include bacteria and viruses. Viruses include herpes family viruses, HIV, hepatitis, influenza, chicken pox, SARS, Ebola, swine flue, avian flu and the common cold.

The iMD system models each patient's immune system by identifying the thresholds for identification of infections and the response mechanisms for destroying antigens.

IMDs are applied to viruses in several ways. In one application of the iMD system to immunological operations, the system uses RNAi procedures to knock out production of infectious agent proteins. Second, once the iMD system identifies the components of the virus, it applies a protein or combination of peptides that inhibit the viral infectious component. Third, the iMDs use the gene therapy model to insert a gene to disable the infectious viral genes. The gene therapy, protein therapy and RNAi approaches use the patient immune system's own antibodies to delivery the genetic and protein components. The challenge is to identify the precise combination of proteins to tune to the frequency to penetrate each virus. Once inside, one of the techniques is applied to alter the genetic structure to stop toxicity.

In another model in which the iMD is immunologically useful, it enhances the host's antibodies to attack a virus. This is done by accelerating the antibody process by triggering a cascade reaction at an earlier threshold—similar to application of a vaccine—by activating a protein that stimulates the reaction. In another model, the iMD releases mild antigens to stimulate the humoral immune system response with antibody cascades when a virus is discovered so as to accelerate the cascade process.

The iMD system is installed at several locations near lymph nodes in order to facilitate immune responses, including near the superficial cervical lymph nodes and the subclavical lymph nodes. The iMD system uses nanoprobes to move through the lymph and circulatory systems to track and modify immune system components. The iMD system also uses probes to connect to bones, particularly the hips, to modulate production of immunological cells.

(16) System for Activating and Modulating Antibody Cascade Process using iMDs

The immune system is in delicate balance. When it is out of balance, it does not respond fast enough to antigens or it responds too quickly or too intensely to false antigens. Also, the immune system does not identify the correct antigens and rather attacks the host's own cells. This phenomenon explains diseases such as allergies, arthritis and lupus. Finally, organ rejection is a problem since the immune system attacks the artificial replacement as a foreign body.

The iMD system is used to regulate the immune system by modulating the proteins that trigger a response to antigens. In effect, the specific autoimmune diseases are "tuned" by the iMD system by carefully targeting each disease.

The iMD system uses mobile nanoprobes to patrol the circulatory system. The iMD also filters specific antibodies, T cells, B cells and NK cells for periodic analysis.

When immune system cell components are weakened, the system is dysfunctional. The iMD system identifies the health of these cells and, in extreme conditions, provides protein and gene replacement therapies to fortify specific cells.

By using the iMD modeling process, the iMD anticipates the immune response to specific antigens. When an antigen is detected, the iMD stimulates the immune system to accelerate a antibody cascade response so as to rapidly defeat the antigen.

In the case of organ rejection, the iMD system works to reduce the antibodies by filtering the antibodies from the blood stream. The antibodies are collected for later use in the therapeutic module. In addition, the iMD coats the implanted organ with proteins that do not motivate an adverse immune response.

(VI) Endocrinological System

(17) System for iMD Network to Solve Endocrinological Metabolic Disorders with iMDs.

The endocrine system is a complex network of glands in the head, neck, chest and abdomen that generates and regulates hormones. The endocrine system is comprised of the hypothalamus and pituitary gland, the pineal gland, the thyroid gland, the pancreas, the adrenal gland and, in women, the ovaries and in men, the testes. The following describes the hormones created by each gland:

Hypothalamus and pituitary gland:

Vasopressin, oxytocin, thyrotropin, prolactin, growth hormone, adrenocorticotropic hormone (ACTH), luteinizing hormone and follicle-stimulating hormone Pineal gland:

Melatonin

Thyroid gland:

Thyroxin, triiodothyronine, calcitonin and parathyroid

Pancreas:

Insulin, glucagon and somatastatin

Adrenal gland:

The adrenal cortex produces adrenocortical hormones, aldosterone, cortisone and androgen (males) and the adrenal medulla produces adrenal medullary hormones, adrenaline (epinephrine) and noradrenaline (norepinephrine).

Ovary:

Estrogen, progesterone and relaxin

Testes:

Testosterone

Careful regulation of the endocrine system is important to solving metabolic disorders, including obesity, hyperlipidemia and polyglandular deficiency syndromes.

The iMD system is well suited to addressing endocrinological disorders because it is used to integrate diagnosis, therapeutics and regulation of pathology. The complex nature of the endocrine disorders suggests that the modulation of endocrine network dynamics is critical. By virtue of being on-site, the iMD system is able to constantly adjust the network of hormones by balancing hormone chemistry in real time. The iMDs are placed near the adrenal glands, the pancreas, the thyroid and, for women, the ovaries.

(18) Method for Modulating Hormones with iMDs

As the iMD system identifies imbalances, it stimulates the production of a hormone by each gland by producing a protein that activates or deactivates hormone secretion. Alternatively, the iMD produces an artificial hormone by releasing it from a compartment in the therapeutic module.

The fine tuning of the system occurs by integrating the iMDs therapeutic module with the diagnostic module. The diagnostic module constantly tracks the patient's metabolic functions and hormone levels.

In one application of the iMD system, the system provides insulin at regular intervals to modulate and regulate insulin levels.

In another application of the iMD system, the system is used to modulate the effects of menopause by supplying regular doses of estrogen and progesterone.

In extreme cases, the iMD system is used as an artificial endocrine system. In this, specific diseased glands are deactivated and the iMD system is required to supply regular hormone replacement therapies tailored to each individual.

In another embodiment, the iMD system performs experiments to analyze the patient's balanced hormone levels by adjusting specific hormone levels and assessing the results. "Hormone silencing" is a technique the iMD uses to assess variables in the complex endocrine system, and to periodically block production of a hormone, so as to identify the correct combination of hormones or to assess an imbalance. Particularly because hormone secretion occurs rapidly during specific episodes, the iMD is uniquely suited to perform multivariate analyses.

In order to perform the diagnoses, assessment and modulation processes, the iMD system uses hybrid metaheuristics to analyze the optimization problems associated with endocrine diagnoses.

Furthermore, the iMD system uses its diagnostic and analytical modeling processes to anticipate endocrinological behaviors. These models generate scenarios within probabilistic ranges based on patterns of past behaviors. The iMD system model anticipates regular endocrine system performance and provides hormone replacement to calibrate and regulate hormone levels. The ability to generate predictions of endocrinological changes allows the iMD system to develop a rapid reaction to actual changes in hormone levels and to balance and modulate these levels.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DESCRIPTION OF THE DRAWINGS

FIG. 43 is a schematic diagram showing the use of an iMD applied to RNAi therapy to disable virus genes and proteins in the HIS.

FIG. 44 is a flow chart describing the process of using an iMD for protein therapy against a viral infection.

FIG. 45 is flow chart describing the process of using an iMD for gene therapy against a viral infection.

FIG. 46 is a flow chart describing the process of using an iMD to enhance host antibody reaction to a virus.

FIG. 57 is a table of cancer genes applied to specific cancer types that are addressed by the iMD to solve cancer pathologies.

FIG. 58 is a table describing the different configurations of cell, virus and protein types applied to solving pathologies using iMDs.

DETAILED DESCRIPTION OF THE DRAWINGS

The iMD system is used for solving several complex pathologies. In particular, iMDs are applied to diseases involving neurological, cardiological, cancer, immunological and endocrinological disorders. Because it solves complex problems with customized solutions and because it is interactive, the iMD system is well suited to solving systemic medical problems.

FIGS. 1 to 17 describe the use of iMDs with neurological conditions. FIGS. 18 to 24 describe iMDs for cardiological conditions. FIGS. 15 to 41 and 57 describe the use of iMDs for cancer. FIGS. 42 to 50 describe the use of iMDs for application to the immune system. FIGS. 51 to 56 describe the use of iMDs for endocrinological conditions. FIG. 58 applies to all systems.

Figure 1:
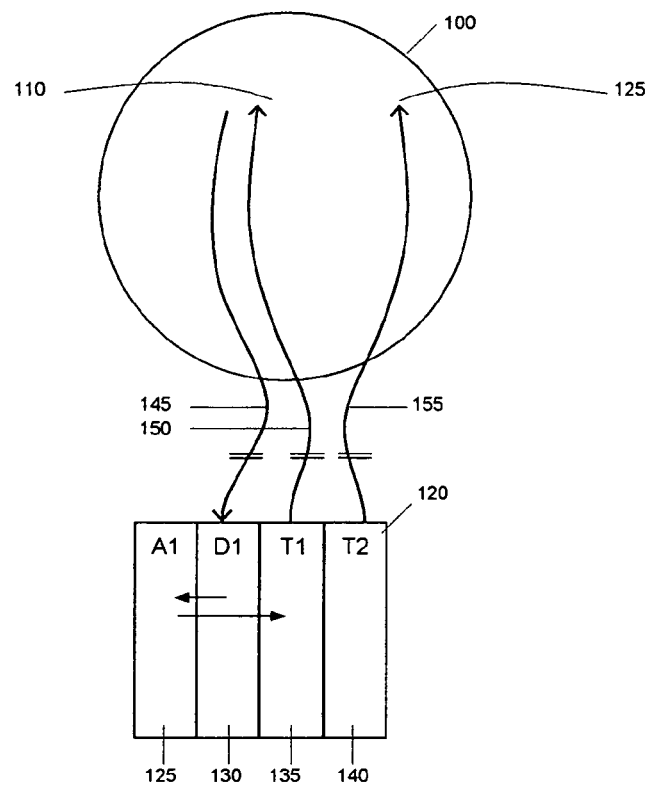
FIG. 1 is a schematic diagram showing an iMD interacting with probes in a human brain.

FIG. 1 shows an iMD interacting with probes in a human brain. The probes are used to collect cell samples for and deliver remedies from the iMD (120). In this example, cell samples are collected (145) from the location at 110 for analysis in the LOC and μTAS of the diagnostic module (130). The data are transferred from the diagnostic module to the analytical module (125) for modeling. The solution options from the model are transmitted to the therapeutic modules (135 and 140), which configure remedies and apply (150 and 155) the remedies to the cell site at 110 and a new cell site at 115 in the brain (100). Limited functional small iMDs are applied to locations in the brain and work in conjunction with multifunctional thoracic iMDs.

Figure 2:
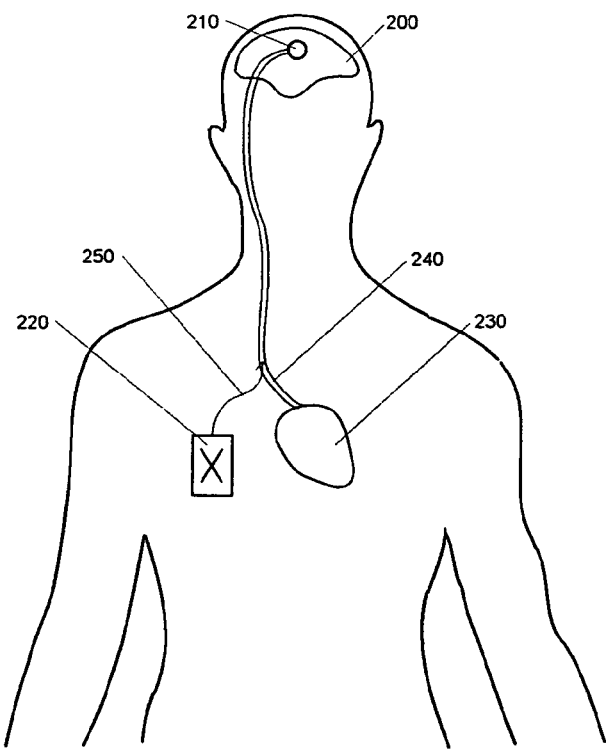
FIG. 2 is a schematic diagram showing probes sent from an iMD to the right carotid artery into the brain.

FIG. 2 shows probes sent from an iMD to the right carotid artery into the brain. The iMD (220) sends a probe (250) into the artery (240) for placement in the brain (200) at 210. In another embodiment, iMD satellites are installed in specific locations of the brain. The iMD satellites, which tend to have limited functionality, but are nonintrusive, are networked with multifunctional iMDs.

Figure 3:
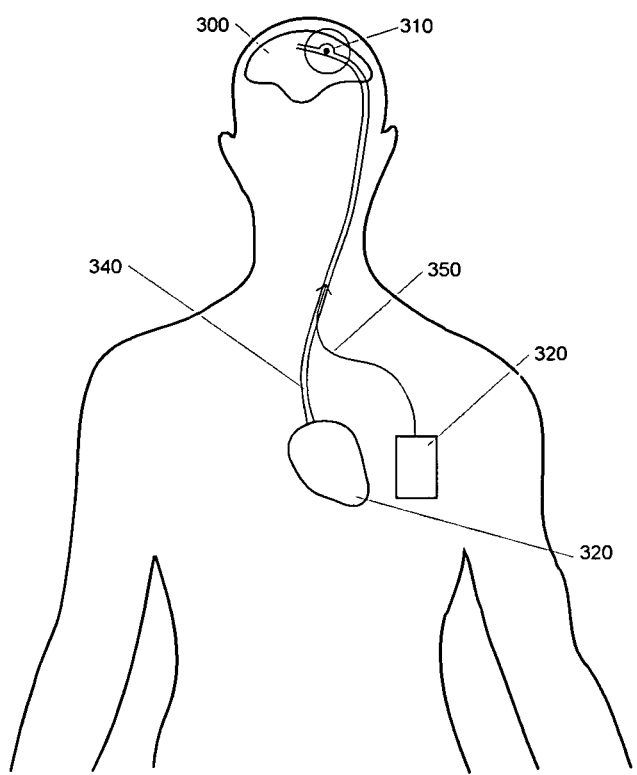
FIG. 3 is a schematic diagram showing an iMD sending probes to detect an aneurysm and an inflatable balloon to treat the aneurysm.
Figure 4:
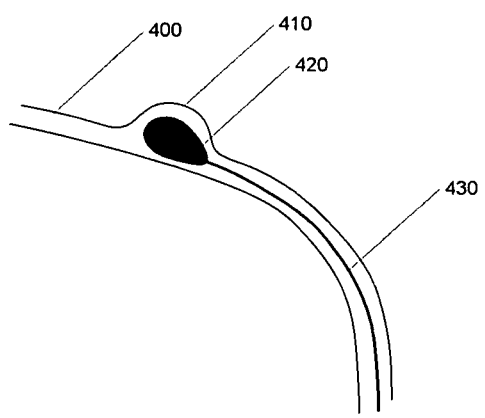
FIG. 4 is a drawing of a close up of the process of installing the inflatable balloon in the aneurysm.

FIG. 3 shows an iMD sending probes to detect an aneurysm and an inflatable balloon to treat the aneurysm. The iMD (320) sends a probe (350) to the site of the aneurysm (310) for diagnosis and treatment. FIG. 4 is a close up of the process of installing an inflatable balloon (420) in the aneurysm (410). The probe (430) is sent by the iMD through the artery (400). An alternative remedy to the use of an inflatable balloon is the use of expandable coils to fit into the aneurysm. In the case of a pre-rupture aneurysm, the balloon or the coils will fill a part of the bubble created by the aneurysm to allow blood flow but constrain risk of bursting. In the case of a post-rupture aneurysm, or bleeding aneurysm, the balloon or coils will stop the blood flow on the wall of the rupture while maintaining arterial blood flow.

Figure 5:
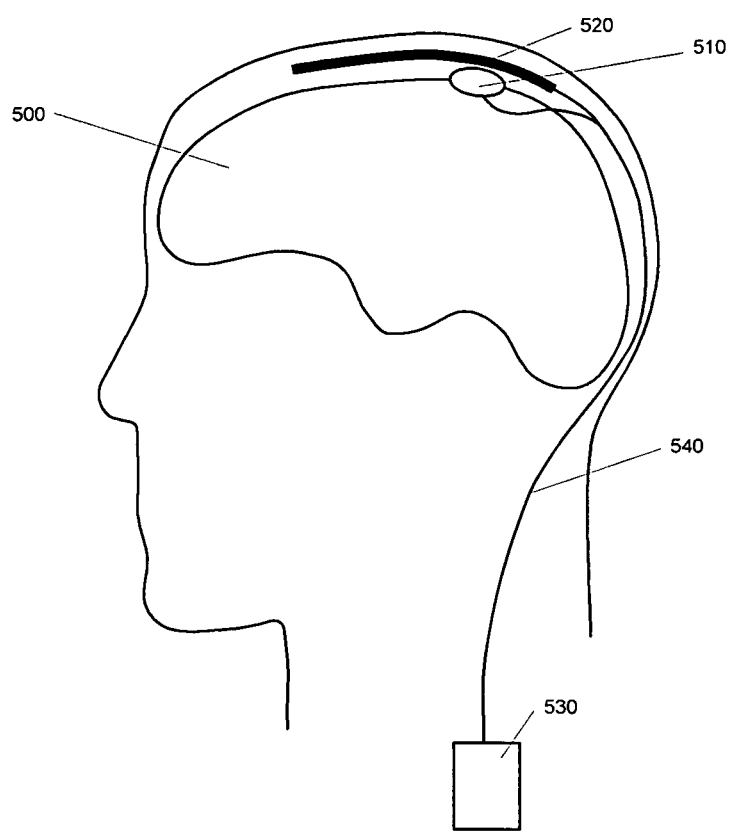
FIG. 5 is a schematic diagram showing a subarachnoid hemorrhage and an iMD sending a probe to apply a coagulant therapy.

FIG. 5 shows a subarachnoid hemorrhage (520) and an iMD (530) sending (540) a probe (510) to apply a coagulant therapy. By addressing the rupture, the rate of the flow of blood in the hemorrhage is substantially diminished by the treatment. In another embodiment of the invention, the excess blood between the brain and the skull is filtered and drained by the application of a bucket brigade model of probes that collect blood and return to the iMD. The iMD removes the excess blood to external devices.

Figure 6:
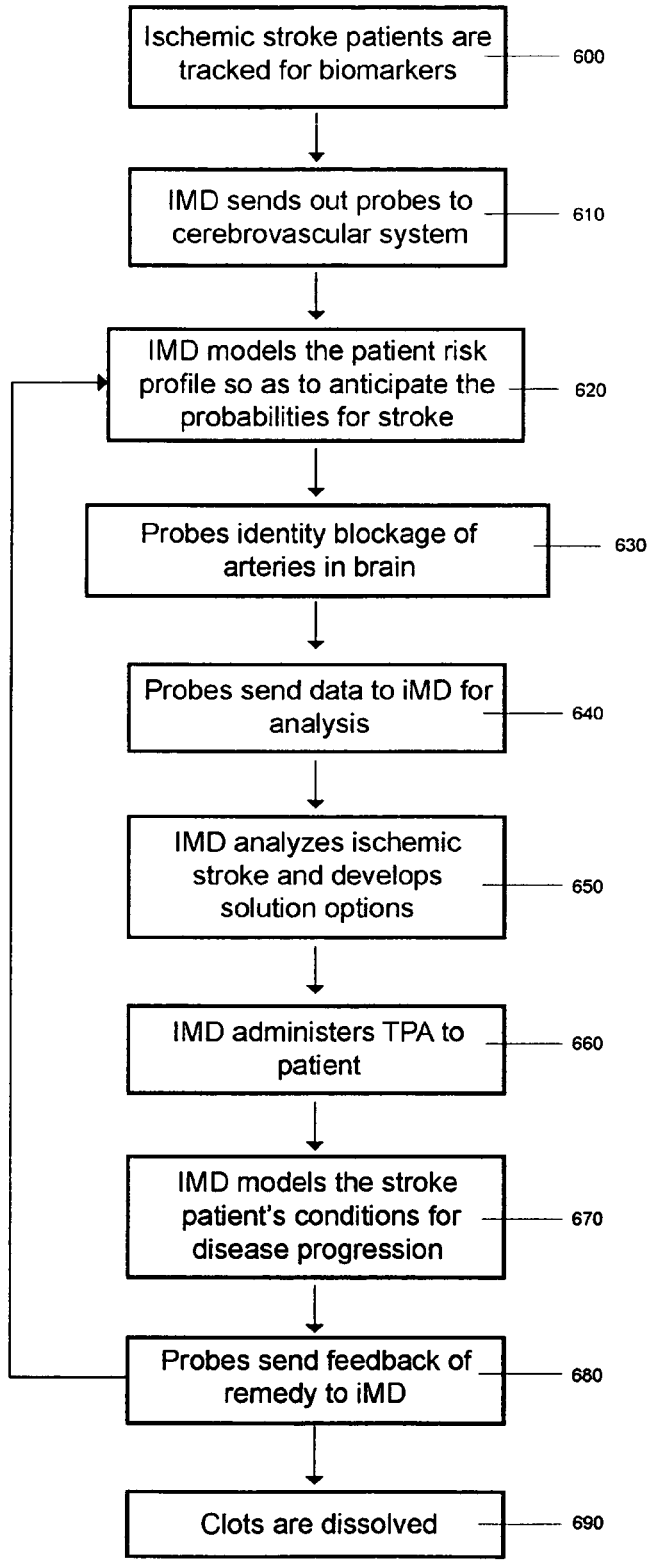
FIG. 6 is a flow chart describing the process of an iMD dispatching probes to the cerebrovascular system to treat an ischemic stroke.

FIG. 6 shows the process of an iMD dispatching probes to the cerebrovascular system to treat an ischemic stroke. After ischemic stroke patients are tracked for biomarkers (600), the iMD sends out probes to cerebrovascular system (610). The iMD then models the patient risk profile so as to estimate and anticipate the probabilities for stroke (620). The probes identify blockage of arteries in the brain (630) and send data to the iMD for analysis (640). The iMD analyses the ischemic stroke profile, develops solution options (650) and then administers TPA to the patient (660). The iMD models the stroke patient's conditions for disease progression (670) and probes send feedback of the remedy to the iMD (680). The process repeats as the probes identify more blockage. The clots are then dissolved (690).

Figure 7:
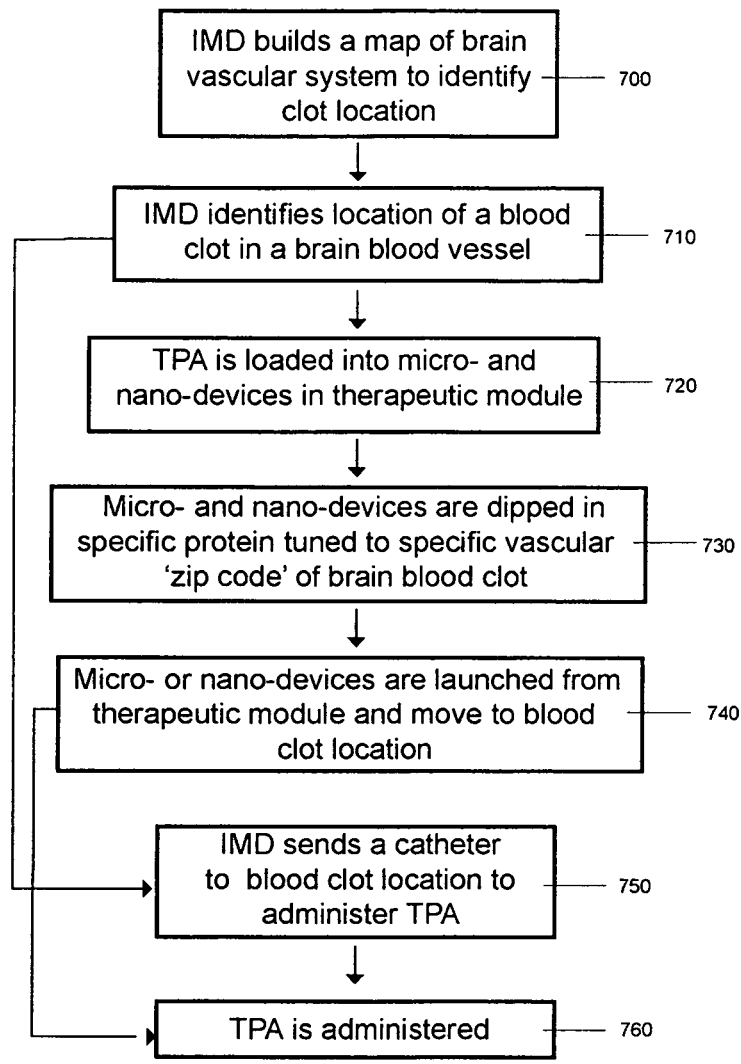
FIG. 7 is a flow chart describing the process of an iMD administering TPA to treat cerebrovascular blood clots in a particular location of the brain.

FIG. 7 shows the process of an iMD administering TPA to treat cerebrovascular blood clots in a particular location of the brain. Once the iMD builds a map of the patient's vascular system to identify the clot(s) location (700), the iMD identifies the location of a blood clot in a brain blood vessel (710). TPA is loaded into nanodevices in the therapeutic module (720) and nanodevices are dipped in specific protein "tuned" to specific vascular 'zip code' of the brain blood clot(s) (730). The nanodevices are launched from the therapeutic module and move to the blood clot(s) location(s) (740). At the same time as the nanodevices are organized to deliver TPA to the clot(s), the iMD sends a catheter to the blood clot(s) location to administer TPA (750) and the TPA is ultimately administered (760). In another embodiment, alternatives to TPA may be used.

Figure 8:
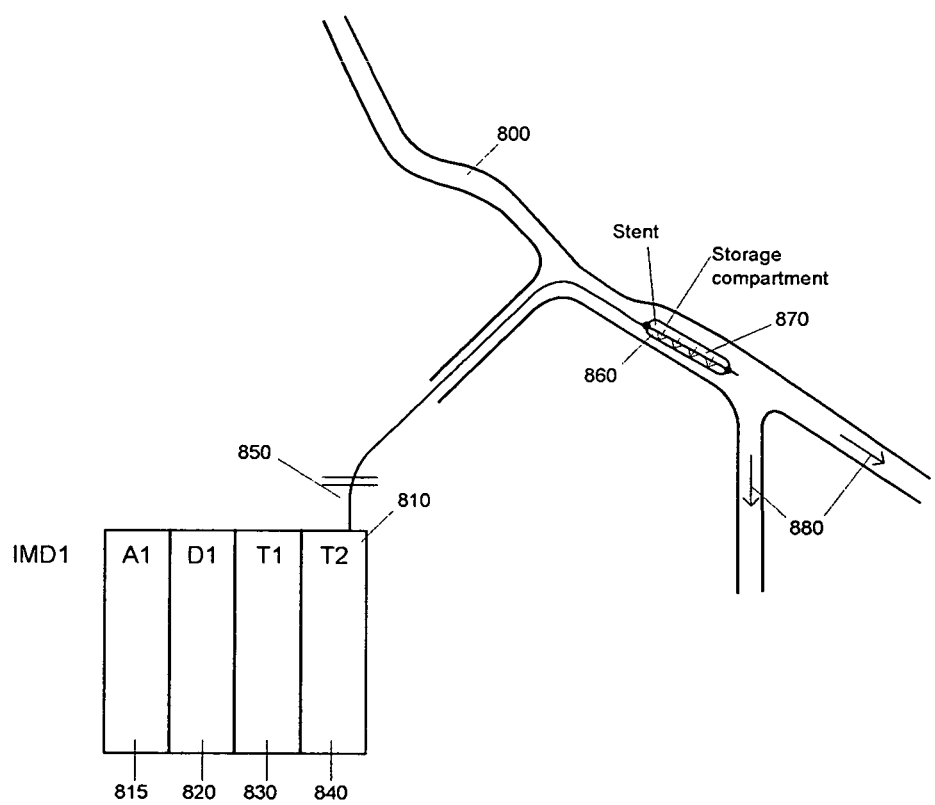
FIG. 8 is a schematic diagram showing an iMD interacting with a stent satellite.

FIG. 8 shows an iMD interacting with a stent satellite device. In the example in the drawing, therapeutic module 2 (840) of the iMD (810) installs a connection to a stent (860) in the vasculature. The stent contains a storage compartment (870). The iMD is able to supply and resupply drugs to the compartment of the stent. The stent then applies the drug(s) as needed.

The stent may be applied to arteries in the brain. Because they are applicable to the brain vasculature, the stents act as satellite devices, with limited functionality.

Figure 9:
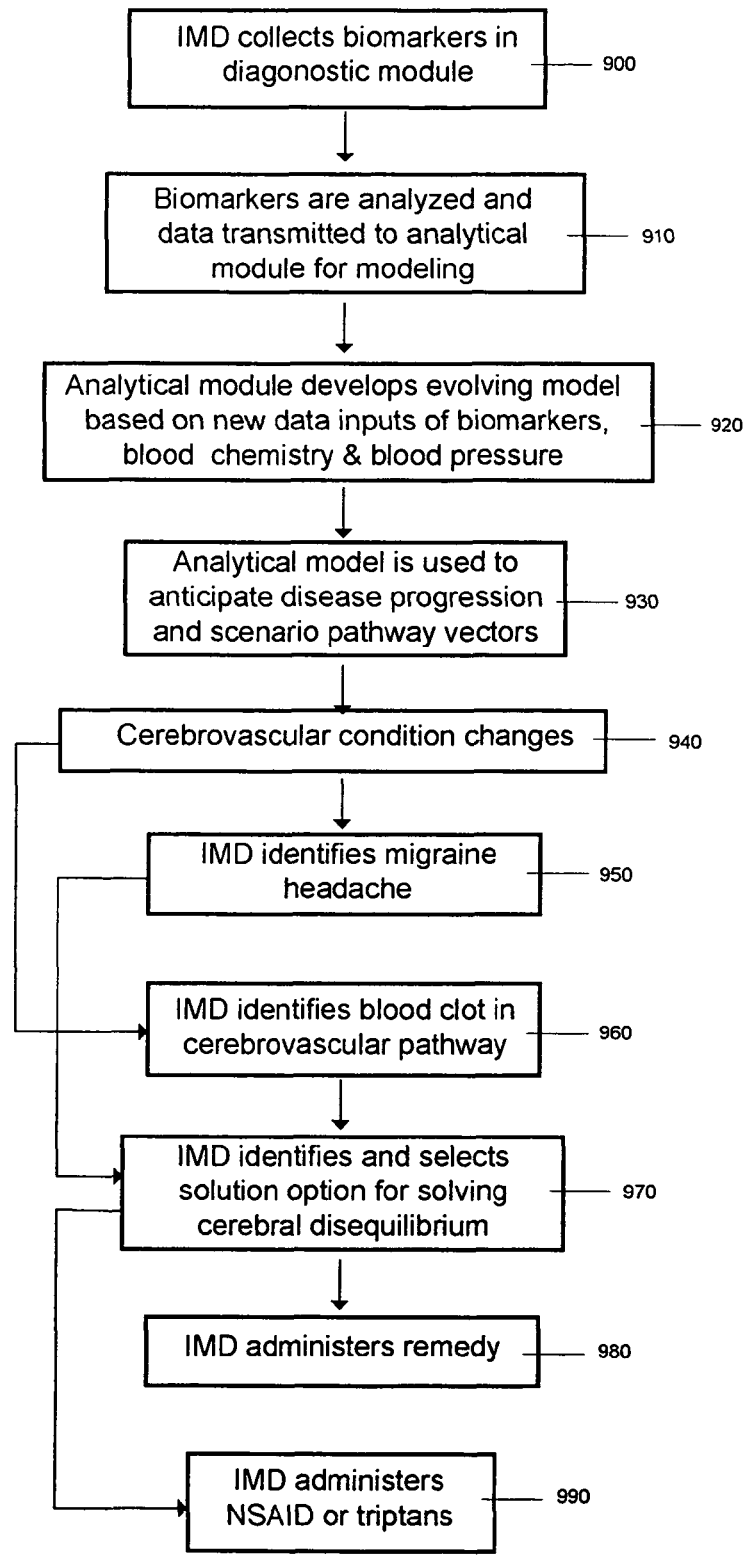
FIG. 9 is a flow chart describing the process of using an iMD to collect and analyze biomarkers to identify and treat a blood clot in the brain.

FIG. 9 shows the process of using an iMD to collect and analyze biomarkers to identify and treat a blood clot in the brain. After the iMD collects biomarkers in the diagnostic module (900), the biomarkers are analyzed and data transmitted to the analytical module for modeling (910). The analytical module develops an evolving model based on the new data inputs of biomarkers, blood chemistry and blood pressure (920). The analytical model is used to anticipate disease progression and scenario pathway vectors (930). As the cerebrovascular condition changes (940), the iMD identifies a migraine headache (950) and a blood clot in the cerebrovascular pathway (960). The iMD identifies and selects a solution option for solving cerebral disequilibrium (970) and administers a remedy (980). The iMD administers NSAID or triptans, to solve a migraine headache.

Figure 10:
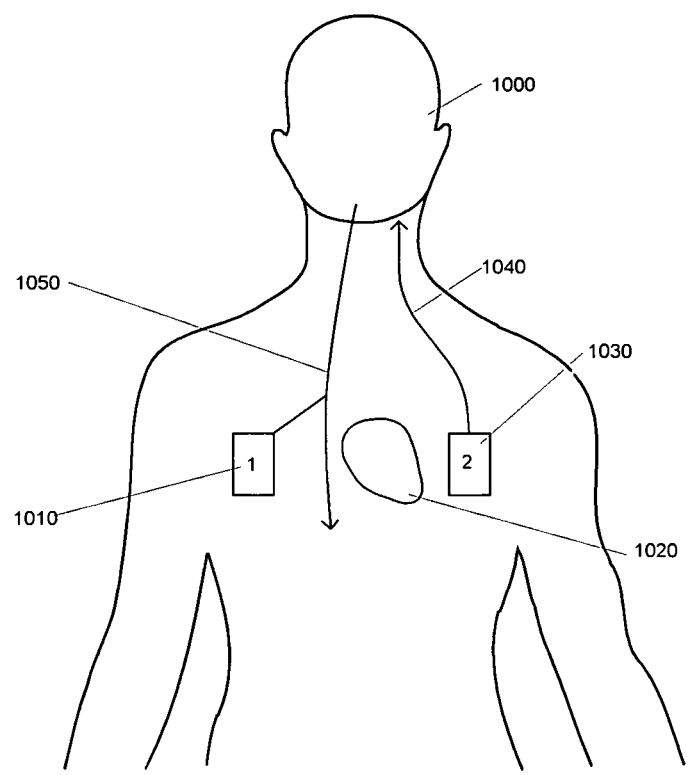
FIG. 10 is a drawing showing two iMDs treating epilepsy.

FIG. 10 shows two iMDs treating epilepsy. iMD 1 (1010) attaches a lead to the vagus nerve (1050). iMD 2 (1030) sends a connection (1040) to the brain (1000). When iMD 1 detects an electrical imbalance, it delivers an electric shock. IMD 2 applies a drug once iMD 1 detects electrical imbalance and iMD 1 transmits a signal to iMD 2.

Figure 11:
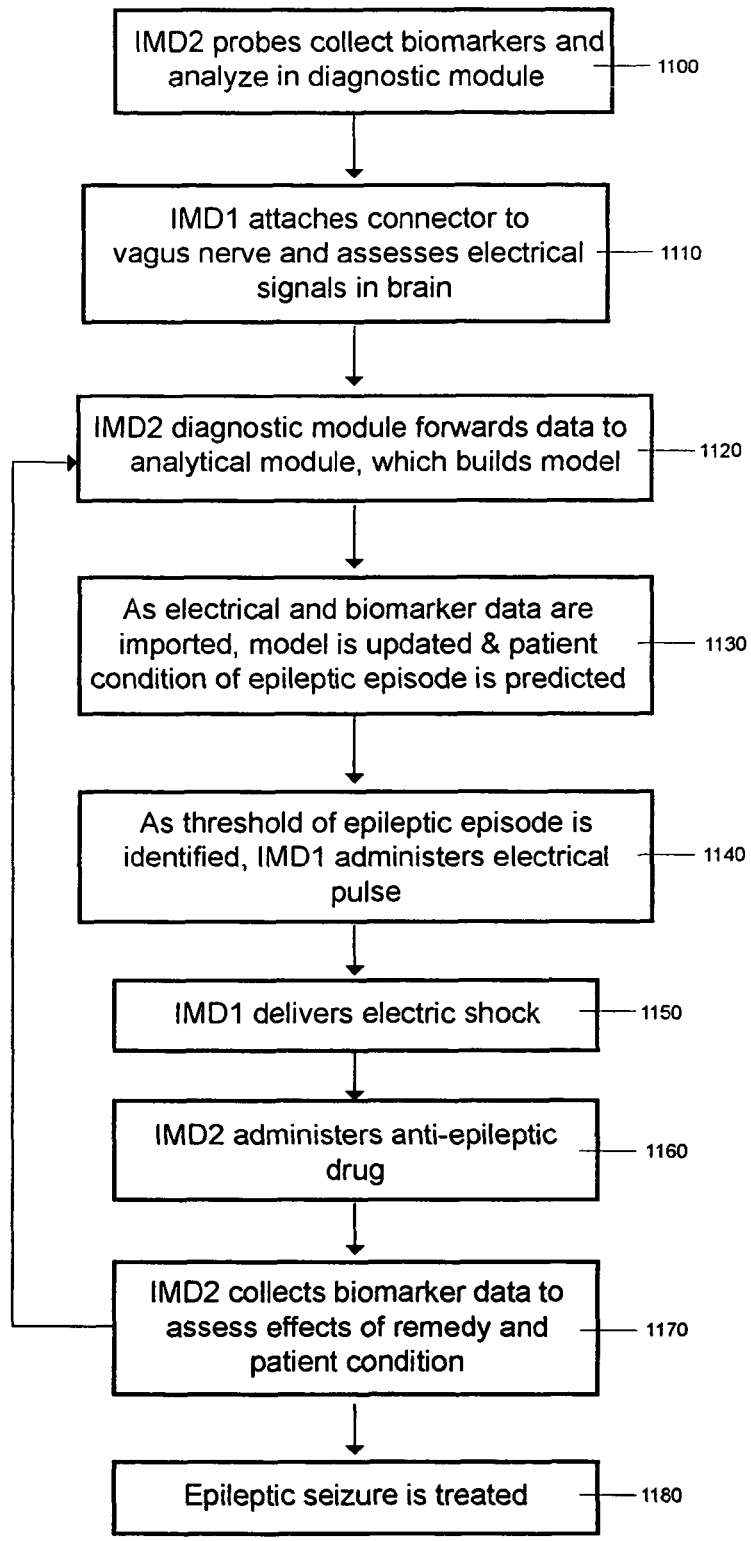
FIG. 11 is a flow chart showing the process of using iMDs to treat epilepsy.

FIG. 11 shows the process of using iMDs to treat epilepsy. Once iMD 2 probes collect biomarkers and analyze them in the diagnostic module (1100), iMD 1 attaches a connector to the vagus nerve and assesses electrical signals in the brain (1110). The iMD 2 diagnostic module forwards data to the analytical module, which builds a model (1120). As electrical and biomarker data are imported, the model is updated and a patient condition of epileptic episode is predicted (1130). As the threshold of epileptic episode is identified, iMD 1 administers an electrical pulse (1140) and delivers an electric shock (1150). The iMD 2 administers an anti-epileptic drug (1160)

and collects biomarker data to assess effects of the remedy and patient condition (1170). The epileptic seizure is treated (1180). In some cases this process anticipates a seizure and prevents it from occurring.

Figure 12:
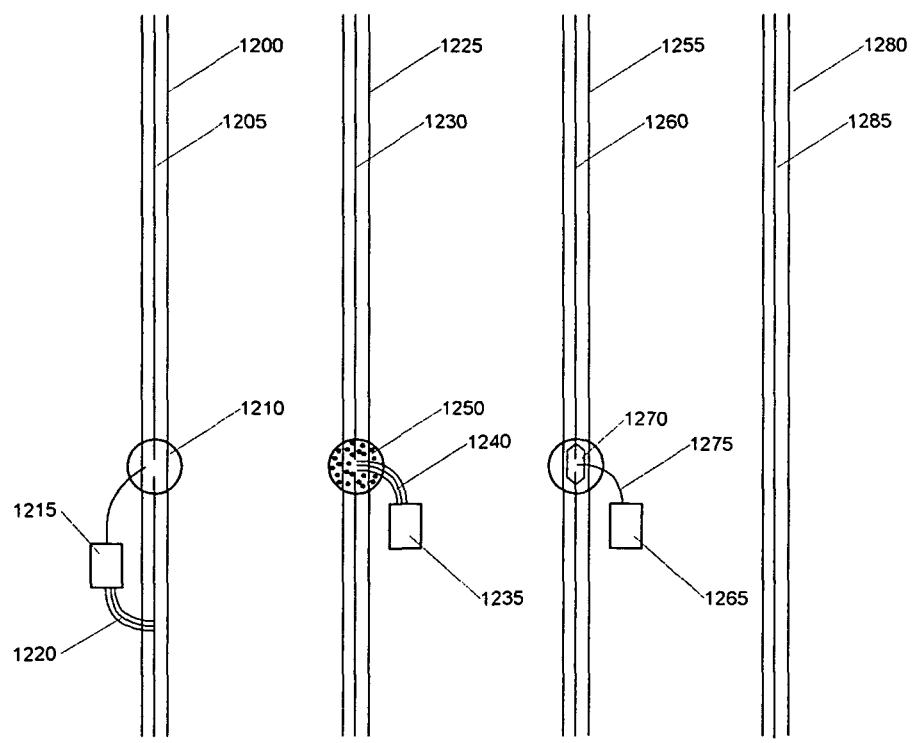
FIG. 12 is a set of diagrams to show four phases of using an iMD to treat spinal injury.

FIG. 12 shows the four phases of using an iMD to treat a spinal injury. In phase one, the spinal injury is shown (1210) with an iMD attaching leads (1220) to the spinal cord at 1210. In phase two, the iMD (1235) applies (1240) a treatment (1250) of stem cells to the spinal cord (1230) injury site. In phase three, the iMD (1265) applies (1275) a set of nano-wires in the gap between the spinal cord to act as a bridge (1270). In phase four, the iMD and the nano-wires are removed and the spinal cord heals. The main idea is that the iMD uses different methods to treat the cause and the effects of the spinal injury. The iMD also applies anti-inflammation drugs at the early stages of the spinal injury to limit the initial damage.

Figure 13:
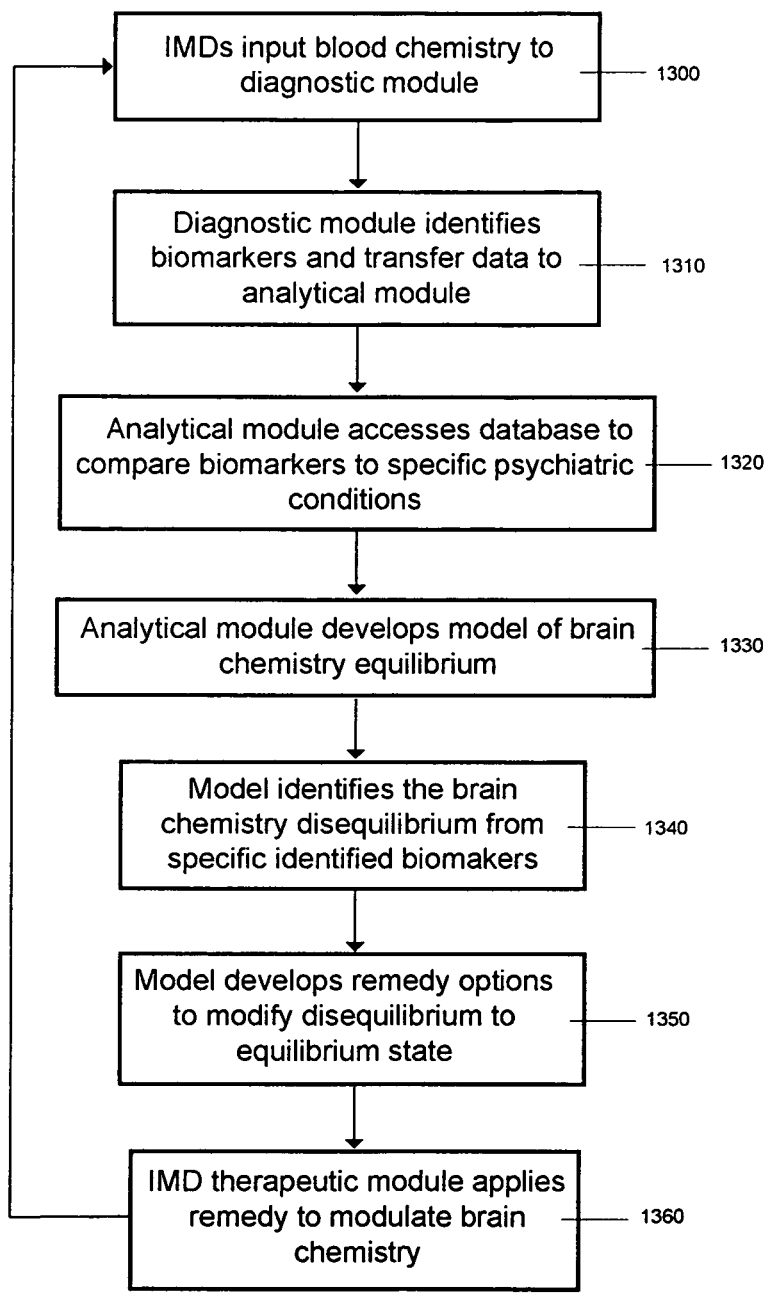
FIG. 13 is a flow chart showing the process of using an iMD to diagnose, analyze and modulate brain chemistry imbalances.

FIG. 13 shows the process of using an iMD to diagnose, analyze and modulate brain chemistry imbalances. After the iMDs input blood chemistry to the diagnostic module (1300), the diagnostic module identifies biomarkers and transfers the data to the analytical module (1310). The analytical module accesses databases to compare biomarkers to specific psychiatric conditions (1320) and develops a model of brain chemistry equilibrium (1330). The model identifies the brain chemistry disequilibrium from specific identified biomarkers (1340) and prior conditions and develops remedy options to modify disequilibrium to an equilibrium state (1350). An iMD therapeutic module applies the remedy to modulate brain chemistry (1360) and the process repeats.

Figure 14:
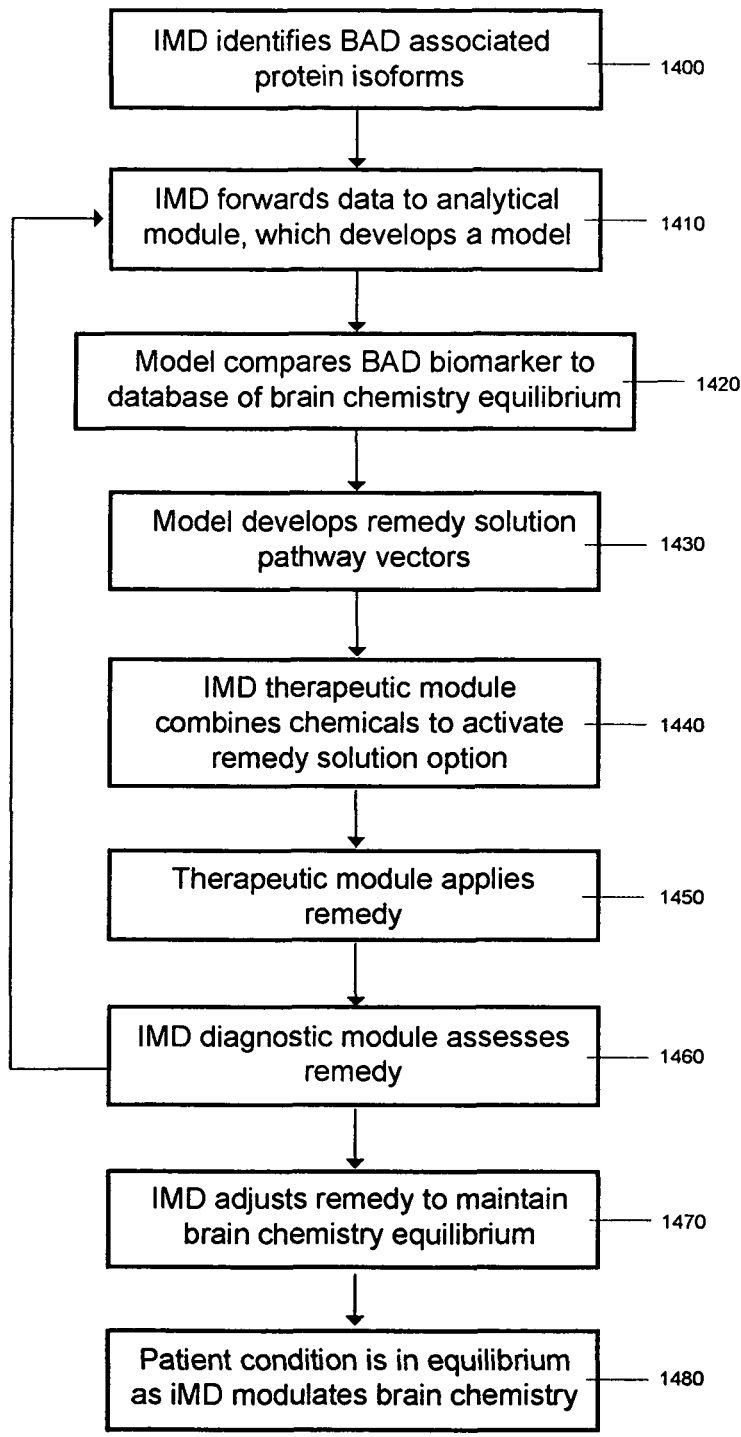
FIG. 14 is a flow chart showing the process of using an iMD to treat bipolar disorder.

FIG. 14 shows the process of using an iMD to treat bipolar disorder. Once an iMD identifies BAD associated protein isoforms (1400), it forwards the data to the analytical module, which develops a model (1410) and the model compares BAD biomarkers to a database of brain chemistry equilibria (1420). The model develops remedy solution pathway vectors (1430) and the iMD therapeutic module combines chemicals to activate the remedy solution option (1440). The therapeutic module applies the remedy (1450) and the iMD diagnostic module assesses the remedy (1460). The iMD then adjusts the remedy to maintain brain chemistry equilibrium (1470) and the patient condition is held in equilibrium as the iMD modulates brain chemistry (1480).

Figure 15:
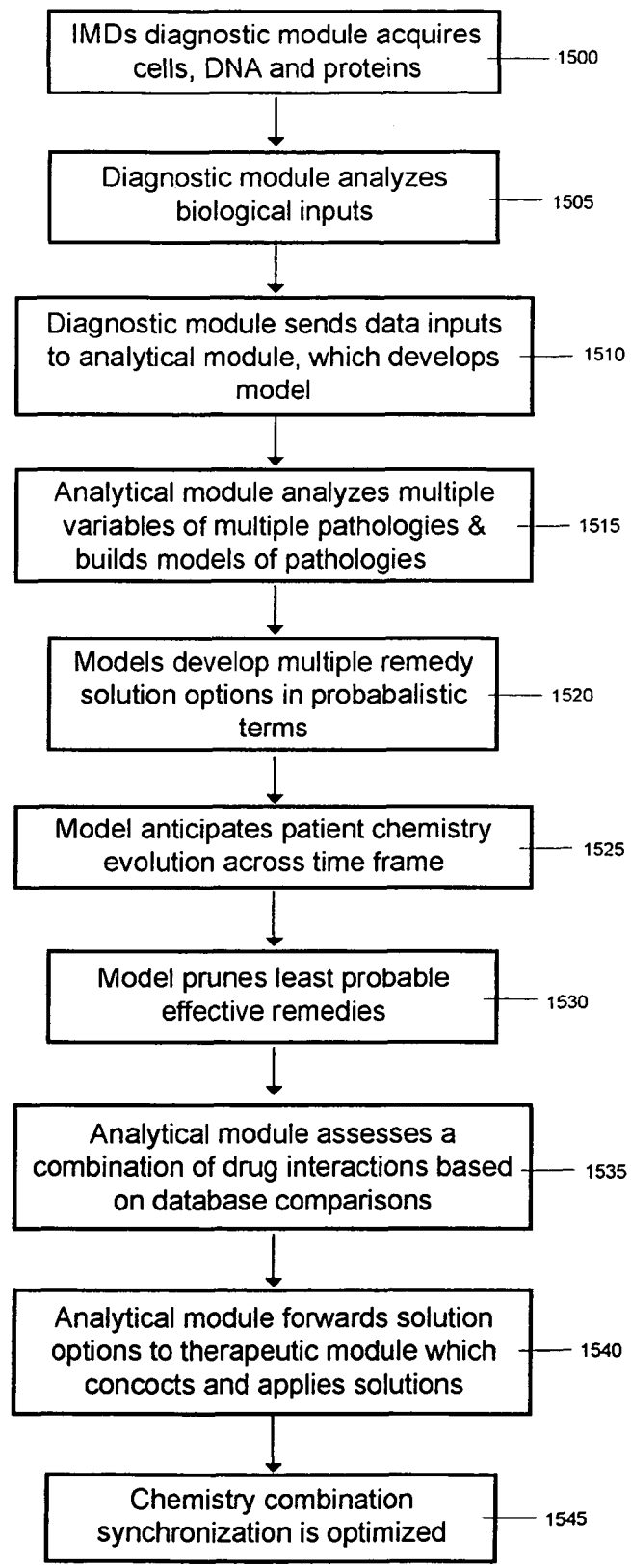
FIG. 15 is a flow chart showing the process of using an iMD to diagnose, analyze and treat multiple diseases.

FIG. 15 shows the process of using an iMD to diagnose, analyze and treat multiple diseases. After the iMD diagnostic module acquires cells, DNA and proteins (1500), the diagnostic module analyzes biological inputs (1505) and sends data inputs to the analytical module, which develops a model (1510). The analytical module then analyzes multiple variables of multiple pathologies and builds models of the pathologies (1515). The models develop multiple remedy solution options in probabilistic terms (1520). Each model anticipates patient chemistry evolution across a time frame (1525) and prunes the least probable effective remedies (1530). The analytical module assesses a combination of drug interactions based on database comparisons (1535) and forwards the solution options to the therapeutic module, which concocts and applies solutions (1540). The iMD's chemistry combination synchronization is optimized.

Figure 16:
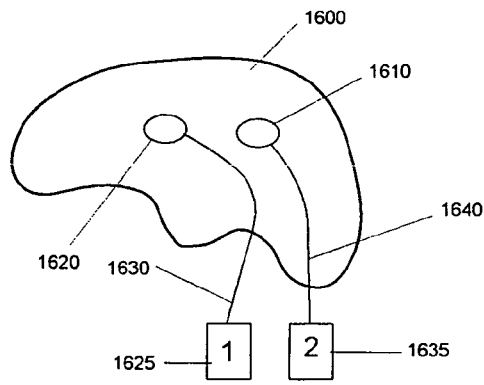
FIG. 16 is a drawing showing the iMD probes used to target two specific brain regions.

FIG. 16 shows the iMD probes used to target two specific brain regions. IMD 1 (1625) targets the region shown at 1620 using the connection at 1630 and iMD2 (135) targets the region shown at 1610 using the connection at 1640.

Figure 17:
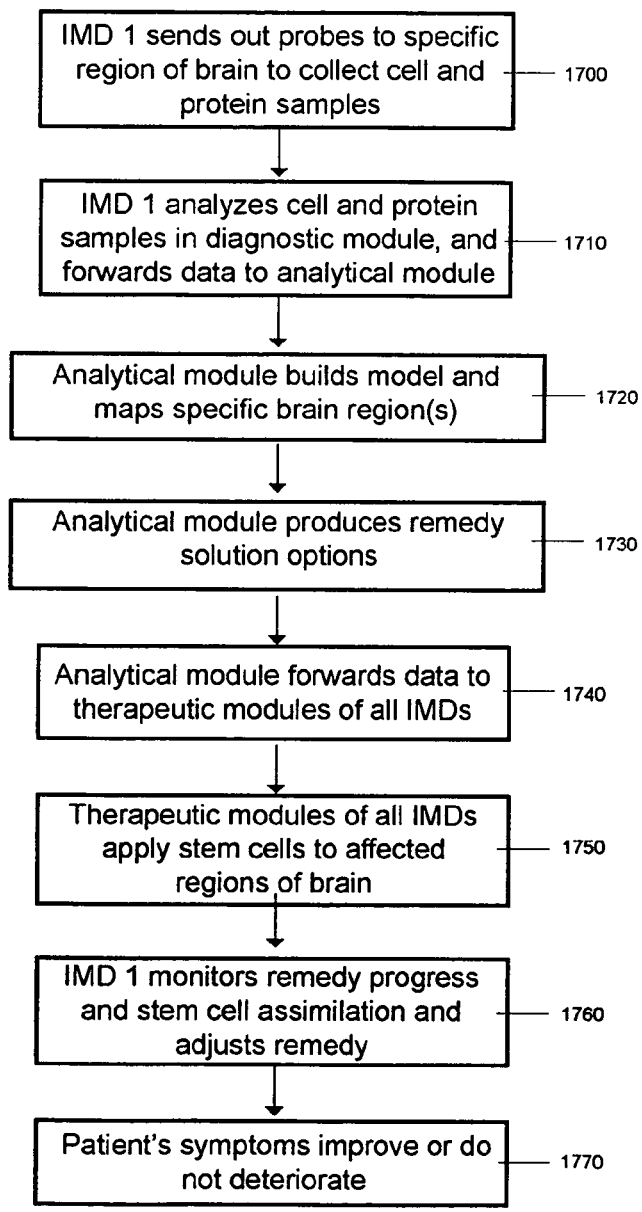
FIG. 17 is a flow chart showing the process of using an iMD to diagnose, analyze and treat degenerative neurological diseases.

FIG. 17 shows the process of using an iMD to diagnose, analyze and treat degenerative neurological diseases. After iMD 1 sends out probes to a specific region of the brain to collect cell and protein samples (1700), it analyzes cell and protein samples in the LOC and µTAS of the diagnostic module and forwards data to the analytical module (1710). The analytical module builds a model and maps specific brain region(s) (1720) and produces remedy solution options (1730). The analytical module then forwards data to therapeutic modules of all iMDs (1740) and the therapeutic modules apply stem cells to affected regions of the brain (1750). IMD 1 monitors remedy progress and stem cell assimilation, adjusts the remedy (1760) and the patient's symptoms improve or do not deteriorate (1770).

Figure 18:
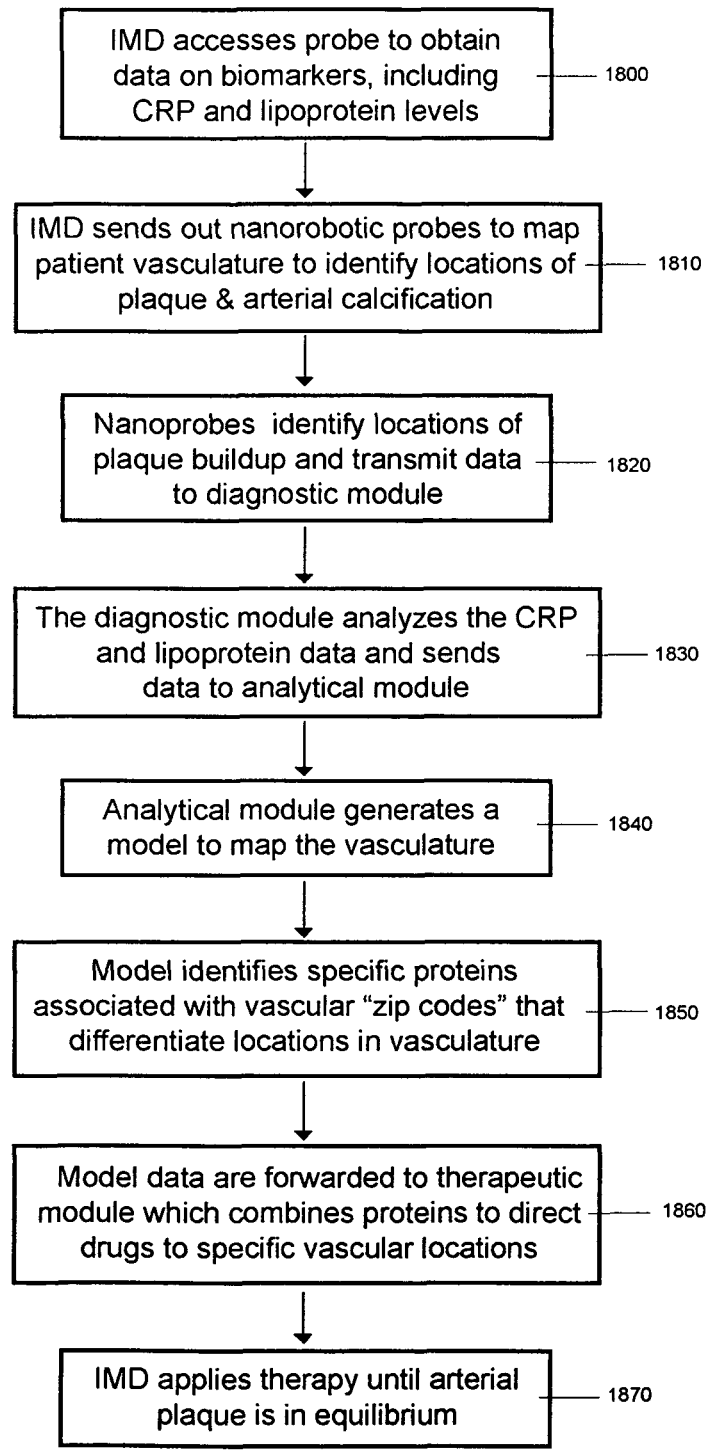
FIG. 18 is a flow chart showing the process of using an iMD to treat arteriosclerosis.

FIG. 18 shows the process of using an iMD to treat arteriosclerosis. Once an iMD accesses a probe to obtain data on biomarkers, including CRP and lipoprotein levels (1800), the iMD sends out nano probes to map patient vasculature to identify locations of plaque and arterial calcification (1810). The nanoprobes identify locations of plaque buildup and transmit data to the diagnostic module (1820). The diagnostic module analyzes the CRP and lipoprotein data and sends data to the analytical module (1830), which generates a model to map the vasculature (1840). The model identifies specific proteins associated with vascular "zip codes" that differentiate locations in the vasculature (1850). The model data are forwarded to the therapeutic module, which combines proteins to direct drugs to specific vascular locations (1860). The iMD applies the therapy until arterial plaque is in equilibrium (1870).

Figure 19:
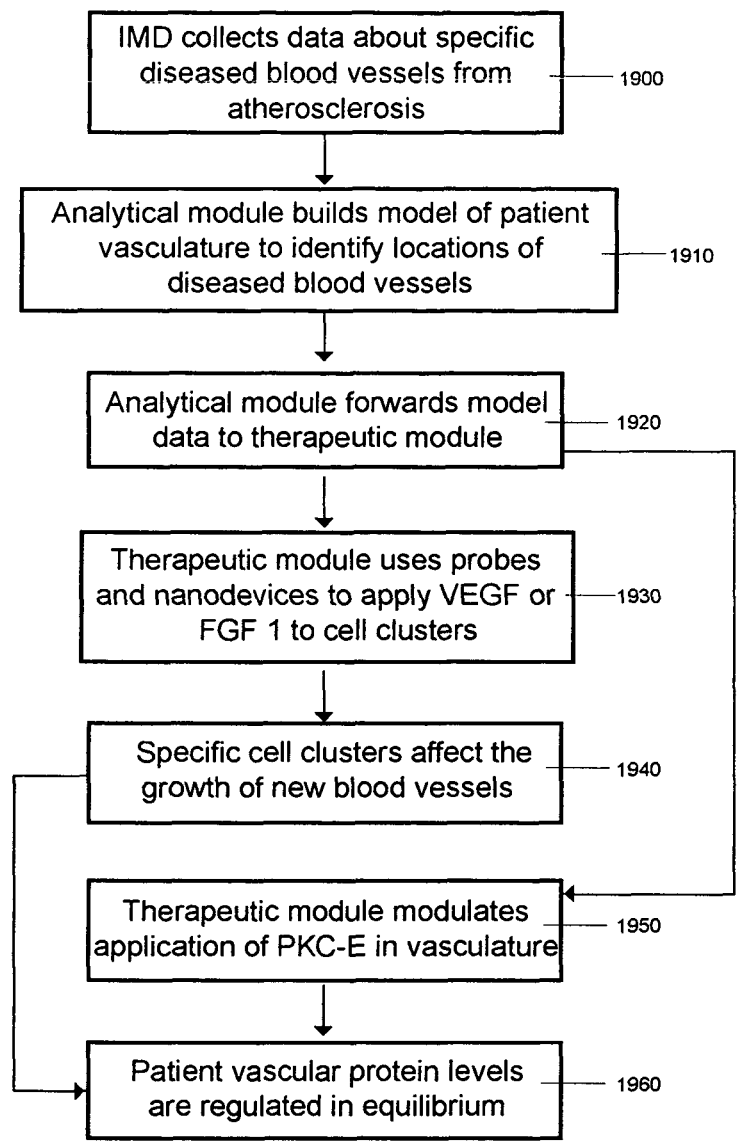
FIG. 19 is a flow chart showing the process of using an iMD to regulate vascular protein levels to optimize the growth of new blood vessels.

FIG. 19 shows the process of using an iMD to regulate vascular protein levels to optimize the growth of new blood vessels. The iMD initially collects data about specific diseased blood vessels from atherosclerosis (1900) and the analytical module builds a model of the patient's vasculature to identify locations of diseased blood vessels (1910). The analytical module forwards model data to the therapeutic module(s) (1920), which uses probes and nanodevices to apply VEGF or FGF-1 to cell clusters (1930). The specific cell clusters affect the growth of new blood vessels (1940) and the therapeutic module(s) modulate(s) application of PKC-E in the vasculature (1950). The patient's vascular protein levels are regulated in equilibrium (1960).

Figure 20:
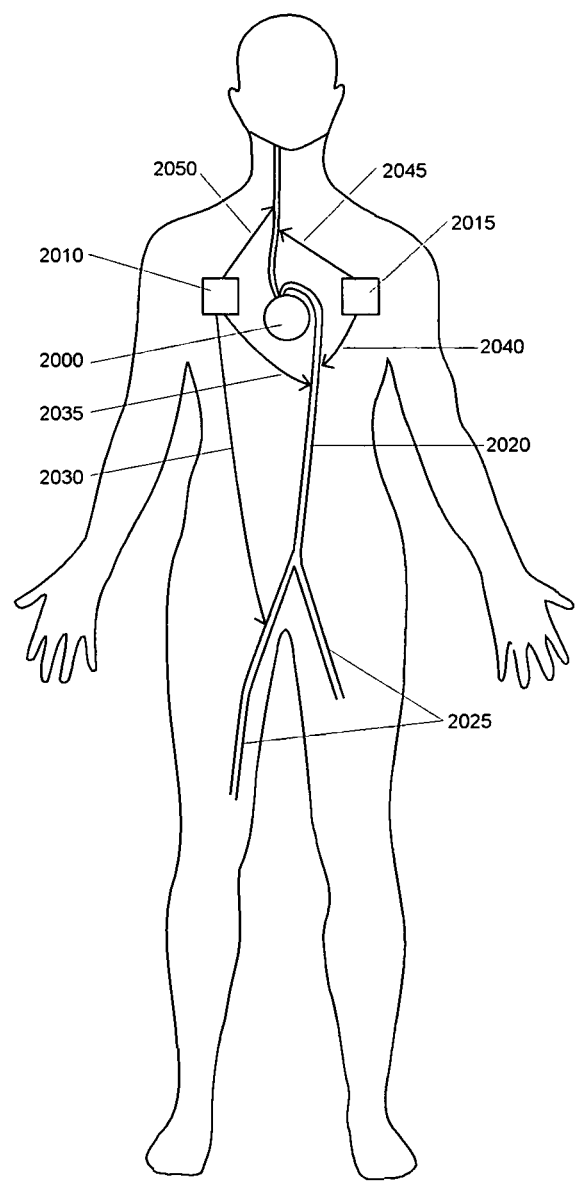
FIG. 20 is a diagram showing two iMDs connected to the vasculature in different positions.

FIG. 20 shows two iMDs connected to the vasculature in different positions. iMD 1 (2010) and 2 (2015) are connected to arteries as shown. The iMDs are able to collect cell samples and biomarkers for analysis and apply treatments as needed.

Figure 21:
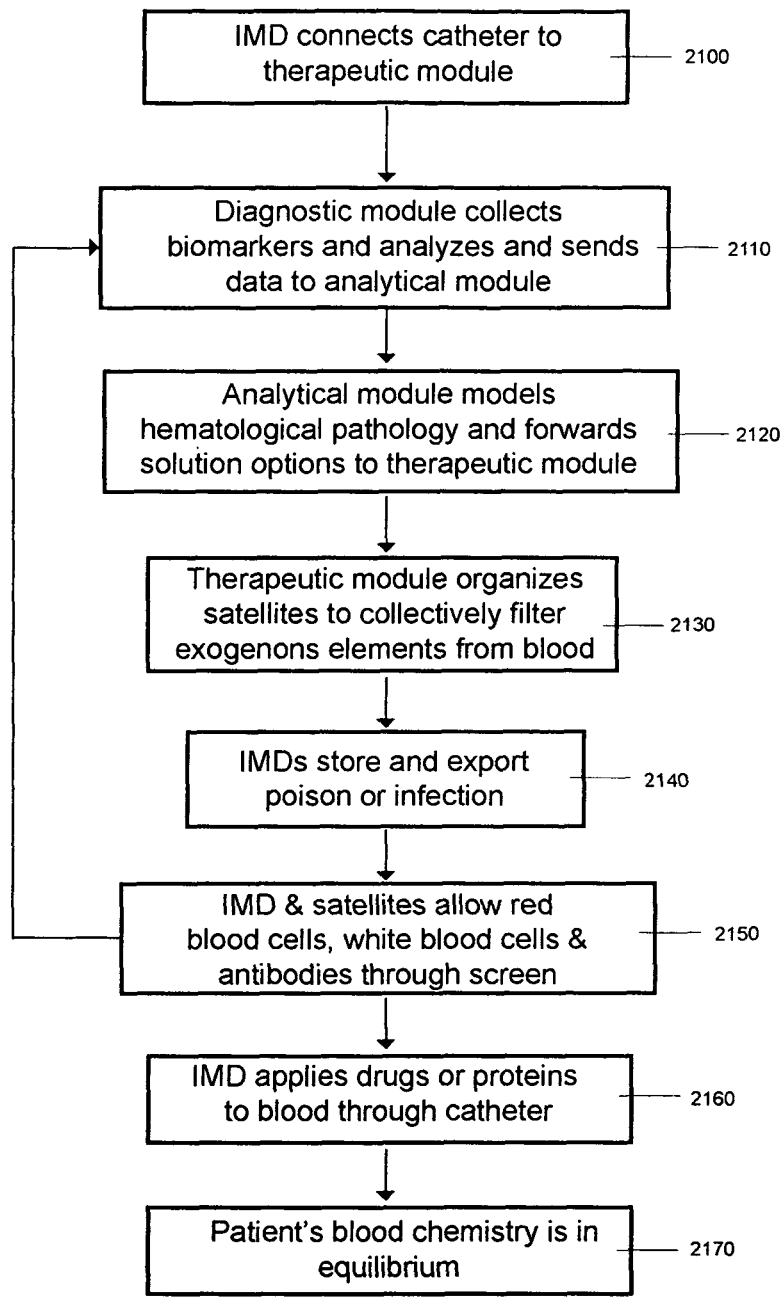
FIG. 21 is a flow chart describing the process of using an iMD to treat a hematological pathology.

FIG. 21 shows the process of using an iMD to treat a hematological pathology. After an iMD connects a catheter to a therapeutic module (2100), the diagnostic module collects biomarkers and analyzes and sends data to the analytical module (2110). The analytical module models hematological pathology and forwards solution options to a therapeutic module (2115). The therapeutic module organizes satellites to collectively filter exogenous elements from the blood (2120) and the iMD stores and exports a poison or infection (2130). The iMD and satellites allow red blood cells, white blood cells and antibodies through a screen (2140) and applies drugs or proteins to the blood through the catheter (2150). The patient's blood chemistry is then in equilibrium (2160).

Figure 22:
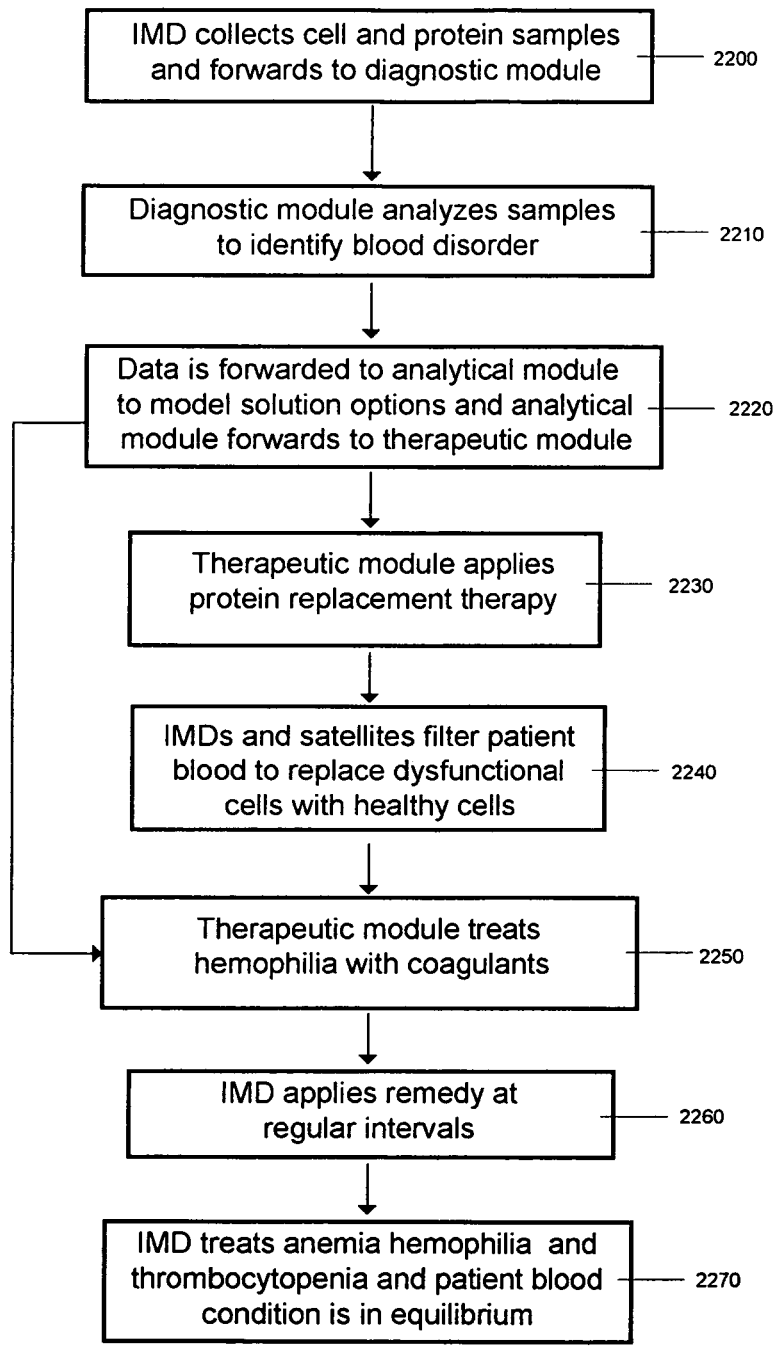
FIG. 22 is a flow chart describing the process of using an iMD to treat anemia, hemophilia and thrombocytopenia.

FIG. 22 shows the process of using an iMD to treat anemia, hemophilia and thrombocytopenia. Once the iMD collects cell and protein samples and forwards them to the diagnostic module (2200), the diagnostic module analyzes samples to identify a blood disorder (2210). The data is forwarded to the analytical module to model solution options, which are forwarded to the therapeutic module (2220), which applies protein replacement therapy (2230). The iMD and satellites filter patient blood to replace dysfunctional cells with healthy cells (2240). The therapeutic module treats hemophilia with coagulants (2250) and the iMD applies the remedy at regular intervals (2260). The iMD treats anemia, hemophilia and thrombocytopenia and the patient blood condition is in equilibrium (2270).

In another embodiment, the iMD is used to disseminate glyceryl trinitrate upon detection of initiation of a myocardial infarction. The iMD maps the patient condition and is able to anticipate the probabilities of a heart attack.

Figure 23:
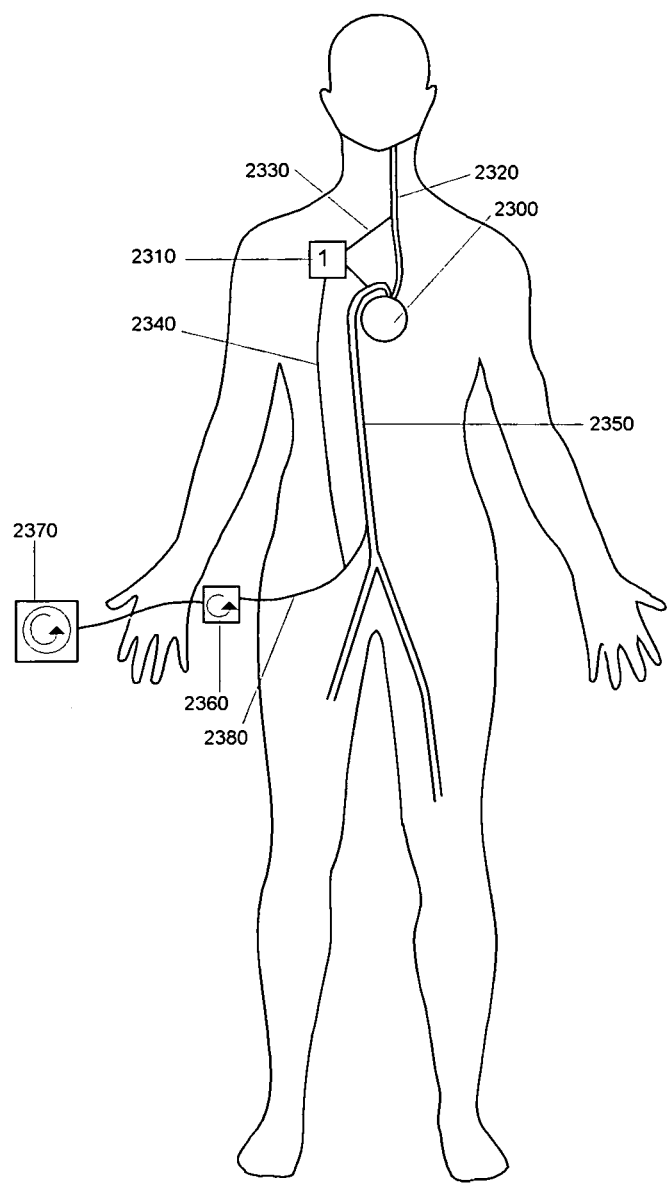
FIG. 23 is a diagram showing the use of an iMD in a network of devices to supplement blood cells and oxygen.

FIG. 23 shows the use of an iMD in a network of devices to supplement blood cells and oxygen. The iMD (2310) is connected to arteries (2310 and 2350). The iMD is connected to an external iMD (2360) at 2380. The external iMD is connected to multiple devices for evacuation of blood, for blood cell supplementation and for oxygen supplementation by an oxygen generator.

Figure 24:
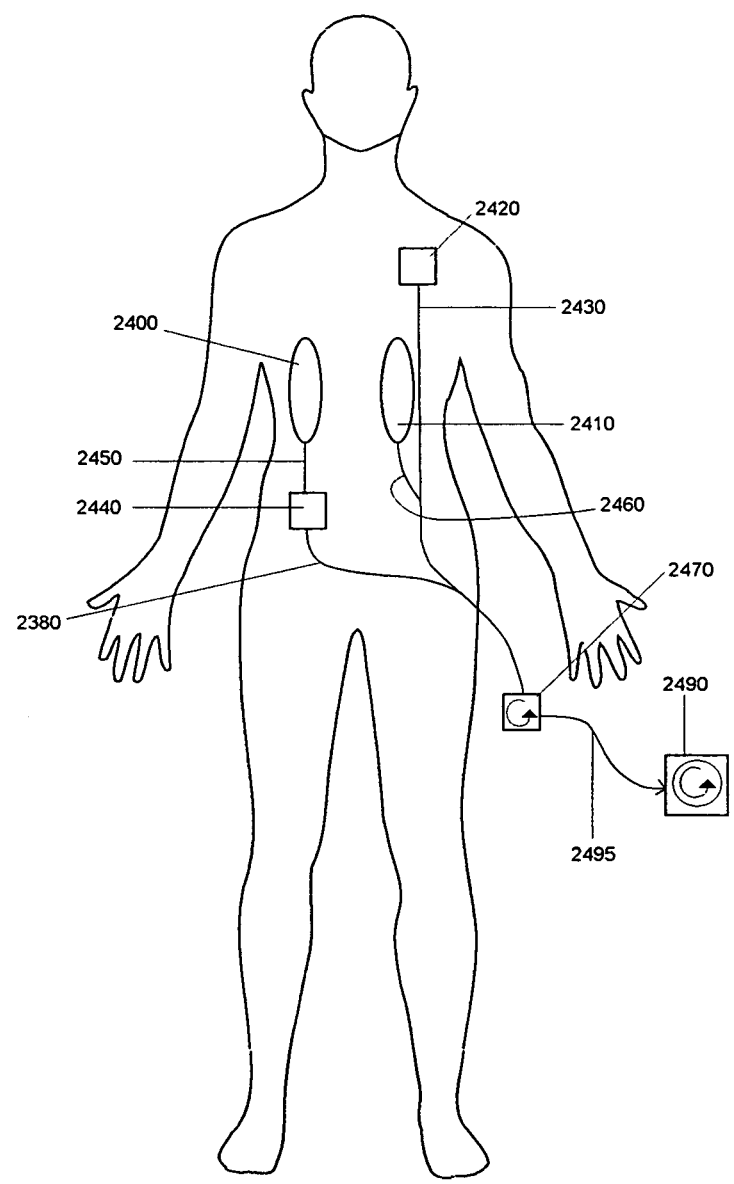
FIG. 24 is a diagram showing the use of two iMDs in a network of devices to drain and modulate fluid from the lungs.

FIG. 24 shows the use of two iMDs in a network of devices to drain and modulate fluid from the lungs. The iMDs (2420 and 2440) connect to the lungs (2400 and 2410) as shown to drain the lungs of excess fluid. The fluid drainage is then sent to an external iMD (2470), which expels the fluids in a device (2490).

Figure 25:
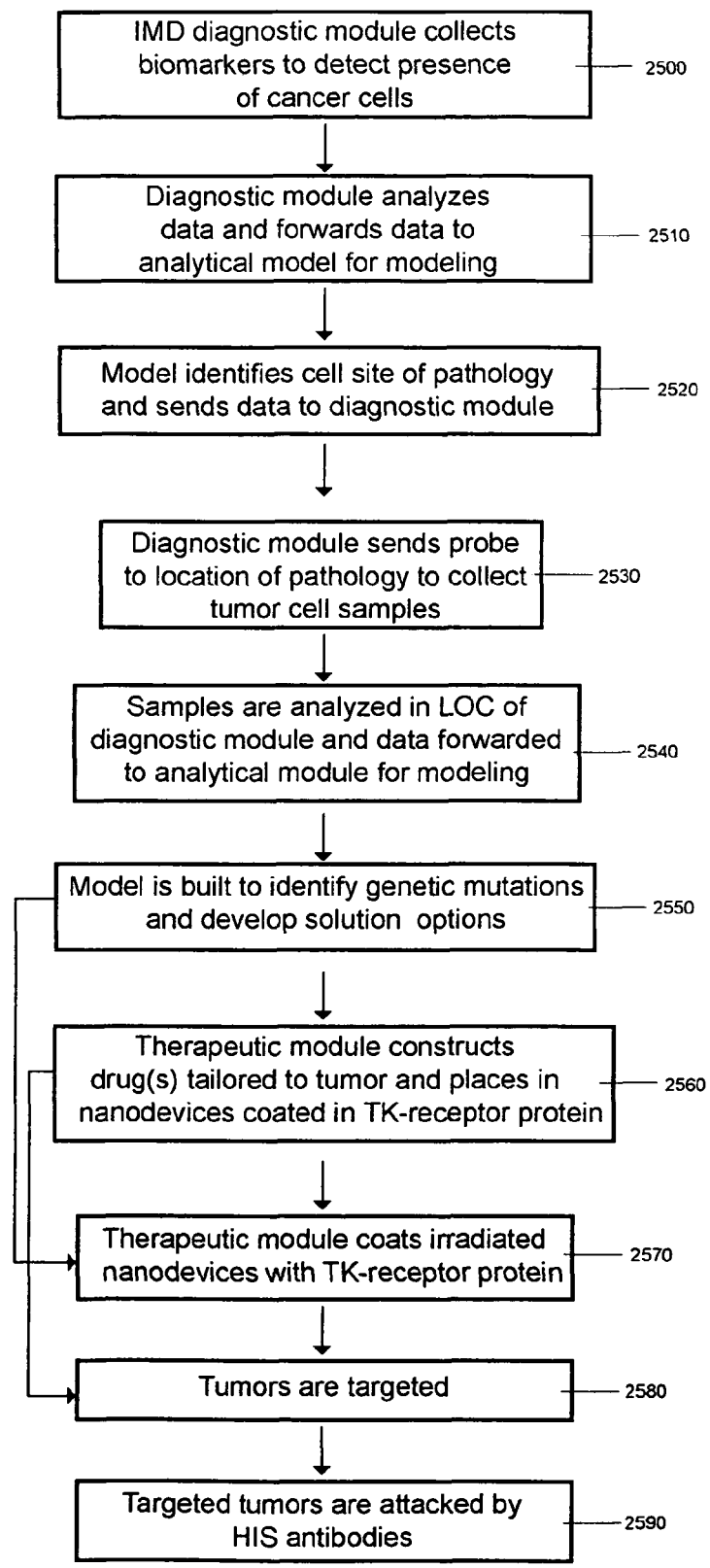
FIG. 25 is a flow chart describing the process of diagnosing, analyzing and treating cancer pathologies using an iMD.

FIG. 25 shows the process of diagnosing, analyzing and treating cancer pathologies using an iMD. After an iMD diagnostic module collects biomarkers to detect the presence of cancer cells (2500), the diagnostic module analyzes the data and forwards data to the analytical module for modeling (2510). The model identifies the cell site(s) of pathology and sends data to the diagnostic module (2520). The diagnostic module sends probes to the location of pathology to collect tumor cell samples (2530), samples are analyzed in the LOC of diagnostic module and data forwarded to the analytical module for modeling (2540). The model is built to identify genetic mutations and develop solution options (2550). The therapeutic module constructs drug(s) tailored to each tumor and places in nanodevices coated in TK-receptor protein (2560). The therapeutic module also coats irradiated nanodevices with TK-receptor protein (2570) and tumors are targeted (2580). Targeted tumors are attacked by HIS antibodies (2590).

Figure 26:
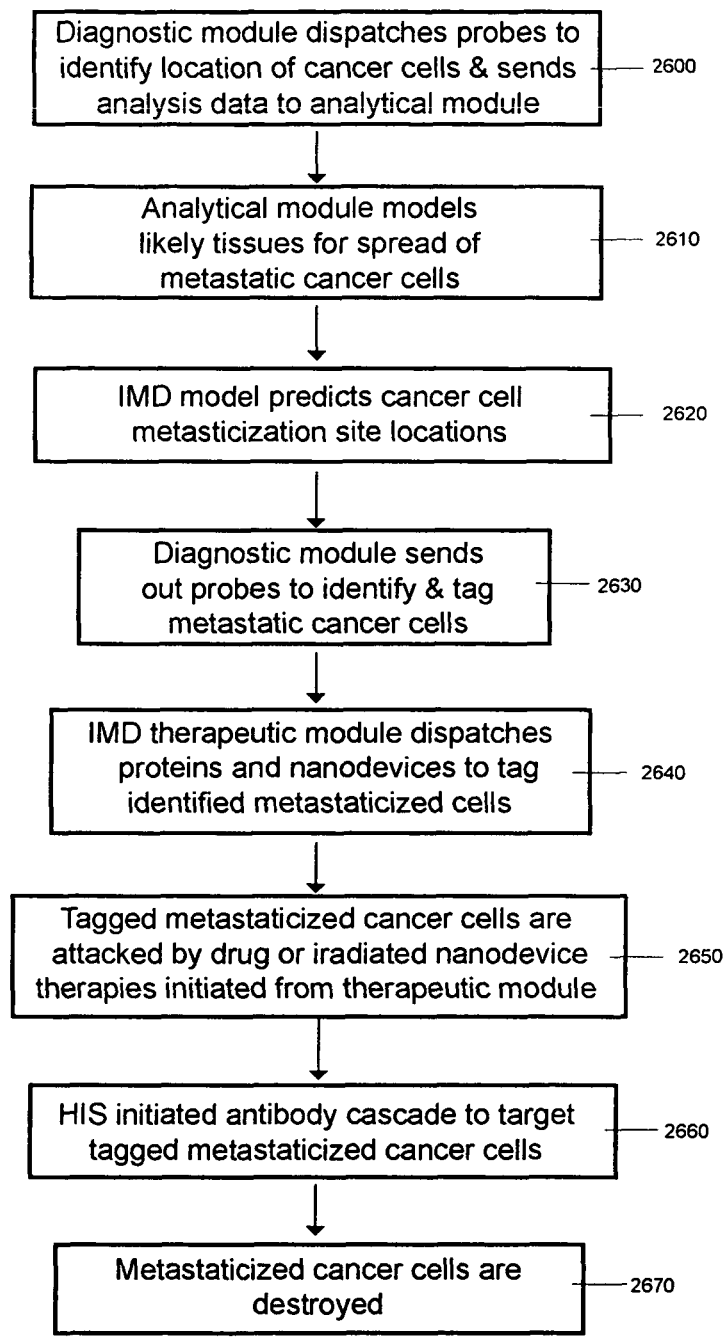
FIG. 26 is a flow chart describing the process of diagnosing, analyzing and treating metastatic cancer using an iMD.

FIG. 26 shows the process of diagnosing, analyzing and treating metastatic cancer using an iMD. An iMD diagnostic module first dispatches probes to identify the location of cancer cells and sends analysis data from testing of cell samples in the LOC to the analytic module (2600). The analytical module then models likely tissues for spread of metastatic cancer cells (2610) and the iMD model predicts likely cancer cell metasticization site locations (2620). The diagnostic module sends out probes to identify and tag metastatic cancer cells (2630). The iMD therapeutic module dispatches proteins and nanodevices to tag identified metasticized cells (2640). The tagged metasticized cancer cells are attacked by drug or irradiated nanodevice therapies initiated from the therapeutic module (2650) and the HIS initiates an antibody cascade to target tagged metasticized cancer cells (2660). The metasticized cancer cells are destroyed (2670).

Figure 27:
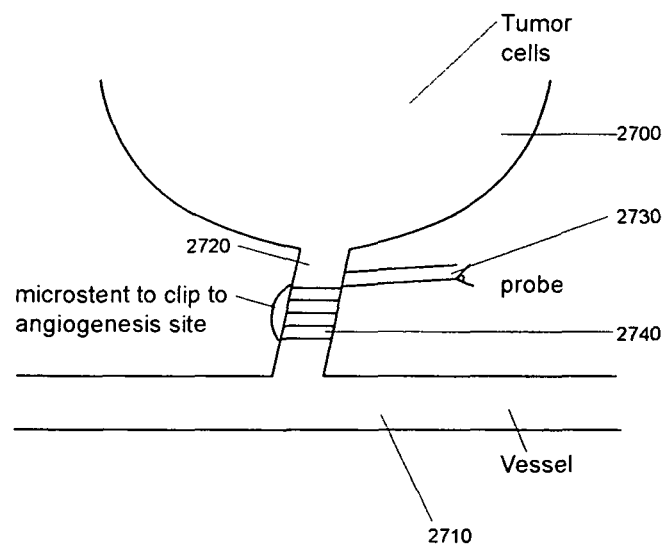
FIG. 27 is a diagram showing a micro-stent clipped to an angiogenesis site between a tumor cell cluster and healthy tissue.

FIG. 27 shows a micro-stent clipped to an angiogenesis site between a tumor cell cluster and healthy tissue. The tumor cells (2700) build a bridge (2720) with angiogenesis to a nearby vessel (2710) to feed it. A probe (2730) is dispatched from an iMD to attach a micro-stent (2740) to clip to the angiogenesis site to block the bridge formation and prevent the tumor from getting blood.

Figure 28:
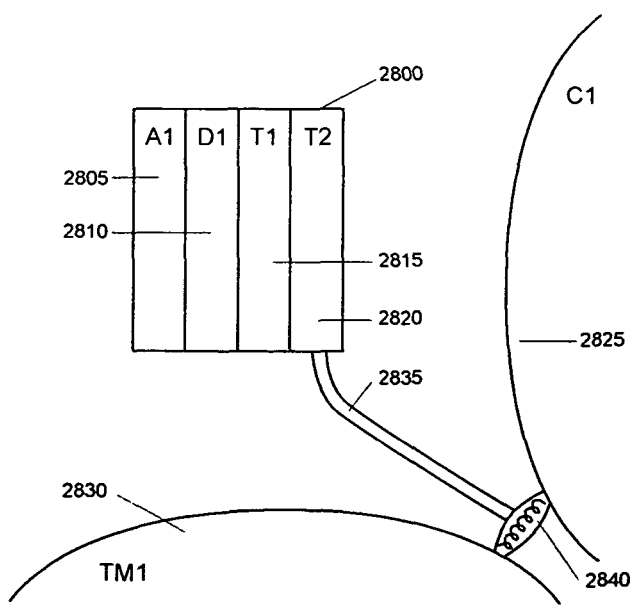
FIG. 28 is a schematic diagram showing the use of an iMD to treat angiogenesis of tumor cells.

FIG. 28 shows the use of an iMD to treat angiogenesis of tumor cells. After collecting samples in the diagnostic module (2810) and analyzing the data in the analytical module (2805) of the iMD, therapeutic module 2 (2820) applies a coil to block the angiogenesis from the tumor (2830) to the healthy tissue (2825). The coil expands and disrupts the bridge.

Figure 29:
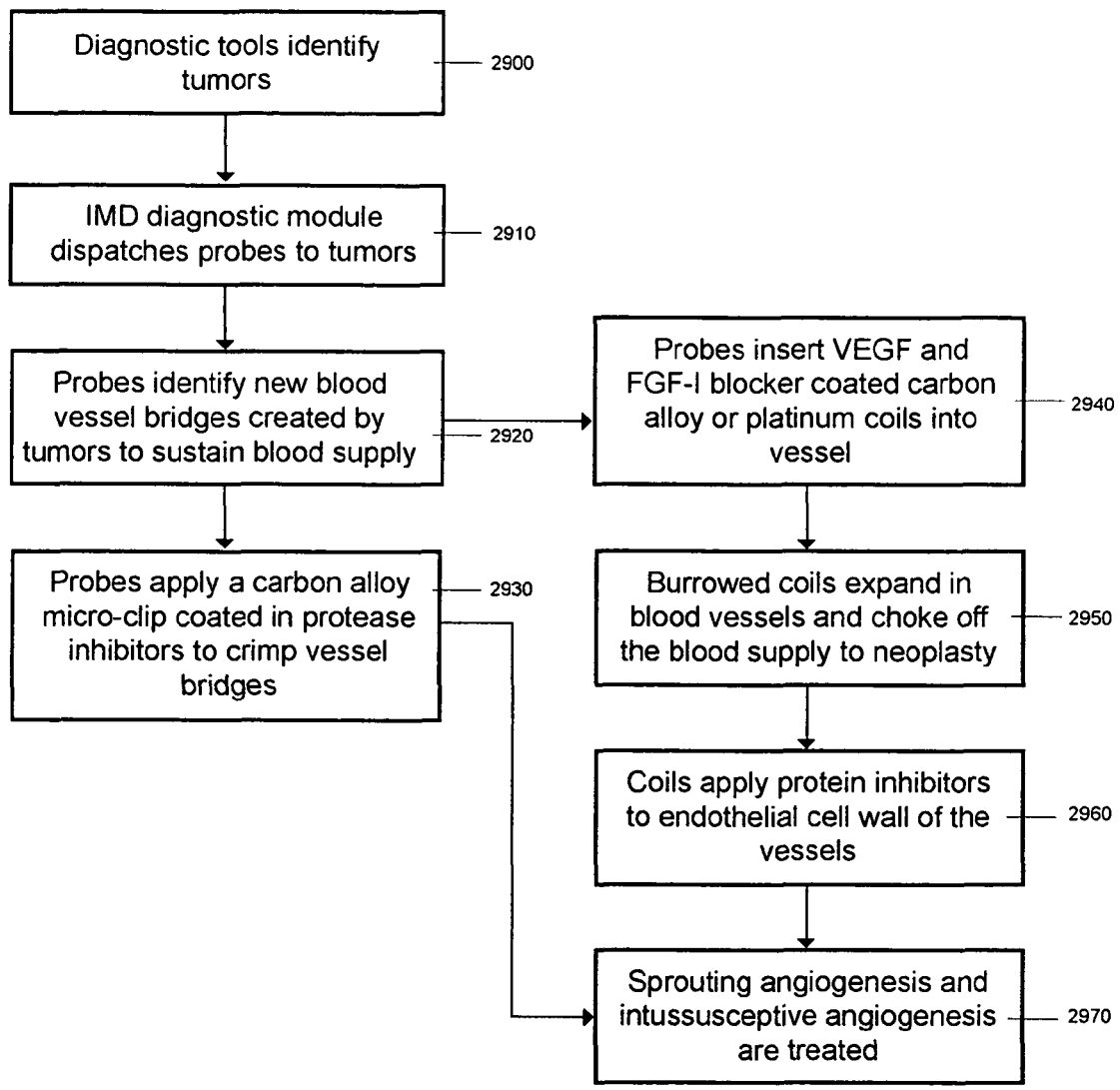
FIG. 29 is a flow chart describing the process of treating angiogenesis with iMDs.

FIG. 29 shows the process of treating angiogenesis with iMDs. After the diagnostic tools identify tumors (2900), the iMD diagnostic module dispatches probes to tumors (2910) and the probes identify new blood vessel bridges created by tumors to sustain blood supply (2920). The probes apply a carbon alloy micro-clip coated in protease inhibitors to crimp vessel bridges (2930). At the same time, probes insert VEGF and FGF-1 blocker coated carbon alloy or platinum coils into the vessel (2940). The burrowed coils expand in the blood vessels and choke off the blood supply to the neoplasty (2950). The coils apply protein inhibitors to the endothelial cell wall of the vessels (2960) and sprouting angiogenesis and intussusceptive angiogenesis are treated (2970).

Figure 30:
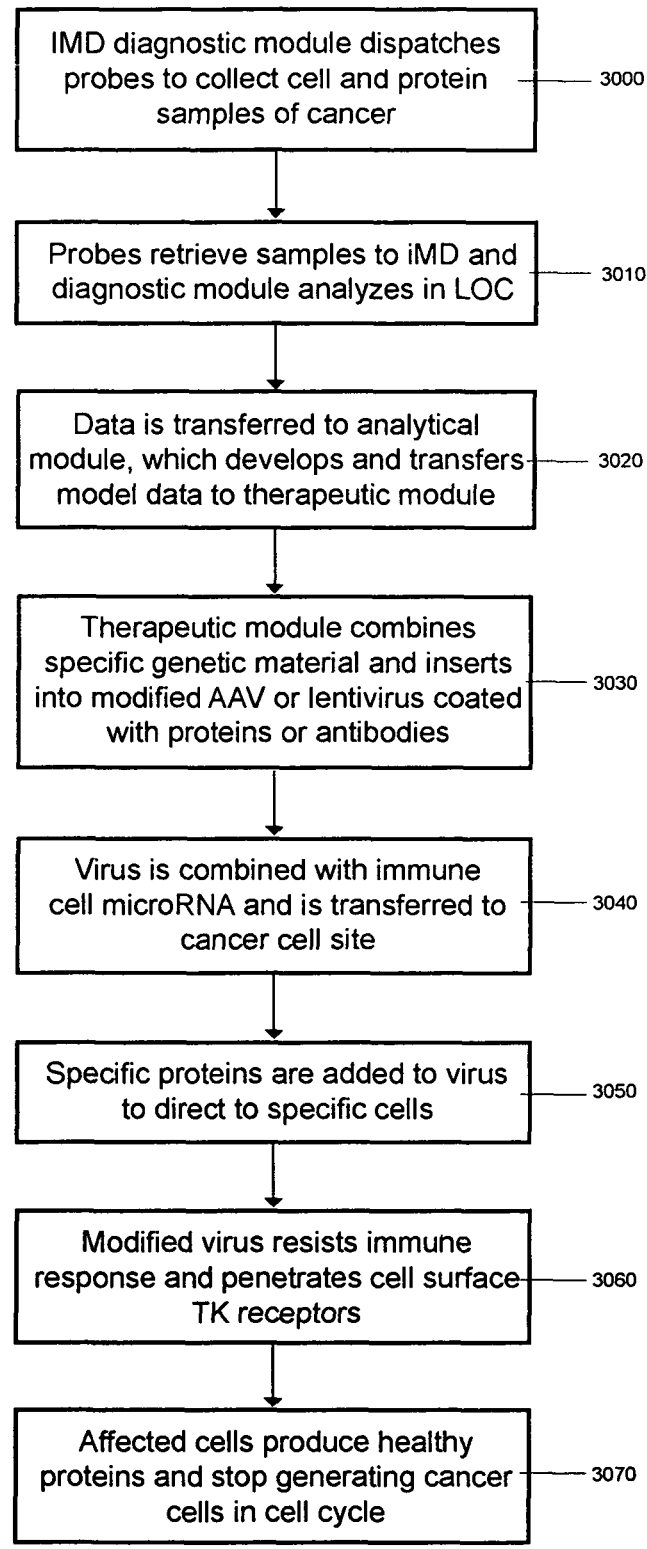
FIG. 30 is a flow chart describing the process of using an iMD to diagnose, analyze and treat a tumor using protein therapy with an application by a virus.

FIG. 30 shows the process of using an iMD to diagnose, analyze and treat a tumor using protein therapy with an application by a virus. After the iMD diagnostic module dispatches probes to collect cell and protein samples of cancer (3000), the probes retrieve samples to the iMD and the diagnostic module analyzes these in the LOC and μTAS (3010). The data are transferred to the analytical module, which develop and transfer model data to the therapeutic module (3020). The therapeutic module combines specific genetic material and inserts into modified AAV or lentivirus coated with proteins or antibodies (3030). The virus is combined with immune cell microRNA and is transferred to the cancer cell site (3040). Specific proteins are added to the virus to direct to specific cells (3050). The modified virus resists immune response and penetrates cell surface TK receptors (3060). The affected cells produce healthy proteins and stop generating cancer cells in cell cycle (3070).

Figure 31:
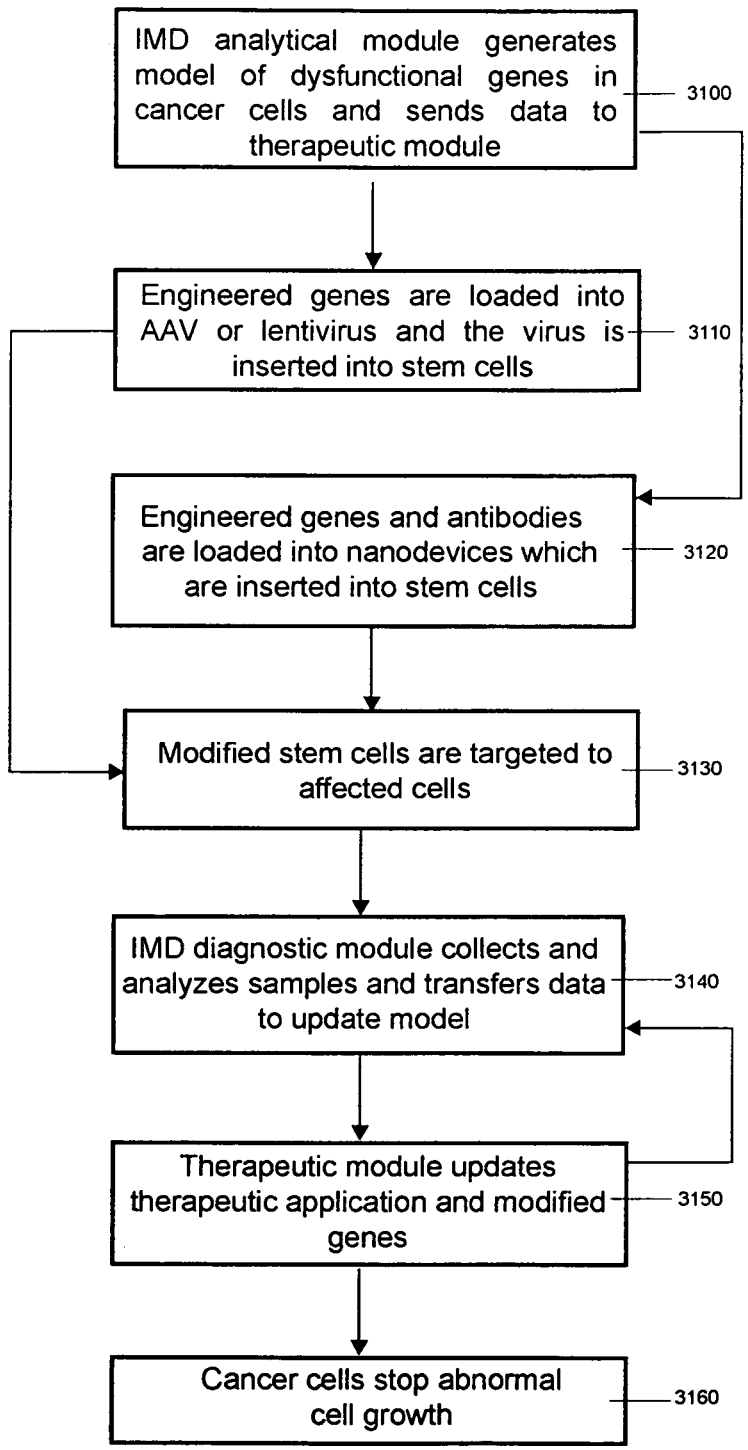
FIG. 31 is a flow chart describing the process of using an iMD to diagnose and treat a tumor using engineered genes and application by stem cells.

FIG. 31 shows the process of using an iMD to diagnose and treat a tumor using engineered genes and application by stem cells. After the iMD analytical module generates a model of dysfunctional genes in cancer cells and sends data to the therapeutic module (3100), the engineered genes are loaded into AAV or lentivirus and the virus is inserted into stem cells (3110). The engineered genes and antibodies are also loaded into nanodevices which are inserted into stem cells (3120). The modified stem cells are then targeted to affected cells (3130). The iMD's diagnostic module collects and analyzes samples in its LOC and μTAS and transfers data to update the model (3140). The therapeutic module then updates the therapeutic application and modifies genes (3150) until cancer cells stop abnormal cell growth (3160).

Figure 32:
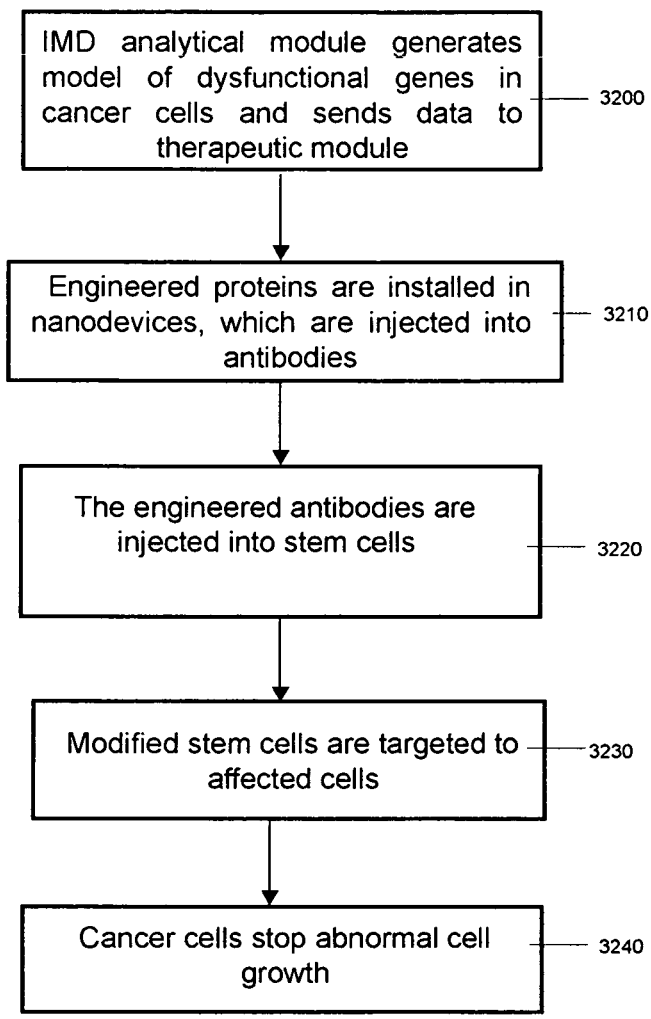
FIG. 32 is a flow chart describing the process of using an iMD to treat a tumor using nanodevices and application by antibodies and stem cells.

FIG. 32 shows the process of using an iMD to treat a tumor using nanodevices and application by antibodies and stem cells. Once an iMD analytical module generates a model of dysfunctional cancer genes and sends data to a therapeutic module (3200), the engineered proteins are installed in nanodevices, which are injected into antibodies (3210). The engineered antibodies are injected into stem cells (3220) and the modified stem cells are targeted to affected cells (3230) until the cancer cells stop abnormal cell growth (3240).

Figure 33:
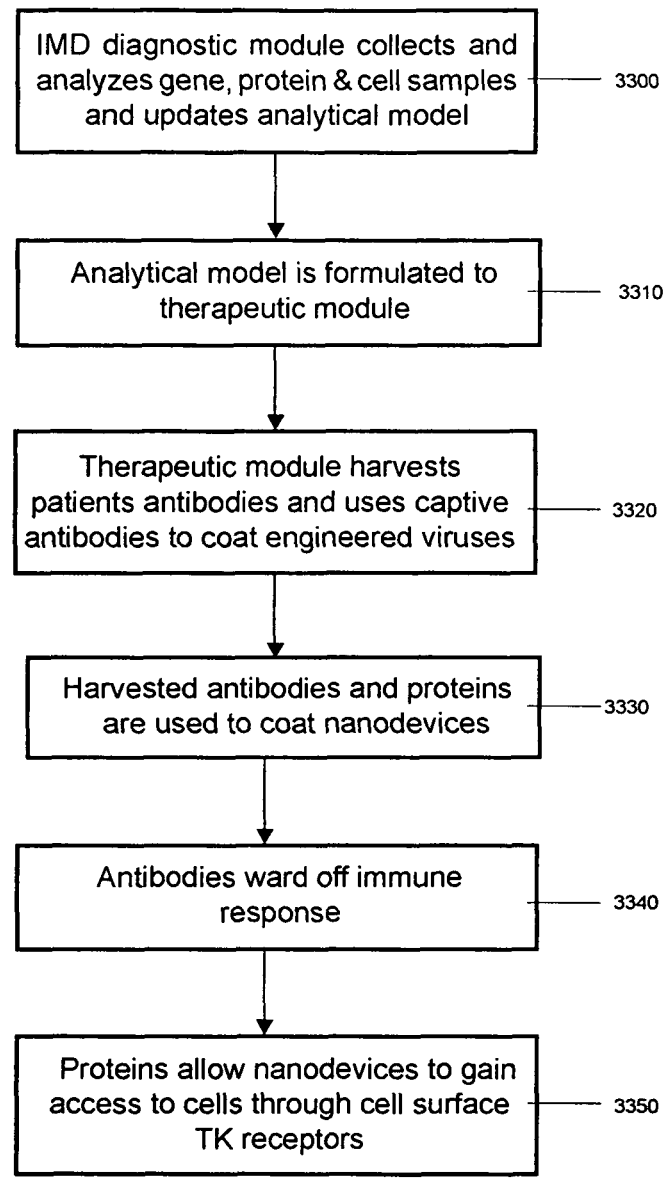
FIG. 33 is a flow chart describing the process of using an iMD to treat a tumor by harvesting a patient's antibodies for application by engineered viruses.

FIG. 33 shows the process of using an iMD to treat a tumor by harvesting a patient's antibodies for application by engineered viruses. After an iMD diagnostic module collects and analyzes gene, protein and cell samples and updates the analytical model (3300), the analytical model is forwarded to the therapeutic module (3310), which harvests the patient's antibodies and uses captive antibodies to coat engineered viruses (3320). The harvested antibodies and proteins are also used to coat nanodevices (3330). The antibodies then ward off immune response (3340). The proteins allow nanodevices to gain access to cells through cell surface TK receptors (3350).

Figure 34:
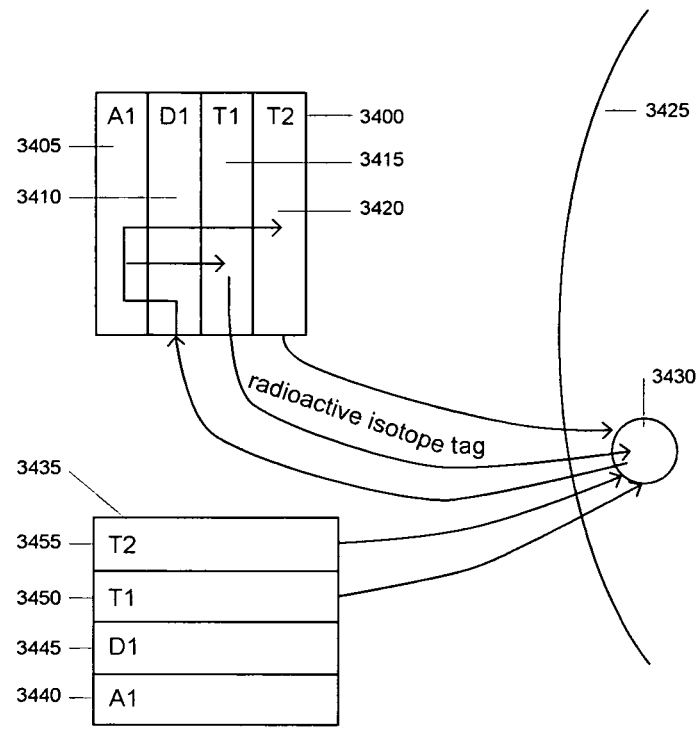
FIG. 34 is a schematic diagram showing the use of two iMDs to treat a tumor by using a radioactive isotope to tag the tumor.

FIG. 34 shows the use of two iMDs to treat a tumor by using a radioactive isotope to tag the tumor. After the diagnostic module (3410) of iMD 1 (3400) collects cell samples from a cell site (3430), the samples are analyzed in the LOC and μTAS and the data sent to the analytical module (3405) for modeling. The modeling data are sent to therapeutic module 1 (3415), which sends a radioactive isotope to tag the cell site. Therapeutic module 2 (3420) of iMD 1 and the therapeutic modules 1 (3450) and 2 (3455) then target the sell site with therapies.

Figure 35:
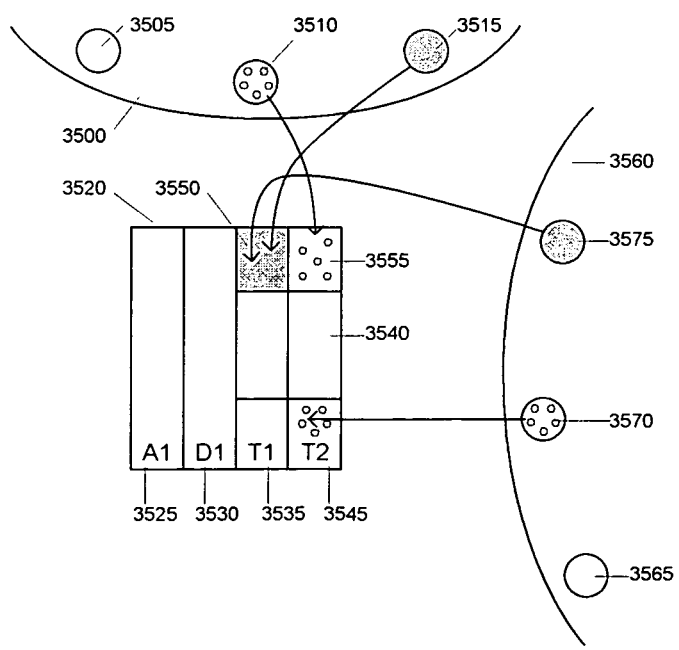
FIG. 35 is a schematic diagram showing the use of an iMD to harvest antibodies and cells and store the antibodies in the therapeutic module.

FIG. 35 shows the use of an iMD to harvest antibodies and cells and store the antibodies in the therapeutic module. The antibodies (3515 and 3575) from tissue one (3500) and tissue 2 (3560) are stored in therapeutic module 1 compartments (3550), while cells (3510) from tissue 1 are stored in a compartment (3555) of therapeutic module 2. Cells (3570) from tissue 2 are also stored in a compartment (3545) of therapeutic module 2 as shown. The stored cells and antibodies are useful for both analysis and for therapeutic applications.

Figure 36:
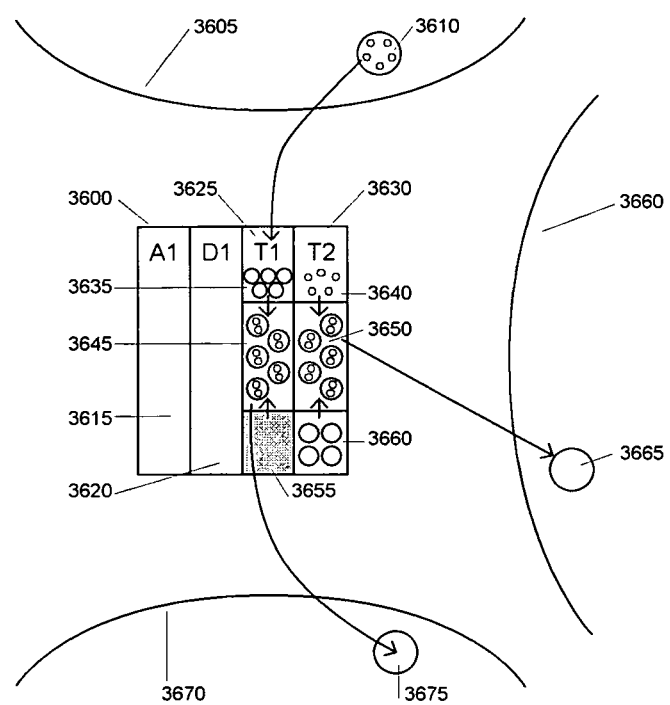
FIG. 36 is a schematic diagram showing an iMD that coats engineered viruses with harvested antibodies and proteins for treating multiple tumors simultaneously.

FIG. 36 shows an iMD that coats engineered viruses with harvested antibodies and proteins for treating multiple tumors simultaneously. Antibodies (3610) are harvested from tissue (3605) in a compartment of therapeutic module 1 (3625). The harvested antibodies are used to coat engineered viruses (3645 and 3650). Proteins are also used (3640) to coat engineered viruses in order to direct the viruses to the preferred location and to enable the viruses to penetrate specific cell receptors. The engineered viruses are delivered to cell sites at 3665 and 3675 in different tissues (3660 and 3670).

Figure 37:
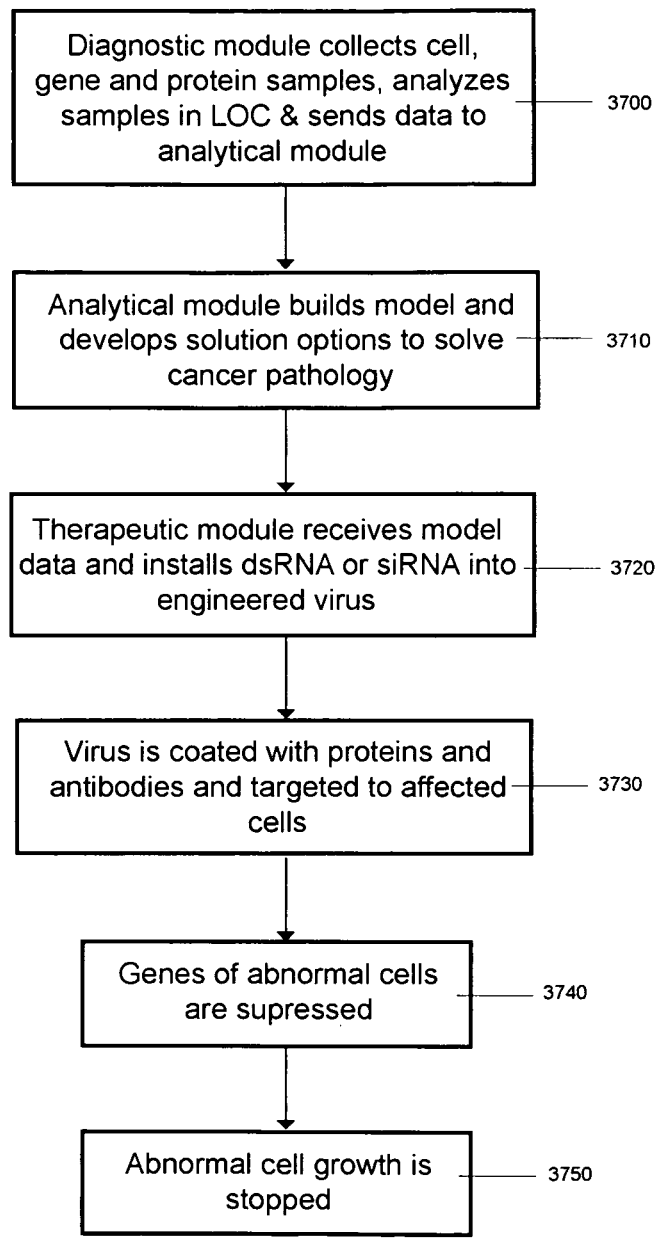
FIG. 37 is a flow chart describing the process of using an iMD to apply RNAi therapy to cancer to stop abnormal cell growth.

FIG. 37 shows the process of using an iMD to apply RNAi therapy to cancer to stop abnormal cell growth. Once the diagnostic module collects cell, gene and protein samples, analyzes the samples in the LOC and sends the data to the analytical module (3700), the analytical module builds a model and develops solution options to solve cancer pathology (3710). The therapeutic module receives model data and installs dsRNA and siRNA into an engineered virus (3720). The virus is coated with proteins and antibodies and targeted to affected cells (3730). The genes of abnormal cells are suppressed (3740) and abnormal cell growth is stopped (3750).

Figure 38:
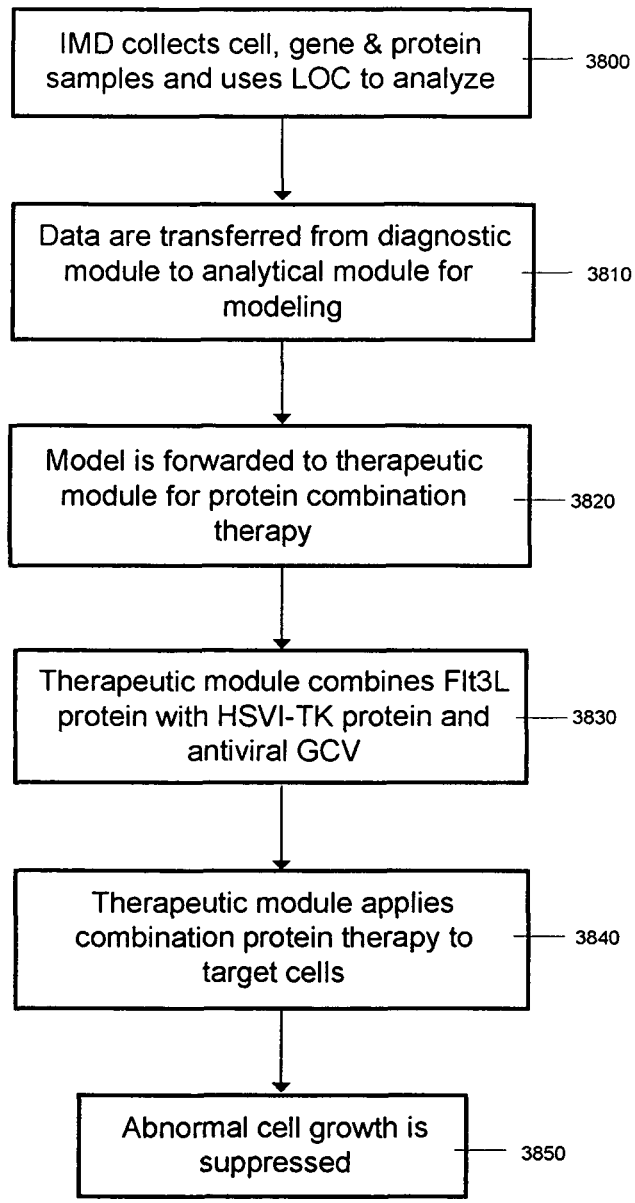
FIG. 38 is a flow chart describing the process of using an iMD to apply protein combination therapy to treat abnormal cell growth.

FIG. 38 shows the process of using an iMD to apply protein combination therapy to treat abnormal cell growth. After the iMD collects cell, gene and protein samples and uses the LOC to analyze the samples (3800), the data are transferred from the diagnostic module to the analytical module for modeling (3810). The model is forwarded to the therapeutic module for protein combination therapy (3820) and the therapeutic module combines Flt3L protein with HSV1-TK protein and antiviral GCV (3830). The therapeutic module applies the combination protein therapy to target cells (3840) and abnormal cell growth is suppressed (3850). In another embodiment, PARP inhibitors are used for specific types of cancers, for example, those that involve the BRCA 1 and 2 genes.

Figure 39:
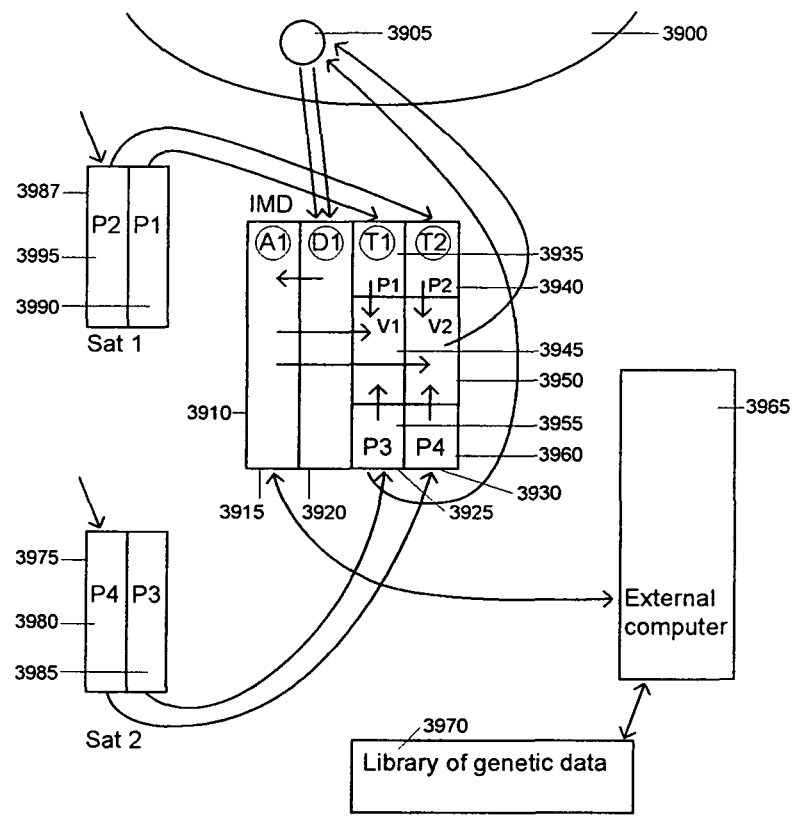
FIG. 39 is a schematic diagram showing the use of an iMD, satellite devices and external computer resources to combine proteins, insert the combined proteins into a virus and apply the virus and proteins to treat abnormal cell growth.

FIG. 39 shows the use of an iMD, satellite devices and external computer resources to combine proteins, insert the combined proteins into a virus and apply the virus and proteins to treat abnormal cell growth. Once cell samples are collected from the cell site (3905) by the diagnostic module (3920) and analyzed in the LOC and μTAS, the data are forwarded to the analytical module (3915) for modeling. Solution options from the model are forwarded to the therapeutic modules (3925 and 3930), which combine proteins in specific chambers with viruses. Protein 1 (3935) and protein 3 (3955) are combined with virus 1 (3945) in therapeutic module one. Protein 2 (3940) and protein 4 (3960) are combined with virus 2 (3950). Both modified viruses are applied to the cell site. Internal satellites (3975 and 3987) resupply the proteins as required. The analytical module obtains supplementary computation resources by accessing an external computer (3965), which in turn accesses a library of genetic data (3970). This process continues until the problem is solves.

Figure 40:
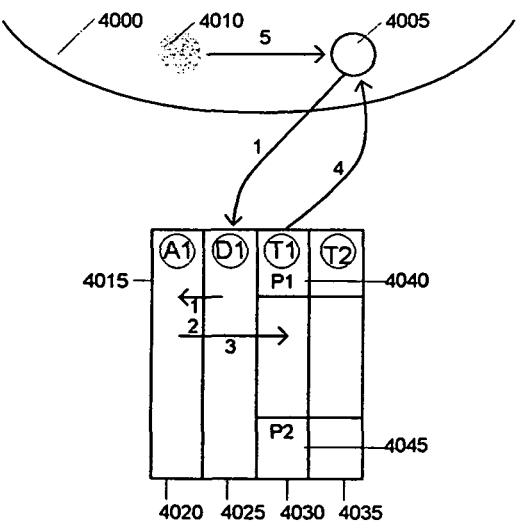
FIG. 40 is a schematic diagram showing the use of an iMD to coat abnormal cells with proteins to attract HIS antibodies.

FIG. 40 shows the use of an iMD to coat abnormal cells with proteins to attract HIS antibodies. The sequence of the process begins with the collection of cell samples from the cell site (4005) by the diagnostic module (4025), the analysis of the samples by the LOC and the transfer of the data to the analytical module (4020) for modeling. The solution options for remedies are then transferred to the therapeutic module 1 (4030), which combines proteins 1 (4040) and 2 (4045) and applies the remedy to the cell site. The concoction then stimulates an antibody cascade which attacks the abnormal cells.

Figure 41:
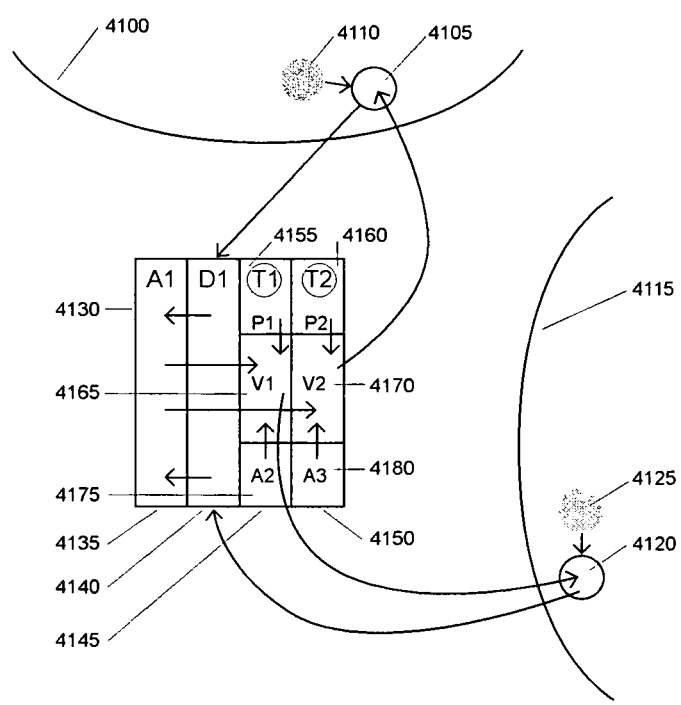
FIG. 41 is a schematic diagram showing the use of an iMD to combine proteins with viruses to simultaneously treat two abnormal cell clusters in which the engineered virus recruits antibodies in the HIS to attack the tumors.

FIG. 41 shows the use of an iMD to combine proteins and antibodies with viruses to simultaneously treat two abnormal cell clusters in which the engineered virus recruits antibodies in the HIS to attack the tumors. After cell samples (4105 and 4120) are collected by the diagnostic module (4140) and analyzed in the LOC and μTAS, the data are forwarded to the analytical module (4135) for modeling and the solution options are supplied to therapeutic modules 1 (4145) and 2 (4150). Therapeutic module 1 combines protein 1 with antibody 2 into virus 1 (4165) and applies the modified virus to the cell site in tissue 4115. Antibodies attack the cell site and the tumor is negated. Therapeutic module 2 combines protein 2 with antibody 3, inserts these into virus 2 (4170) and applies the modified virus to the cell site in tissue 4100. Antibodies attack the cell site and the tumor is negated.

Figure 42:
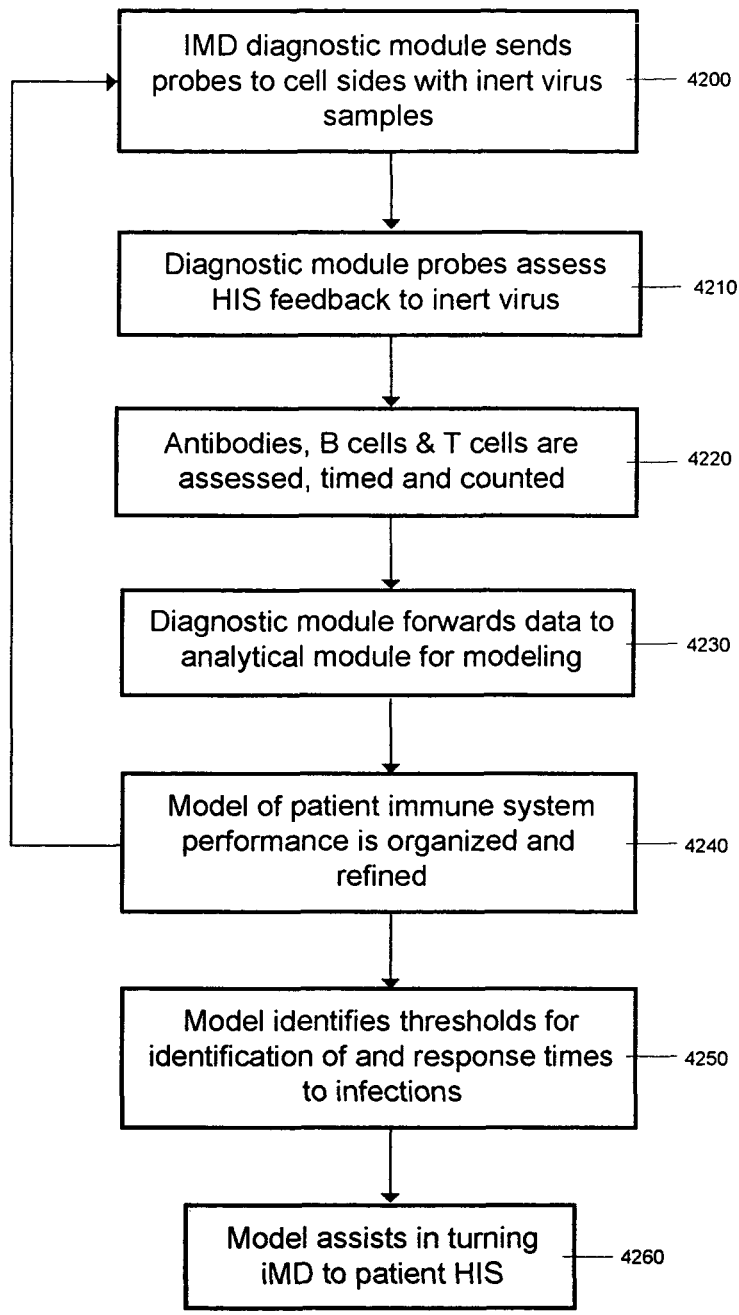
FIG. 42 is a flow chart describing the process of using an iMD to model a patient HIS.
Figure 47:
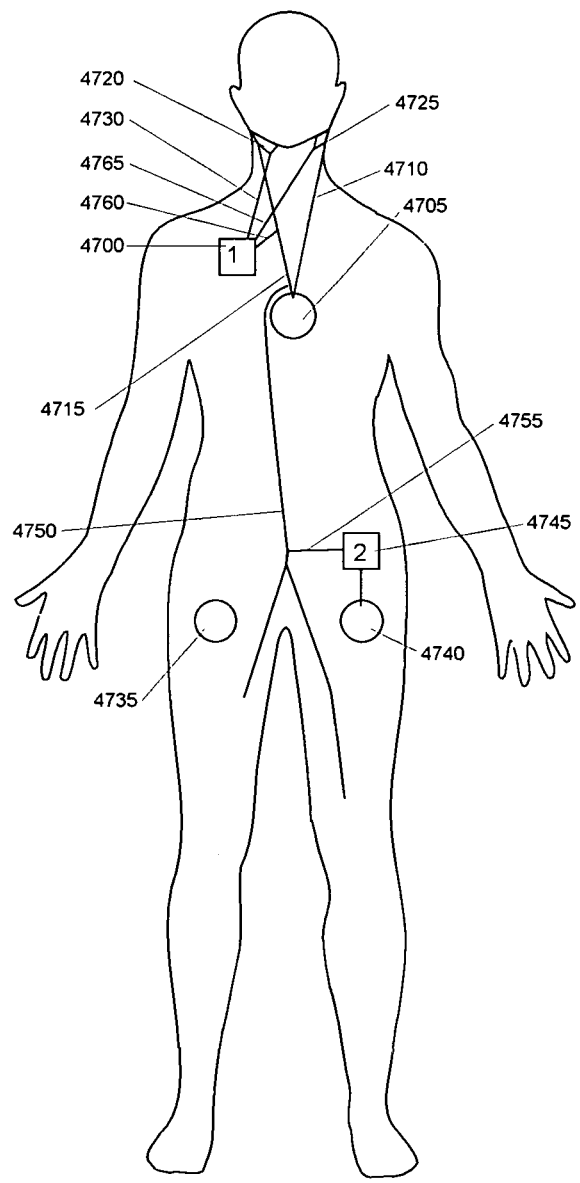
FIG. 47 is a drawing of iMDs in two positions used to access the lymph system.
Figure 48:
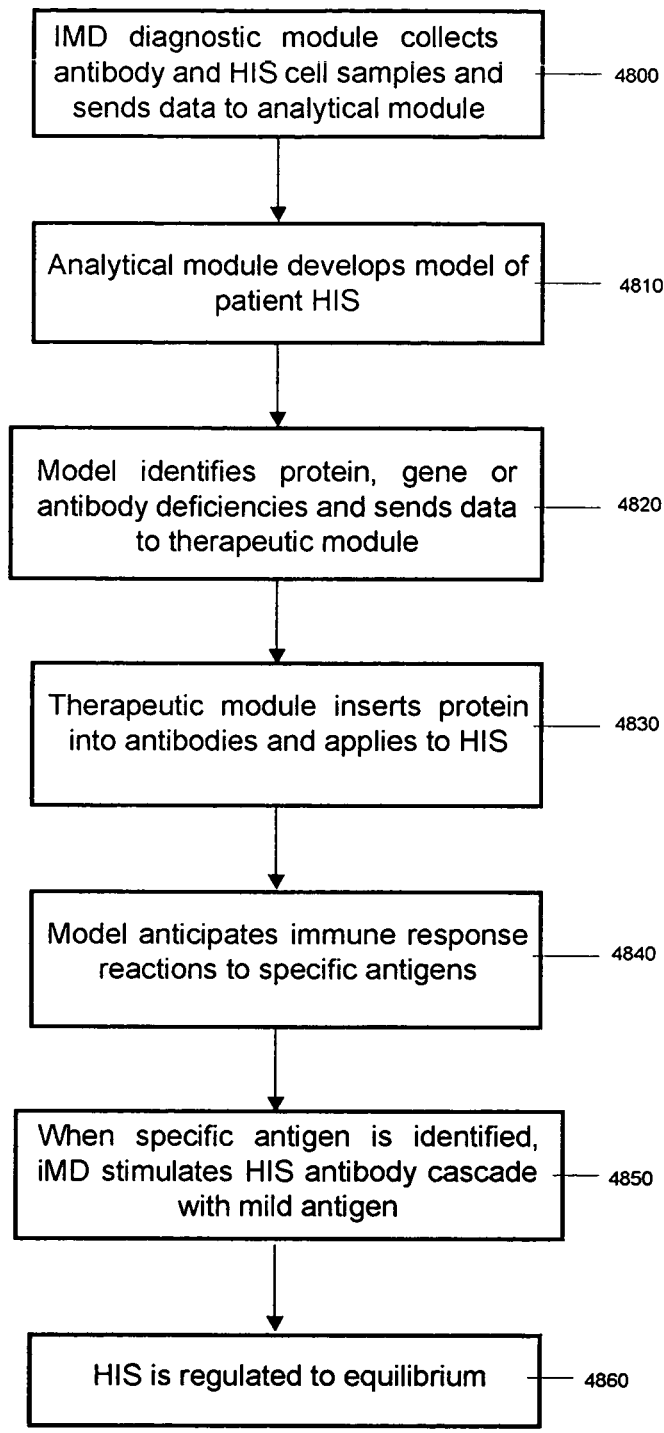
FIG. 48 is a flow chart describing the process of using an iMD to regulate the HIS.
Figure 49:
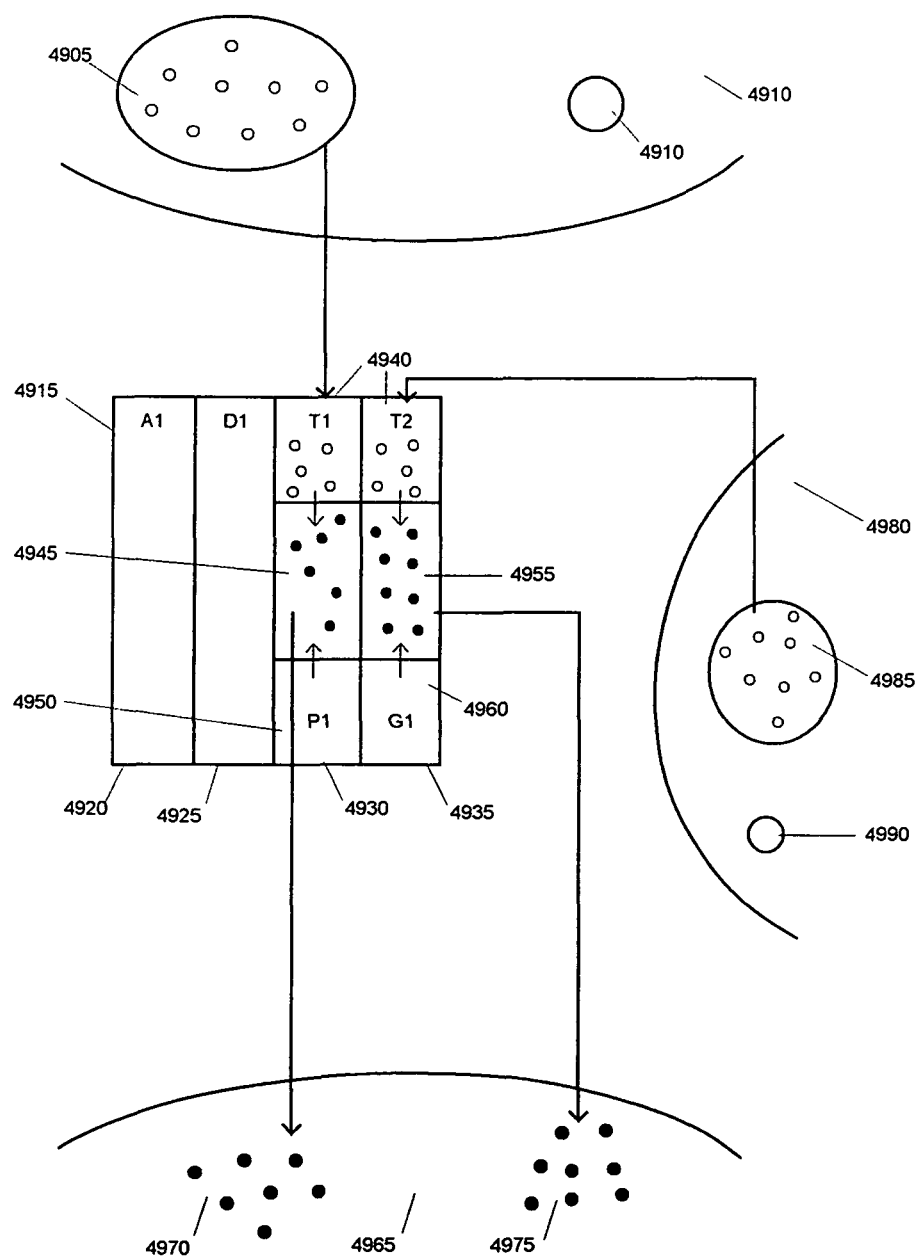
FIG. 49 is a schematic diagram showing the use of an iMD to harvest antibodies and apply modified antibodies to specific tissue.
Figure 50:
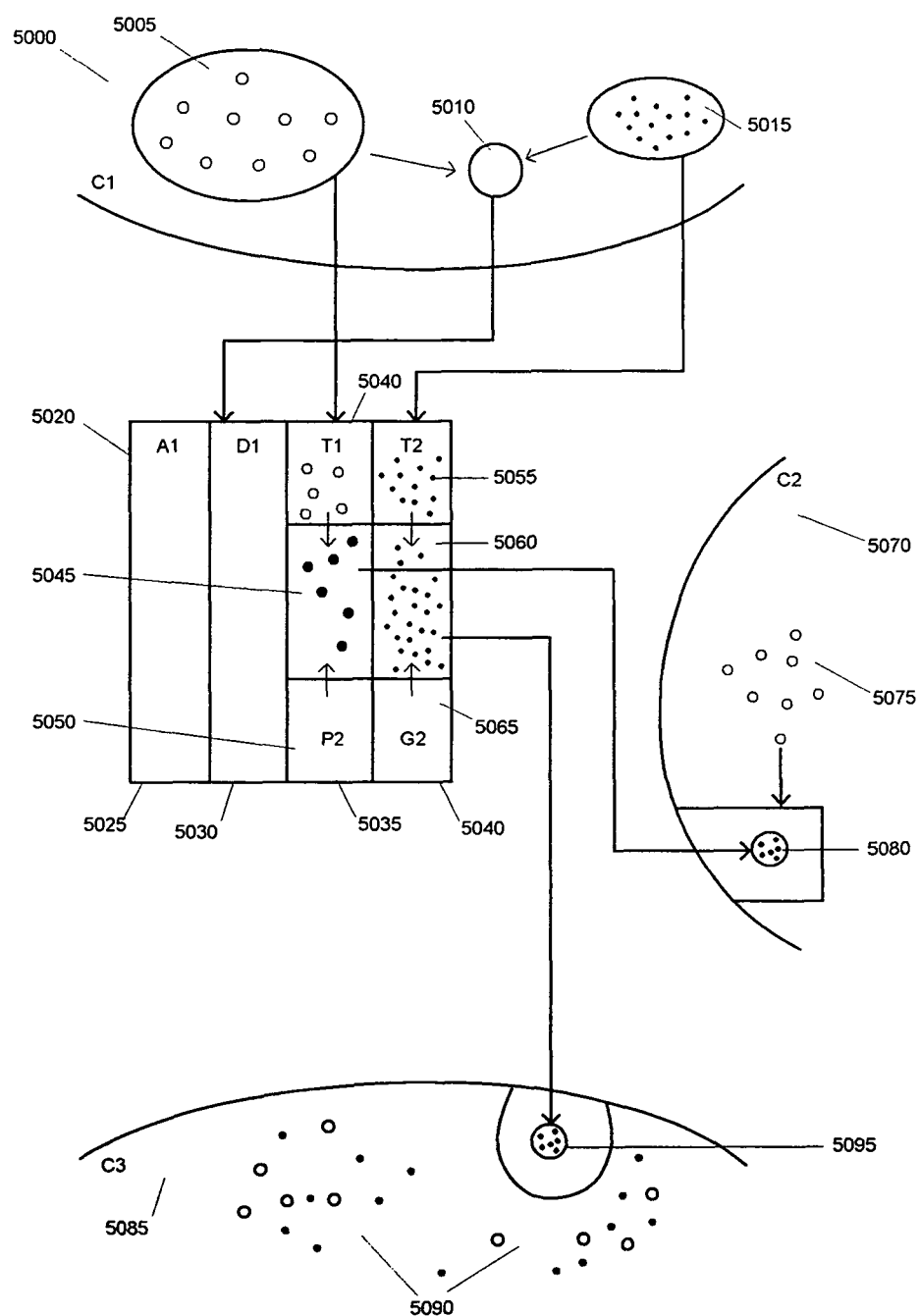
FIG. 50 is a schematic diagram showing the use of an iMD to harvest antibodies and insert modified antibodies into new tissue to protect against antigens.
Figure 51:
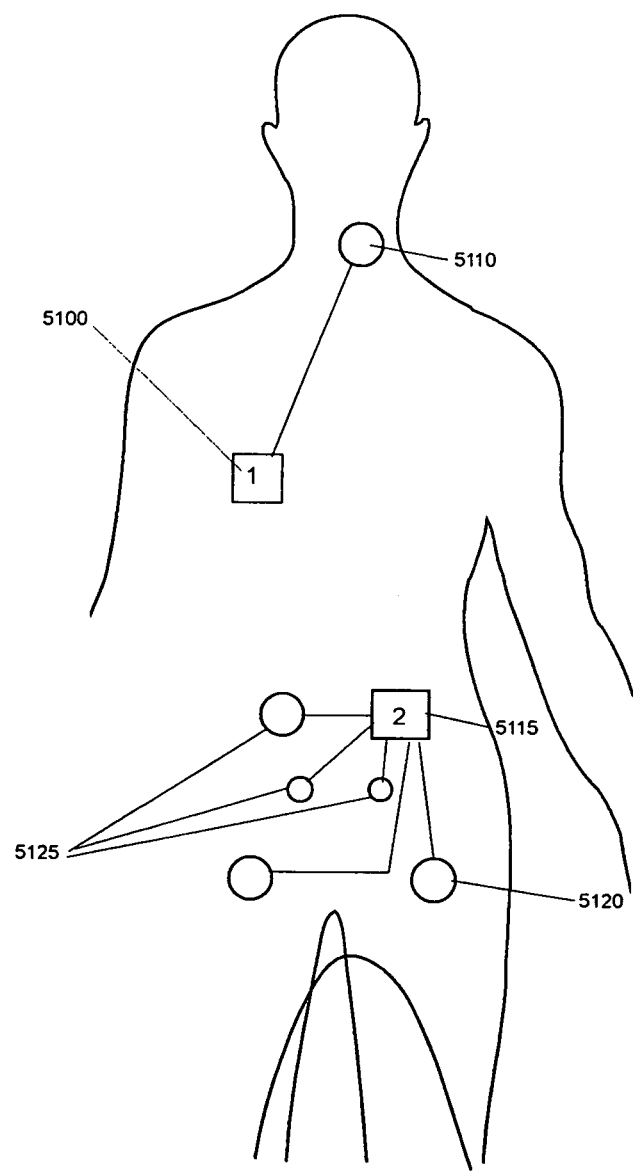
FIG. 51 is a drawing of iMDs in two positions connected to the human endocrinological system to balance hormone chemistry.
Figure 52:
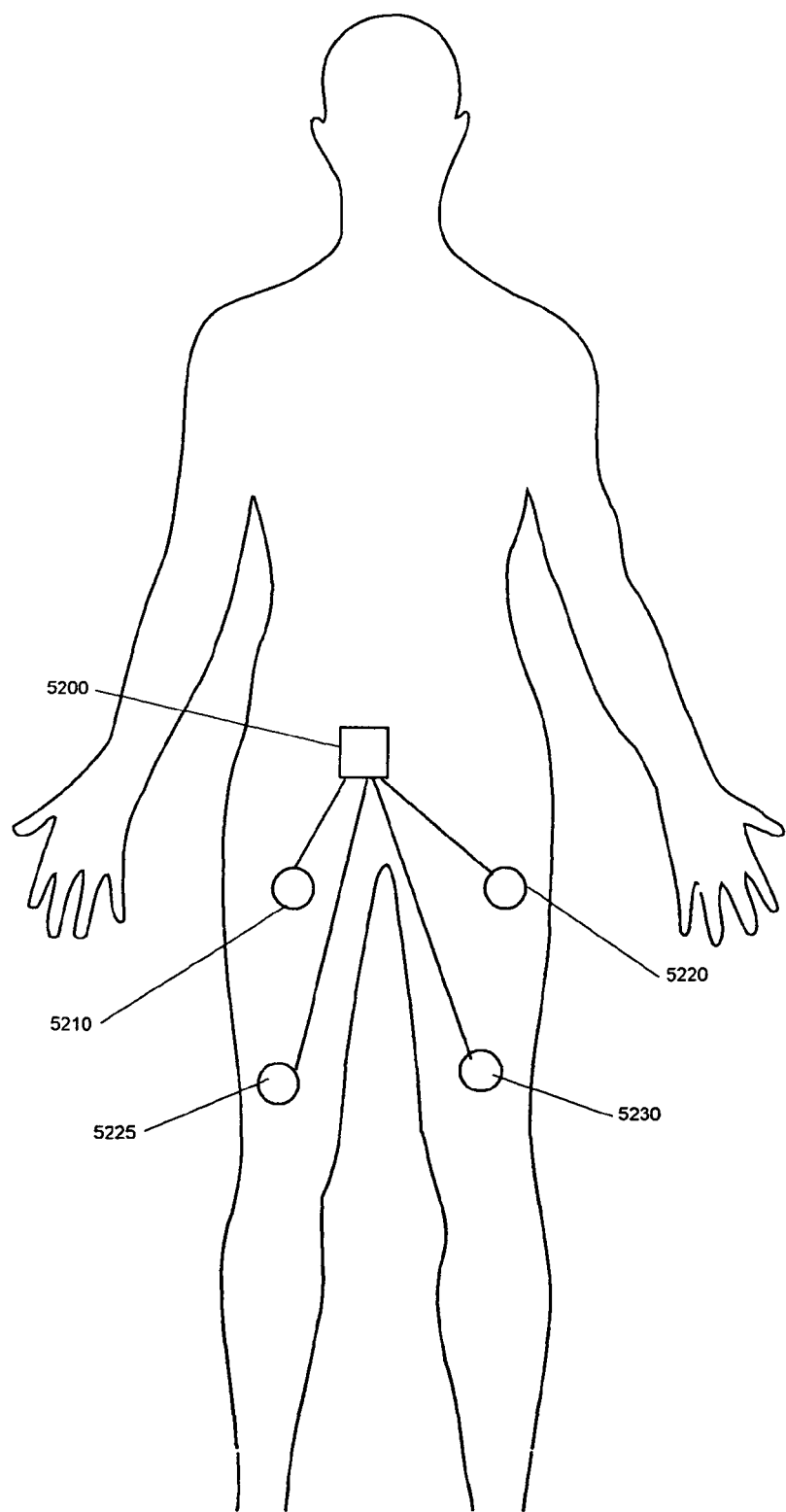
FIG. 52 is a drawing of an iMD connected to active sensors to report on therapy progress.
Figure 53:
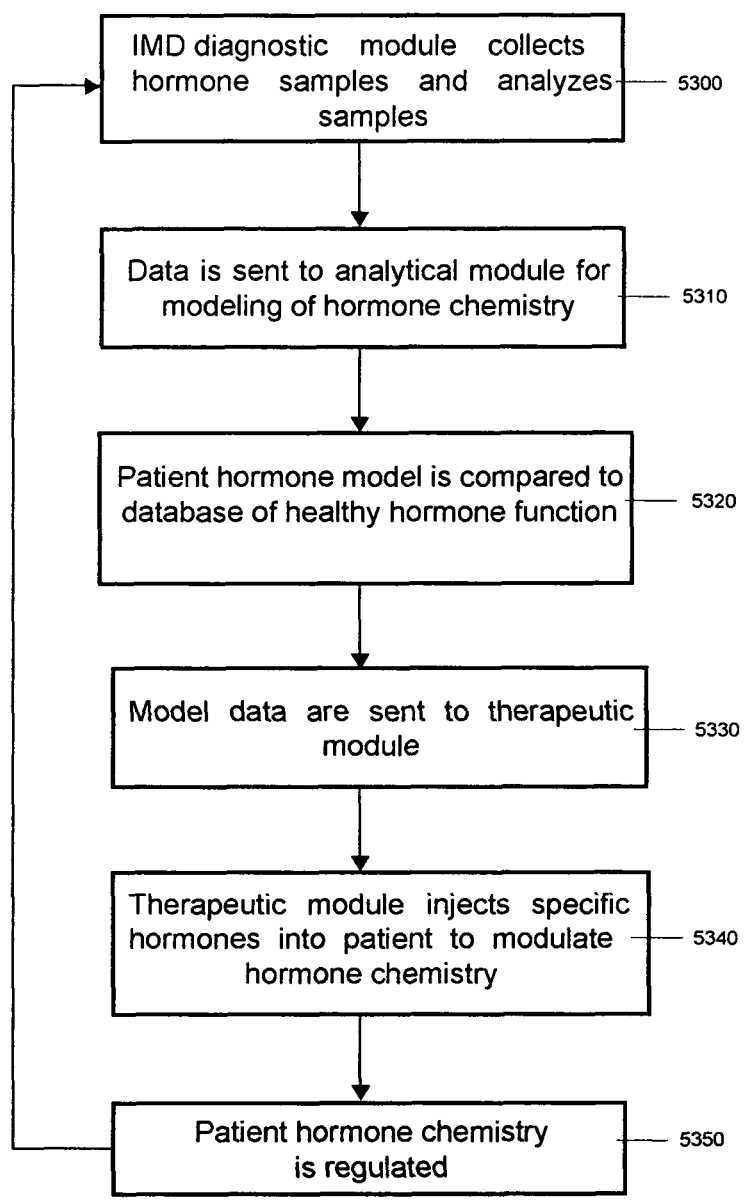
FIG. 53 is a flow chart describing the process of using an iMD to modulate hormone chemistry.
Figure 54:
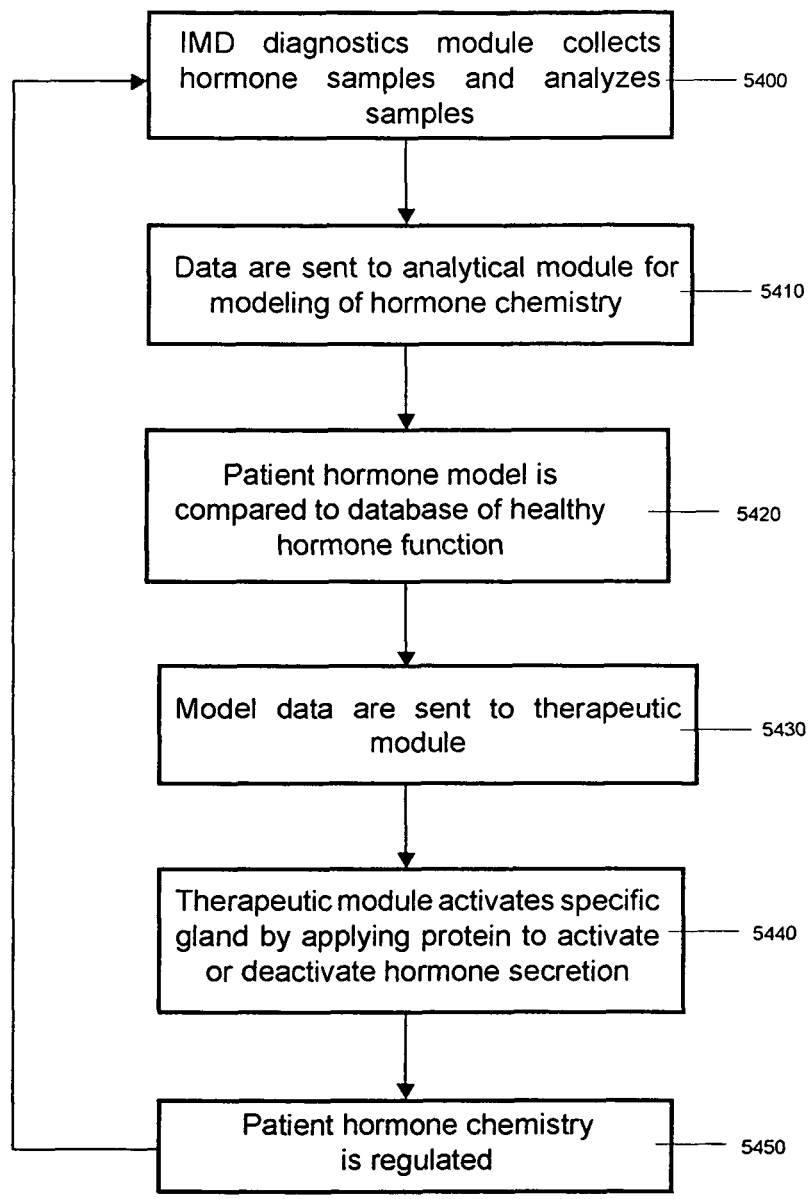
FIG. 54 is a flow chart describing the process of using an iMD to apply protein to activate or deactivate hormone secretion in glands.
Figure 55:
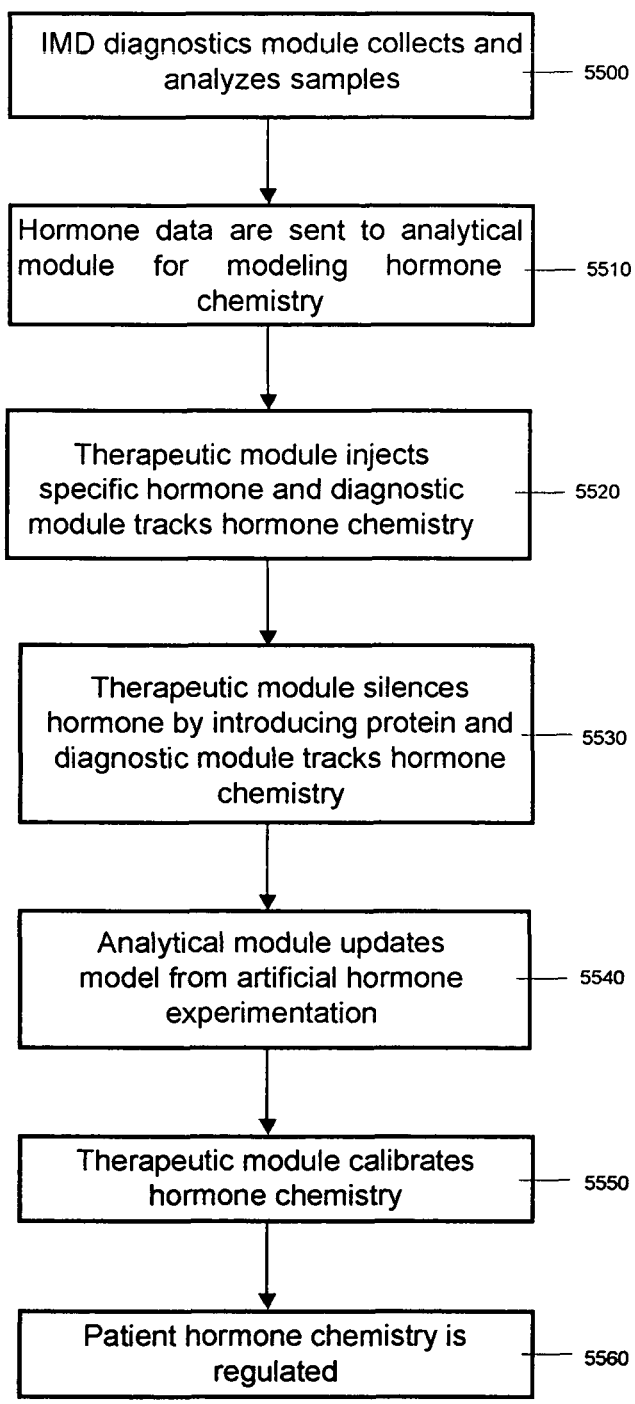
FIG. 55 is a flow chart describing the process of using an iMD to engage in an experimentation process to calibrate hormones.
Figure 56:
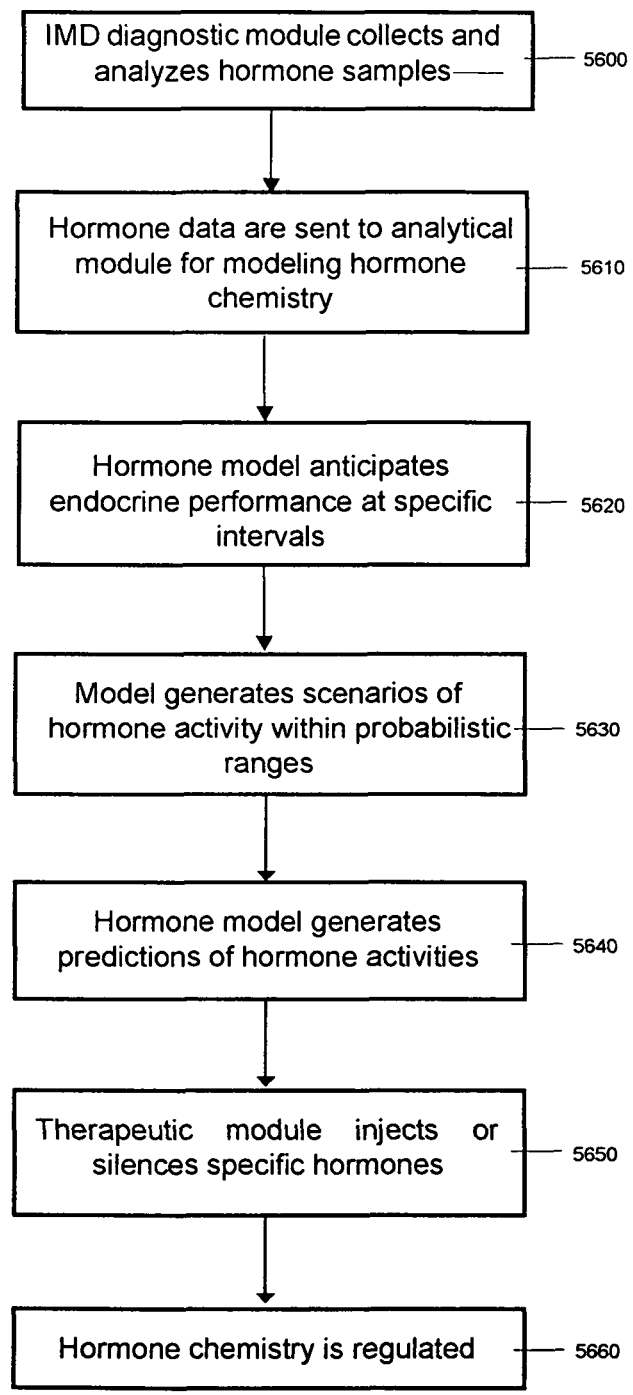
FIG. 56 is a flow chart describing the process of using an iMD to model and apply hormones by anticipating a hormone regulation by the model in treating an endocrinological condition.

FIG. 42 shows the process of using an iMD to model a patient HIS. After the iMD diagnostic module sends probes to cell sites with inert virus samples (4200), the diagnostic module probes assess HIS feedback to the inert virus (4210). The antibodies, B cells and T cells are assessed, timed and counted (4220) and the diagnostic module forwards data to the analytical module for modeling (4230). The model of the patient's immune system performance is organized and refined (4240) and the model identifies thresholds for identification of, and response times to, infections (4250). The model assists in tuning the iMD to the patient's unique HIS (4260).

FIG. 43 shows the use of an iMD applied to RNAi therapy to disable virus genes and proteins in the HIS. Once cell samples are collected from cell sites (4325 and 4340) by the diagnostic module (4310) and the data from the LOC and μTAS analyses sent to the analytical module (4305) for modeling, the solution options are forwarded to the therapeutic modules 1 (4315 and 4320). The therapeutic modules then apply RNAi therapy to disable virus genes and proteins in the HIS (4330, 4335, 4345 and 4350).

FIG. 44 shows the process of using an iMD for protein therapy against a viral infection. After the iMD diagnostic module probes are dispatched to infected cells to collect samples (4400), the probes return to the diagnostic module for evaluation of the infectious agent (4410) and data are sent to the analytical module for modeling of virus composition (4420). The modeling data are transmitted to the therapeutic module, which applies protein or peptides to inhibit the virus infectious aspect (4430) and proteins are inserted in antibodies for delivery to the virus (4440), after which the virus is rendered inert (4450).

FIG. 45 shows the process of using an iMD for gene therapy against a viral infection. Once the iMD diagnostic module probes are dispatched to infected cells to collect samples (4500), the samples are evaluated in the diagnostic module and data sent to the analytical module for viral modeling (4510). The modeling data are transmitted to the therapeutic module, which inserts genes to disable the infectious viral gene (4520) and modified genes are inserted in antibodies for delivery to the virus (4530) until the virus is rendered inert (4540).

FIG. 46 shows the process of using an iMD to enhance a host antibody reaction to a virus. After the iMD diagnostic module probes collect infected cell samples (4600), the samples are evaluated in the diagnostic module and data sent to the analytical module for viral modeling (4610). The modeling data is transmitted to the therapeutic module, which activates a protein to stimulate HIS antibody cascade (4620) and the therapeutic module releases mild antigens to stimulate an antibody cascade (4630). The virus is then attacked by HIS antibody acceleration (4640).

In one embodiment, the iMD is used for rapid prototyping of a custom vaccine. After initially analyzing the patient HIS and a specific virus, and comparing the patient HIS to a database of healthy immune system operation, the iMD supplies a small amount of antigen to produce an antibody response to defeat a specific virus. The iMD assesses the response to the antigen and modulates the HIS reaction by restricting or enhancing the supply of the antigen.

FIG. 47 shows the two positions used by iMDs to access the lymph system. IMD 1 (4700) accesses lymph nodes 4720 and 4725 while iMD 2 (4745) accesses the locations at 4740 and 4755. In another embodiment, the iMDs access the spleen so as to stimulate a monocyte cascade.

FIG. 48 shows the process of using an iMD to regulate the HIS. After the iMD diagnostic module collects antibody and HIS cell samples and sends data to the analytical module (4800), the analytical module develops a model of the patient HIS (4810). The model identifies protein, gene or antibody deficiencies and sends data to the therapeutic module (4820), which inserts protein into antibodies and applies to the HIS (4830). The model anticipates immune response reactions to specific antigens (4840). When a specific antigen is identified, the iMD stimulates the HIS antibody cascade with a mild antigen (4850) and the HIS is regulated to equilibrium (4860).

FIG. 49 shows the use of an iMD to harvest antibodies and apply the modified antibodies to specific tissue. Patient antibodies (4905 and 4985) are harvested from different tissues (4900 and 4980) by the iMD (4915) therapeutic modules (4940 and 4935). The antibodies are combined with protein 1 (4950) in T1 (at 4945) and gene 1 (4960) in T2 (at 4955). The modified antibodies are then applied to cells at cell sites 4970 and 4975 in tissue 4965. The pathology in the target tissue is managed.

FIG. 50 shows the use of an IMD to harvest antibodies and insert modified antibodies into new tissue to protect against antigens. While tracking a cell site, the diagnostic module (5030) collects cell samples and data forwarded to the analytical module (5025) for a modeling solution. Patient antibodies (5005) are harvested from tissue C1 by therapeutic module 1 (5035) and therapeutic module 2 (5040). The antibodies are combined with protein 2 (5050) at 5045 in T1 and with gene 2 (5065) at 5060 in T2. The modified antibodies are then applied to cell sites at 5080 in C2 (5070) and 5095 in C3 (5085). The modified antibodies allow the cells to resist the antigens (5075 in C2 and 5090 in C3).

FIG. 51 shows two iMDs in two positions connected to the human endocrinological system to balance hormone chemistry. IMD 1 (5100) is connected to the thyroid glands (5110) while iMD 2 (5115) is connected to adrenal glands (5120), the pancreas (5125) and (for women) the ovaries. FIG. 52 shows an iMD connected to active sensors to report on therapy progress. The iMD (5200) is shown connected to the sensors (5210 to 5230).

FIG. 53 shows the process of using an iMD to modulate hormone chemistry. After the iMD diagnostic module collects hormone samples and analyzes samples (5300), the data are sent to the analytical module for modeling of hormone chemistry (5310). The patient hormone model is compared to a database of healthy hormone function (5320) and the model data are sent to a therapeutic module (5330). The therapeutic module injects specific hormones into the patient to modulate hormone chemistry (5340) and patient hormone chemistry is regulated (5350). The process then repeats.

FIG. 54 describes the process of using an iMD to apply protein to activate or deactivate hormone secretion in glands. Once the iMD diagnostic module collects hormone samples and analyzes the samples (5400), data are sent to the analytical module for modeling of hormone chemistry (5410). The patient hormone model is compared to a database of healthy hormone function (5420) and model data are sent to the therapeutic module (5430). The therapeutic module activates specific gland(s) by applying protein to activate or deactivate hormone secretion (5440) and patient hormone chemistry is regulated (5450). The process then repeats.

FIG. 55 shows the process of using an iMD to engage in an experimentation process to calibrate hormones. After the iMD diagnostic module collects and analyzes hormone samples (5500), the hormone data are sent to the analytical module for modeling hormone chemistry (5510) and a therapeutic module injects a specific hormone. The diagnostic module tracks hormone chemistry (5520) and the therapeutic module silences the hormone by introducing a protein. The diagnostic module continues to track the hormone chemistry (5530). The analytical module updates the model from the artificial hormone experimentation (5540) and the therapeutic module calibrates the hormone chemistry (5550). The patient hormone chemistry is regulated (5560).

FIG. 56 shows the process of using an iMD to model and apply hormones by anticipating a hormone regulation by the model in treating an endocrinological condition. After the iMD diagnostic module collects and analyzes hormone samples (5600), the hormone data are sent to the analytical module for modeling hormone chemistry (5610). The hormone model anticipates endocrine performance at specific intervals (5620). The model generates scenarios of hormone activity within probabilistic ranges (5630) and predictions of hormone activities (5640). The therapeutic module injects or silences specific hormones (5650) and hormone chemistry is regulated (5660).

In another embodiment of the iMD applied to obesity, an iMD is located near the gastro-intestinal system and connected to the vagus nerve. The iMD modulates electrical pulses to the vagus nerve to suppress appetite.

FIG. 57 is a table of cancer genes applied to specific cancer types that are addressed by the iMD to solve cancer pathologies.

FIG. 58 is a table describing the different configurations of cell, virus and protein types applied to solving pathologies using iMDs. The table lists combinations of viruses, antibodies, nanodevices and cells that are combined in order to treat specific conditions. Specific coatings (such as proteins and antibodies) are directed at optimizing navigation. Specific coatings (proteins) enable a delivery vehicle (virus or nanodevices) to penetrate cell surface receptors. Specific coatings (antibodies) are useful for immune resistance.

The application of the iMD system to the systems specified are intended to limit their application. The iMD system is also useful in application to the gastro-intestinal system, to the muscular system and to the skeletal system. The iMD system is also applicable to in utero treatment for a fetus. The iMD system is also useful in application to specific genetic disorders because it is designed to assess genetic mutations and solve the mutations with gene, protein and RNAi therapies.

I claim:

1. A method for operation of a medical device for diagnostics, analysis and therapeutics for treatment of disease, comprising:
   a set of layers of medical device components, a set of compartments for storage of chemicals and biologicals, a set of microfluidic components, including tubes, valves and gates, circuitry configured to control and connect device components, a lab-on-a-chip (LOC) component in a diagnostic module, an analytical module, including a database, for pathology modeling and therapeutic solution modeling and a therapeutic module comprised of a set of compartments, the method comprising;
   connecting the diagnostic, analytical and therapeutic modules with electrical interconnects;
   activating the diagnostics process of obtaining cell, DNA, RNA and/or protein samples from the patient;
   analyzing the cell, DNA, RNA and/or protein samples in the LOC of the diagnostic module;
   forwarding the LOC analysis data to the analytical module for modeling of the pathology;
   generating remedial solution options from the model in the analytical module;
   forwarding solution options for therapeutic recommendations;
   configuring the therapeutic module to release specific chemicals and/or biologicals from compartments on at least one of a set of layers through the micro fluidic components in specific measured doses according to the model recommendations;
   activating the therapeutic module to combine chemicals and/or biologicals; and
   configuring the therapeutic module to transmit the combination of chemicals and/or biologicals to a cell site in a patient to treat disorders.

2. The method of claim 1, further comprising:
   transmitting in a patient the therapeutic combination of chemicals and/or biologicals to treat cardiovascular disorders, including cerebrovascular disorders, blood clot disorders, arteriosclerosis disorders, hemophilia disorders, anemia disorders and/or thrombocytopenia disorders.

3. The method of claim 1, further comprising:
   transmitting in a patient the therapeutic combination of chemicals and/or biologicals to treat abnormal cells, including neoplasties, cancer metastases, blocking angiogenesis in tumors, gene replacement of mutated genes and/or protein replacement of specific combinations of dysfunctional proteins.

4. The method of claim 1, further comprising:
   Receiving biological and chemical samples from feedback of the application of a therapy to the pathology in the diagnostic module;
   configuring the diagnostic module that includes the LOC to analyze the biological samples and forwards the analyses to the analytical module;
   configuring the analytical module to model the sample data, develop refined solution options to solve the pathology and forward the solution model to the therapeutic module;
   configuring the therapeutic module to combine chemicals and/or biologicals to update the solution to solve the pathology; and
   managing the pathology with a revised therapy.

5. The method of claim 2, further comprising:
   collecting biomarkers in the diagnostic module;
   analyzing the biomarkers in the analytical module;
   developing an evolving model based on new data inputs of biomarkers;
   applying the model to track and anticipate disease progression and scenario pathway vectors;
   identifying a blood clot in a cerebrovascular pathway;
   identifying and selecting a solution option for solving cerebral disequilibrium; and
   activating the medical device to apply chemicals to administer the remedy.

6. The method of claim 2, further comprising:
   identifying BAD associated protein isoforms in the diagnostic module;
   forwarding data to the analytical module;
   constructing a model in the analytical module;
   employing the model to compare the BAD biomarkers to a database of brain chemistry;
   developing remedy solution pathway vectors with the model;
   employing the therapeutics module to combine chemicals and/or biologicals to activate the remedy solution option; and
   activating the therapeutics module to apply a remedy.

7. The method of claim 2, further comprising:
   activating the medical device to collect cell and protein samples;
   analyzing the cell and protein samples in the diagnostic module;
   forwarding data to the analytical module;
   building a model in the analytical module to map at least one region of the brain;
   activating the analytical module to produce remedy solution options;
   forwarding the data to the therapeutic module;
   applying stem cells to affected regions of the brain; and
   monitoring the remedy progress and stem cell assimilation by receiving updated cell and protein samples.

8. The method of claim 1, further comprising:
   inputting biomarker samples of cardio reactive protein (CRP) and lipoprotein levels into the medical device diagnostics module;
   identifying locations of plaque buildup and arterial calcification in the vasculature by analyzing biological samples in the diagnostics module;
   forwarding CRP and lipoprotein data to the analytical module;
   generating a model to map the vasculature in the analytical module;
   identifying specific proteins associated with vasculature zip codes that differentiate locations in the vasculature;
   forwarding the model data to the therapeutic module;
   activating the therapeutic module to combine proteins to direct therapeutic remedies to specific vascular locations; and
   applying the therapy until arterial plaque is in equilibrium.

9. The method of claim 2, further comprising:
   collecting biological samples about specific diseased blood vessels from atherosclerosis in the diagnostics module;

forwarding the data to the analytical module;
building a model of patient vasculature to identify locations of diseased blood vessels in the analytical modules;
forwarding the model data to the therapeutic module;
applying VEGF or FGF 1 to cell clusters or modulating the application of PKC-E in the vasculature; and
regulating the vascular protein levels to an equilibrium state.

10. The method of claim 2, further comprising:
collecting and forwarding cell and protein samples to the diagnostics module;
analyzing biological samples to identify a blood disorder in the diagnostics module;
forwarding the data to the analytical module;
developing model solution options in the analytical module; and
activating the therapeutic module to apply protein replacement therapy.

11. The method of claim 3, further comprising:
collecting biomarkers in the diagnostic module to detect the presence of cancer cells;
analyzing data in the LOC in the diagnostic module;
forwarding the data to the analytical module;
activating the analytical module to model the pathology to identify the cell site;
activating the analytical module to build a model to identify genetic mutations in the cancer cells;
developing a model of solution options in the analytical module;
constructing at least one drug in the therapeutic module tailored to the tumor; and
applying the at least one drug to the cell site.

12. The method of claim 3, further comprising:
receiving cell and protein samples of a cancer tumor at the diagnostic module;
analyzing the biological sample data in the LOC of the diagnostic module;
transferring the data to the analytical module;
developing a model of the cancer tumor in the analytical module;
activating the therapeutic module to combine specific genetic material;
inserting the genetic material into a modified AAV or lentivirus coated with proteins and antibodies;
combining the virus with immune cell microRNA;
transferring the genetic material to the affected cell site;
facilitating the modified virus to resist immune response and penetrate cell surface TK receptors; and
stimulating affected cells to produce healthy proteins and stop generating cancer cells.

13. The method of claim 3, further comprising:
collecting cell, gene and/or protein samples at the diagnostic module;
activating the LOC in the diagnostic module to analyze the biological samples;
forwarding the data to the analytical module;
building a model to develop solution options to solve cancer pathology in the analytical module;
transferring the model with solution options to the therapeutic module;
installing dsRNA or siRNA into an engineered virus in the therapeutic module;
coating the virus with proteins and antibodies to target affected cells;
applying the engineered remedy; and
suppressing abnormal cell growth.

14. The method of claim 3, further comprising:
collecting cell, gene and/or protein samples at the diagnostic module;
activating the LOC in the diagnostic module to analyze the biological samples;
forwarding the data to the analytical module;
building a model to develop solution options to solve cancer pathology in the analytical module;
combining Flt3L protein with HSVI-TK protein and antiviral GCV in the therapeutic module;
applying the combination protein therapy to target cells; and
suppressing abnormal cell growth.

15. A method for operation of a medical device for diagnostics and analysis of disease, comprising:
a set of layers of medical device components, a set of compartments for storage of chemicals and biologicals, a set of microfluidic components, including tubes, valves and gates, circuitry configured to control and connect a device components, a lab-on-a-chip (LOC) component in a diagnostic module, an analytical module, including a database, for pathology modeling and therapeutic solution modeling, the method comprising;
connecting the diagnostic and analytical modules with electrical interconnects;
activating the diagnostics process of obtaining cell, DNA, RNA and/or protein samples from the patient;
analyzing the cell, DNA, RNA and/or protein samples in the LOC of the diagnostic module;
forwarding the LOC data to the analytical module;
analyzing a pathology by generating a model in the analytical module and by comparing the data to the database; and
generating solution options for therapeutic recommendations of combining genes, RNA and/or proteins from the model by accessing the database in the analytical module.

16. The method of claim 15, further comprising:
receiving cell, DNA, RNA and/or protein samples from the patient after the application of a therapy;
analyzing the revised samples in the LOC in an iteration of testing a therapeutics solution;
forwarding the LOC data to the analytical module;
generating revised solution options from the model by accessing the database; and
developing updated solution options for therapeutic recommendations of combining gene, RNA and/or proteins.

17. A method for operation of a medical device for diagnostic analysis and therapeutics for treatment of disease, comprising:
a set of layers of medical device components, a set of compartments for storage of chemicals and biologicals, a set of microfluidic components, including tubes, valves and gates, circuitry and connectors configured to control a set of device components, an analytical module, including a database, for pathology modeling and therapeutic solution modeling, and a therapeutic module, the method comprising;
connecting the analytical and therapeutics modules with electrical interconnects;
generating descriptive modules of a pathology from biological data by comparing the data to a database in the analytical module;
configuring the analytical module to generate solution options from the model; and forwarding the solution options for therapeutic recommendations;

configuring the therapeutic module to release specific chemicals and/or biologicals from compartments on at least one of a set of layers through the micro fluidic components in specific measured doses according to the model recommendations;

activating the therapeutic module to combine chemicals and/or biologicals; and configuring the therapeutic module to transmit the combination of chemicals and/or biologicals to a cell site in a patient to treat disorders.

18. The method of claim 17, further comprising:

receiving biological and chemical samples from feedback of the application of a therapy to the pathology in the diagnostic module;

configuring the diagnostic module to analyze the biological samples in the LOC and forward the data to the analytical module;

configuring the analytical module to model the sample data;

developing refined solution options to solve the pathology;

forwarding the solution model to the therapeutic module;

configuring the therapeutic module to combine chemicals and/or biologicals to update the solution to solve the pathology; and managing the pathology with a revised therapy.

19. The method of claim 17, further comprising:

transmitting in a patient the therapeutic combination of chemicals and/or biologicals to treat abnormal cells, including neoplasties, cancer metastases, to blocking angiogenesis in tumors, gene replacement of mutated genes and/or protein replacement of specific combinations of dysfunctional proteins.

20. The method of claim 19, further comprising:

generating a model of dysfunctional genes in cancer cells by activating the analytical module;

sending the model data to the therapeutic module;

loading engineered genes into a AAV or lentivirus;

inserting the virus into stem cells;

targeting the modified stem cells to the affected cells; and stopping abnormal cell growth.

21. The method of claim 19, further comprising:

generating a model of dysfunctional genes in cancer cells in the analytical module;

sending the model data to the therapeutic module;

installing engineered proteins in antibodies;

injecting the engineered antibodies into stem cells;

targeting the modified stem cells to affected cells; and stopping abnormal cell growth.

* * * * *